United States Patent
Xing et al.

(10) Patent No.: US 10,611,764 B2
(45) Date of Patent: Apr. 7, 2020

(54) ARYL HYDROCARBON RECEPTOR LIGANDS FROM KYNURENINE

(71) Applicant: Wisconsin Alumni Research Foundation, Madison, WI (US)

(72) Inventors: Yongna Xing, Middleton, WI (US); Seunghyeon Seok, Madison, WI (US); Zhi-Xiong Ma, Madison, WI (US); John Feltenberger, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 16/185,870

(22) Filed: Nov. 9, 2018

(65) Prior Publication Data
US 2019/0135812 A1 May 9, 2019

Related U.S. Application Data

(60) Provisional application No. 62/583,903, filed on Nov. 9, 2017.

(51) Int. Cl.
| | |
|---|---|
| *C07D 471/16* | (2006.01) |
| *A61K 31/4375* | (2006.01) |
| *A61P 37/06* | (2006.01) |
| *C07D 487/16* | (2006.01) |
| *A61P 35/00* | (2006.01) |
| *A61K 31/519* | (2006.01) |

(52) U.S. Cl.
CPC ........ *C07D 471/16* (2013.01); *A61K 31/4375* (2013.01); *A61K 31/519* (2013.01); *A61P 35/00* (2018.01); *A61P 37/06* (2018.01); *C07D 487/16* (2013.01)

(58) Field of Classification Search
CPC .............................. C07D 471/16; C07D 487/16
See application file for complete search history.

(56) References Cited

PUBLICATIONS

Ahmadian et al. (2013). "PPARgamma signaling and metabolism: the good, the bad and the future." Nat Med 19(5): 557-566.
Bergander et al. (2004). "Metabolic fate of the Ah receptor ligand 6-formylindolo[3,2-b]carbazole." Chem Biol Interact 149(2-3): 151-164.
Bessede et al. (2014). "Aryl hydrocarbon receptor control of a disease tolerance defence pathway." Nature 511(7508): 184-190.
Bisson et al. (2009). "Modeling of the aryl hydrocarbon receptor (AhR) ligand binding domain and its utility in virtual ligand screening to predict new AhR ligands." J Med Chem 52(18): 5635-5641.
Bjeldanes et al. (1991). "Aromatic hydrocarbon responsiveness-receptor agonists generated from indole-3-carbinol in vitro and in vivo: comparisons with 2,3,7,8-tetrachlorodibenzo-p-dioxin." Proc Natl Acad Sci U S A 88(21): 9543-9547.
Bohar et al. (2015). "Changing the face of kynurenines and neurotoxicity: therapeutic considerations." Int J Mol Sci 16(5): 9772-9793.
Boitano et al. (2010). "Aryl hydrocarbon receptor antagonists promote the expansion of human hematopoietic stem cells." Science 329(5997): 1345-1348.
Brown et al. (1967). "The mass spectra of the kynurenines." Tetrahedron Letters 18: 1721-1726.
Chang et al. (1993). "Ten nucleotide differences, five of which cause amino acid changes, are associated with the Ah receptor locus polymorphism of C57BL/6 and DBA/2 mice." Pharmacogenetics 3(6): 312-321.
Changsirivathanathamrong et al. (2011). "Tryptophan metabolism to kynurenine is a potential novel contributor to hypotension in human sepsis." Crit Care Med 39(12): 2678-2683.
Cheng et al. (2015). "Tryptophan derivatives regulate the transcription of Oct4 in stem-like cancer cells." Nat Commun 6: 7209.
Dolwick et al. (1993). "In vitro analysis of Ah receptor domains involved in ligand-activated DNA recognition." Proc Natl Acad Sci U S A 90(18): 8566-8570.
Ema et al. (1994). "Dioxin binding activities of polymorphic forms of mouse and human arylhydrocarbon receptors." J Biol Chem 269(44): 27337-27343.
Esser et al. (2009). "The aryl hydrocarbon receptor in immunity." Trends Immunol 30(9): 447-454.
Goodsell et al. (1996). "Automated docking of flexible ligands: applications of AutoDock." J Mol Recognit 9(1): 1-5.
Han et al. (2004). "Comparison of recombinant cell bioassays for the detection of Ah receptor agonists." Biofactors 20(1): 11-22.
Helferich et al. (1991). "Ultraviolet photoproducts of tryptophan can act as dioxin agonists." Mol Pharmacol 40(5): 674-678.

(Continued)

*Primary Examiner* — Susanna Moore
(74) *Attorney, Agent, or Firm* — Quarles & Brady LLP

(57) ABSTRACT

The present invention relates to novel compounds which are aryl hydrocarbon receptor (AHR) ligands and uses thereof. Methods of activating the AHR receptor in a subject are also provided. The compounds of the present invention include compounds of Formula (I) and Formula (IV):

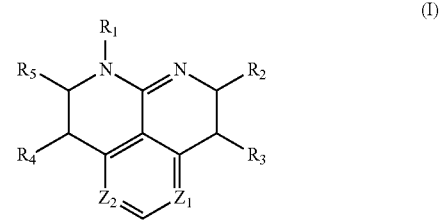

(I)

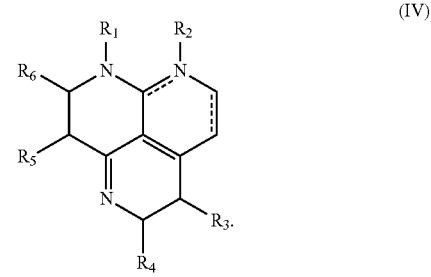

(IV)

21 Claims, 33 Drawing Sheets
(25 of 33 Drawing Sheet(s) Filed in Color)

(56) References Cited

PUBLICATIONS

Hubbard et al. (2015). "Adaptation of the human aryl hydrocarbon receptor to sense microbiota-derived indoles." Sci Rep 5: 12689.
Hubbard et al. (2015). "Indole and Tryptophan Metabolism: Endogenous and Dietary Routes to Ah Receptor Activation." Drug Metab Dispos 43(10): 1522-1535.
Husted et al. (2017). "GPCR-Mediated Signaling of Metabolites." Cell Metab 25(4): 777-796.
Jasiewicz et al. (2016). "Activity of the kynurenine pathway and its interplay with immunity in patients with pulmonary arterial hypertension." Heart 102(3): 230-237.
Jonker et al. (2012). "A PPARgamma-FGF1 axis is required for adaptive adipose remodelling and metabolic homeostasis." Nature 485(7398): 391-394.
Korashy et al. (2006). "The role of aryl hydrocarbon receptor in the pathogenesis of cardiovascular diseases." Drug Metab Rev 38(3): 411-450.
Lamas et al. (2016). "CARD9 impacts colitis by altering gut microbiota metabolism of tryptophan into aryl hydrocarbon receptor ligands." Nat Med 22(6): 598-605.
Leklem (1971). "Quantitative aspects of tryptophan metabolism in humans and other species: a review." Am J Clin Nutr 24(6): 659-672.
Li et al. (2010). "Extensive in vivo metabolite-protein interactions revealed by large-scale systematic analyses." Cell 143(4): 639-650.
McIntosh et al. (2010). "Mammalian Per-Arnt-Sim proteins in environmental adaptation." Annu Rev Physiol 72: 625-645.
Mezrich et al. (2010). "An interaction between kynurenine and the aryl hydrocarbon receptor can generate regulatory T cells." J Immunol 185(6): 3190-3198.
Nguyen et al. (2008). "The search for endogenous activators of the aryl hydrocarbon receptor." Chem Res Toxicol 21(1): 102-116.
Nguyen et al. (2010). "Aryl hydrocarbon receptor negatively regulates dendritic cell immunogenicity via a kynurenine-dependent mechanism." Proc Natl Acad Sci U S A 107(46): 19961-19966.
O'Mahony et al. (2015). "Serotonin, tryptophan metabolism and the brain-gut-microbiome axis." Behav Brain Res 277: 32-48.
Opitz et al. (2011). "An endogenous tumour-promoting ligand of the human aryl hydrocarbon receptor." Nature 478 (7368): 197-203.
Oxenkrug (2010). "Metabolic syndrome, age-associated neuroendocrine disorders, and dysregulation of tryptophan-kynurenine metabolism." Ann N Y Acad Sci 1199: 1-14.
Pandini et al. (2009). "Detection of the TCDD binding-fingerprint within the Ah receptor ligand binding domain by structurally driven mutagenesis and functional analysis." Biochemistry 48(25): 5972-5983.
Poland et al. (1994). "Analysis of the four alleles of the murine aryl hydrocarbon receptor." Mol Pharmacol 46(5): 915-921.
Polyzos et al. (2015). "The role of the kynurenine pathway of tryptophan metabolism in cardiovascular disease. An emerging field." Hamostaseologie 35(2): 128-136.
Procopio et al. (2002). "A model for recognition of polychlorinated dibenzo-p-dioxins by the aryl hydrocarbon receptor." Eur J Biochem 269(1): 13-18.
Rannug et al. (1987). "Certain photooxidized derivatives of tryptophan bind with very high affinity to the Ah receptor and are likely to be endogenous signal substances." J Biol Chem 262(32): 15422-15427.
Rannug et al. (1995). "Structure elucidation of two tryptophan-derived, high affinity Ah receptor ligands." Chem Biol 2(12): 841-845.
Rothhammer et al. (2016). "Type I interferons and microbial metabolites of tryptophan modulate astrocyte activity and central nervous system inflammation via the aryl hydrocarbon receptor." Nat Med 22(6): 586-597.
Rudzite et al. (1991). "Impairment of kynurenine metabolism in cardiovascular disease." Adv Exp Med Biol 294: 663-667.
Santagata et al. (2014). "Intraoperative mass spectrometry mapping of an onco-metabolite to guide brain tumor surgery." Proc Natl Acad Sci U S A 111(30): 11121-11126.
Savouret et al. (2003). "The aryl hydrocarbon receptor and its xenobiotic ligands: a fundamental trigger for cardiovascular diseases." Nutr Metab Cardiovasc Dis 13(2): 104-113.
Schmidt et al. (1996). "Ah receptor signaling pathways." Annu Rev Cell Dev Biol 12: 55-89.
Serhan (2014). "Pro-resolving lipid mediators are leads for resolution physiology." Nature 510(7503): 92-101.
Singh et al. (2016). "Dietary Indoles Suppress Delayed-Type Hypersensitivity by Inducing a Switch from Proinflammatory Th17 Cells to Anti-Inflammatory Regulatory T Cells through Regulation of MicroRNA." J Immunol 196(3): 1108-1122.
Seok et al. (2018). "Trace derivatives of kynrenine potently activate the aryl hydrocarbon receptor (AHR)", J. Biol. Chem 293(6) 1994-2005.
Stevens et al. (2009). "The aryl hydrocarbon receptor: a perspective on potential roles in the immune system." Immunology 127(3): 299-311.
Stone et al. (2002). "Endogenous kynurenines as targets for drug discovery and development." Nat Rev Drug Discov 1(8): 609-620.
Tokuyama et al. (1967). "The photoreduction of kynurenic acid to kynurenine yellow and the occurrence of 3-hydroxy-L-kynurenine in butterflies." J Am Chem Soc 89(4): 1017-1021.
Wei et al. (2000). "Regulation of CYP1A1 transcription via the metabolism of the tryptophan-derived 6-formylindolo[3,2-b]carbazole." Arch Biochem Biophys 383(1): 99-107.
Wei et al. (1998). "Rapid and transient induction of CYP1A1 gene expression in human cells by the tryptophan photoproduct 6-formylindolo[3,2-b]carbazole." Chem Biol Interact 110(1-2): 39-55.
Xing et al. (2012). "Identification of the Ah-receptor structural determinants for ligand preferences." Toxicol Sci.
Yore et al. (2014). "Discovery of a class of endogenous mammalian lipids with anti-diabetic and anti-inflammatory effects." Cell 159(2): 318-332.
Zelante et al. (2013). "Tryptophan catabolites from microbiota engage aryl hydrocarbon receptor and balance mucosal reactivity via interleukin-22." Immunity 39(2): 372-385.
Zelentsova et al. (2013). "Photochemistry of aqueous solutions of kynurenic acid and kynurenine yellow." Photochem Photobiol Sci 12(3): 546-558.

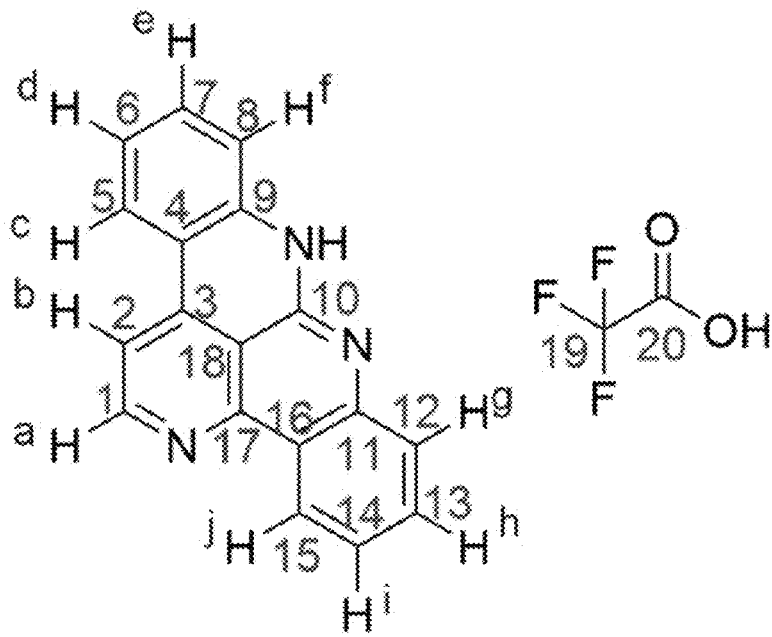

| Chemical Shift | Proton(s) |
| --- | --- |
| 9.34 (d, $J$ = 6.0 Hz, 1H) | H$^a$ |
| 8.88 (d, $J$ = 8.0 Hz, 1H) | H$^j$ |
| 8.40 (d, $J$ = 8.0 Hz, 1H) | H$^c$ |
| 8.28 (d, $J$ = 6.0 Hz, 1H) | H$^b$ |
| 7.92-7.88 (m, 4H) | H$^e$, H$^f$, H$^g$, H$^h$ |
| 7.70-7.64 (m, 2H) | H$^d$ (around 7.65), H$^i$ (around 7.70) |

Assignment of all the protons of the synthesized Compound 4 TFA salt.

| Carbon | Chemical Shift | Carbon | Chemical Shift | Carbon | Chemical Shift |
| --- | --- | --- | --- | --- | --- |
| C1 | 152.0 | C8 | 119.8 | C15 | 125.3 |
| C2 | 114.1 | C9 | 136.5 | C16 | 118.1 |
| C3 | 143.8 | C10 | 146.5 | C17 | 150.3 |
| C4 | 116.9 | C11 | 136.8 | C18 | 111.1 |
| C5 | 124.6 | C12 | 119.3 | C19 | 115.3 (q, $J$ = 286.8 Hz) |
| C6 | 126.7 | C13 | 135.0 | C20 | 160.8 (q, $J$ = 40.6 Hz) |
| C7 | 135.4 | C14 | 127.0 | | |

Assignment of all the carbons of the synthesized Compound 4 TFA salt.

FIG. 17

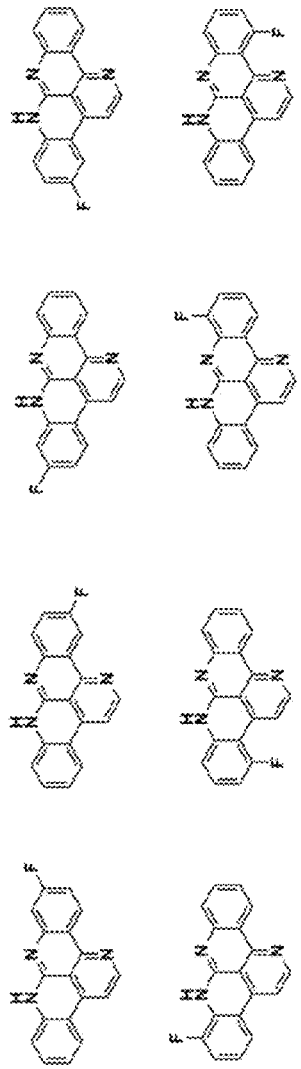
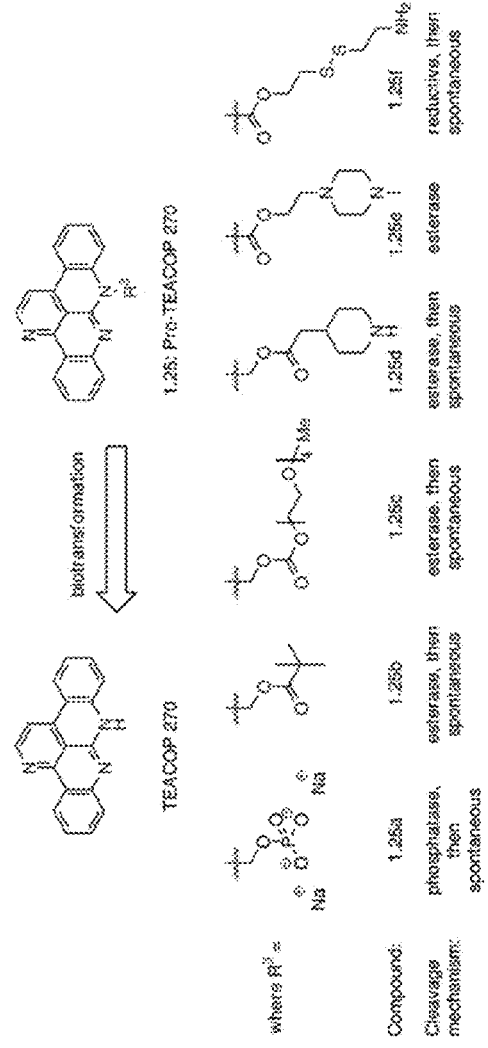
FIG. 28 (continued)

| compounds | Molecular Formula | Free M.W. (g/mol) | LogD | Microsome Stability | | | Plasma Stability | | |
|---|---|---|---|---|---|---|---|---|---|
| | | | | % remaining @ 1 hr | | | % remaining @ 3 hrs | | |
| | | | LogD(7.4) | Human | Mouse | Rat | Human | Mouse | Rat |
| TEACOP270 | C18H11N3 | 269.31 | 3.71 | 8.4 | 21.8 | | 60.9 | 63.1 | |
| TEACOP270 TFA salt | C24H14F9N3O6 | 611.38 | 3.62 | 15.7 | 9.9 | | 60.0 | 60.6 | |

Summary Data for MicroAmes Screen without Metabolic Activation
(Mean of Duplicate Wells)

| Without S9 Activation | | | | | | |
|---|---|---|---|---|---|---|
| | Conc. (μg/well) | TA97a[a] | TA98[a] | TA100[a] | TA1535[a] | WP2uvrA pKM101[a] |
| DMSO | 3.5 μL | 12 | 2 | 11 | 4 | 12 |
| Positive Control<br><br>ICR:TA97a<br><br>NQNO: TA98, TA100 & WP2uvrA pKM101<br><br>SA: TA1535 | $5.0 \times 10^{-4}$ | 15 | 2 | 11 | 8 | 11 |
| | $5.0 \times 10^{-3}$ | 15 | 3 | 18 | 16* | 10 |
| | $5.0 \times 10^{-2}$ | 48* | 28* | >60* | >60* | >60* |
| | $5.0 \times 10^{-1}$ | >60* | 22* | 49* | >60* | >60* |
| TEACOP 270 | 7.8 | 13 | 2 | 11 | 3 | 10 |
| | 15.5[b] | 15 | 2 | 13 | 5 | 13 |
| | 31[b] | 14 | 3 | 13 | 10 | 11 |
| | 62.5[b] | 13 | 4 | 12 | 8 | 13 |
| | 125[b] | 14 | 2 | 10 | 9 | 10 |
| | 250[b] | 12 | 2 | 10 | 3 | 10 |

NQNO – 4-Nitroquinoline-N-oxide; ICR – ICR-191 Acridine; SA – Sodium azide
DMSO – Dimethylsulfoxide

[a] Mean revertant colonies from duplicate wells (for DMSO controls, means are from 12 wells)
[b] Precipitates present \* Indicates > 6 revertant colonies and an increase over vehicle mean by 2-fold for TA97a, TA100, and WP2 uvrA pKM101 and 3-fold for TA98 and TA1535

FIG. 34

ARYL HYDROCARBON RECEPTOR LIGANDS FROM KYNURENINE

CROSS-REFERENCE TO RELATED APPLICATIONS

This application claims priority to U.S. Provisional Application No. 62/583,903 filed on Nov. 9, 2017, the contents of which are incorporated by reference in its entirety.

STATEMENT REGARDING FEDERALLY SPONSORED RESEARCH

This invention was made with government support under GM096060 awarded by the National Institutes of Health. The government has certain rights in the invention.

BACKGROUND OF THE INVENTION

The field of the invention is aryl hydrocarbon receptor (AHR) ligands and their use.

Kynurenine is a tryptophan metabolite generated by the enzymes indoleamine 2,3-dioxygenase (IDO) and tryptophan 2,3,-dioxygenase (TDO). The cellular levels of kynurenine and its downstream metabolites play crucial roles in regulating the immune system, vascular biology and neurological function (Rudzite, Sileniece et al. 1991, Stone and Darlington 2002, Polyzos and Ketelhuth 2015, Jasiewicz, Moniuszko et al. 2016). Disorders of kynurenine metabolism are associated with a variety of human health issues including cancer, hypertension, chronic inflammation, and neurodegenerative disorders (Stone and Darlington 2002, Oxenkrug 2010, Changsirivathanathamrong, Wang et al. 2011). A number of recent studies have suggested a link between the physiological effects of kynurenine and the aryl hydrocarbon receptor (AHR) (Mezrich, Fechner et al. 2010, Bessede, Gargaro et al. 2014). The AHR is a PAS (PER, ARNT, SIM) family transcriptional factor that is essential for development and normal function of vascular and immune systems (Savouret, Berdeaux et al. 2003, Korashy and El-Kadi 2006, Esser, Rannug et al. 2009, Stevens, Mezrich et al. 2009). In support of this relationship are the numerous observation that kynurenine levels influence a variety of immune responses in an AHR dependent manner (Opitz, Litzenburger et al. 2011, Mezrich, Fechner et al. 2010, Nguyen, Kimura et al. 2010). The underlying mechanistic role of the AHR in kynurenine action is currently uncertain. Although it has been shown that kynurenine is a receptor activator, its structure does not conform to many of the rules that correlate with high affinity binding to the AHR (Fig. s1) (Procopio, Lahm et al. 2002, Bisson, Koch et al. 2009, Pandini, Soshilov et al. 2009, Xing, Nukaya et al. 2012).

Like kynurenine, many cellular metabolites that activate the AHR are derived from tryptophan. For example, exposure to UV radiation in the skin converts tryptophan to 6-formylindolo [3,2-b] carbazole (FICZ) (Rannug, Rannug et al. 1987, Helferich and Denison 1991, Rannug, Rannug et al. 1995), stomach acid converts dietary indole-3-carbinol to indolo [3,3b] carbazole (ICZ), the enzyme d-amino acid oxidase (DAAO) converts tryptophan to indole 3-pyruvic acid, and gut microbiota generate tryptophan derived AHR activators that are crucial for curtailing inflammatory bowel disease and central nervous system inflammation (Zelante, Iannitti et al. 2013, Hubbard, Murray et al. 2015, Lamas, Richard et al. 2016, Rothhammer, Mascanfroni et al. 2016). In addition to endogenous ligands, the AHR also responds to numerous xenobiotic ligands to influence a wide variety of toxicological, immunological, and cardiovascular endpoints (McIntosh, Hogenesch et al. 2010). Knowledge of AHR pharmacology has arisen from studying xenobiotic agonists like the halogenated dibenzo-p-dioxins (e.g. 2,3,7,8-tetrachlorodibenzo-p-dioxin, TCDD), and polycyclic aromatic hydrocarbons (e.g. benzo[a]pyrene, BaP) (Procopio, Lahm et al. 2002, Bisson, Koch et al. 2009, Pandini, Soshilov et al. 2009, Xing, Nukaya et al. 2012). These studies show that AHR prefers elongated planar compounds with large lateral extension and small medial extension with specific medial H-bond potential (FIG. 6). Thousands of xenobiotic compounds and cellular metabolites with diverse shape and chemical properties have been reported to bind AHR (Schmidt and Bradfield 1996, Nguyen and Bradfield 2008). While a majority of AHR ligands have an overall elongated planar shape, some ligands barely have any AHR ligand structural signatures. Kynurenine is one such ligand that is much smaller, polar, and irregular in shape (FIG. 6). Using homology models of AHR-LBD bound to TCDD and BaP, we previously identified key structural signatures for AHR-binding that differentially affect the efficacy of different ligands, and flexible structural elements that are essential for tolerating diverse ligands (Xing, Nukaya et al. 2012). A flexible extended loop of AHR, named "belt", is longer and more flexible than other PAS family transcription factors, underlying the unique ability of AHR to respond to diverse ligands.

There is a need in the art to further understand what molecules play a part in AHR binding and signaling and the identification of novel compounds that can activate the AHR pathway.

SUMMARY OF THE INVENTION

The present invention provides compounds which are novel ligands that bind to and activate the AHR in picomolar amounts. Further, the present invention provides methods and kits for use of the compounds described herein.

In one aspect, the present disclosure provides a compound of formula (I):

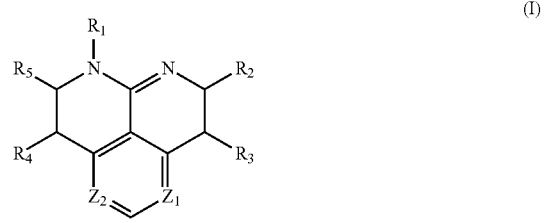

or a pharmaceutically acceptable salt and individual diasteromers thereof, wherein $Z_1$ and $Z_2$ are each independently selected from nitrogen or —CH;

$R_1$ being selected from hydrogen and unsubstituted or substituted $C_{1-3}$ alkyl, where the alkyl is substituted with 1-2 constituents selected from hydroxy, halo, phenyl, and heterocyclic moieties;

$R_2$ and $R_3$ are joined together to form a first ring, the first ring being selected from substituted or unsubstituted cycloalkane, substituted or unsubstituted benzene, and substituted or unsubstituted heterocycle; and $R_4$ and $R_5$ are joined together to form a second ring, the second ring being selected from a substituted or unsubstituted cycloalkane, a substituted or unsubstituted benzene, and a substituted or unsubstituted heterocycle.

In another aspect, the compound is:

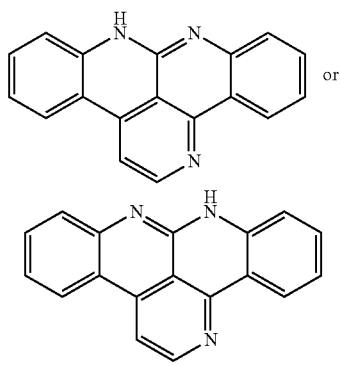

or

In a further aspect, the disclosure provides a compound of formula (II):

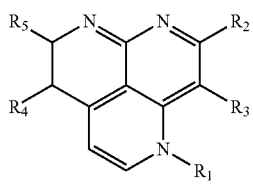

(II)

or a pharmaceutically acceptable salt and individual diasteromers thereof, wherein $R_1$ being selected from hydrogen and unsubstituted or substituted $C_{1-3}$ alkyl, where the alkyl is substituted with 1-2 constituents selected from hydroxy, halo, phenyl, and heterocyclic moieties;

$R_2$ and $R_3$ are joined together to form a first ring, the first ring being selected from substituted or unsubstituted cycloalkane, substituted or unsubstituted benzene, and substituted or unsubstituted heterocycle; and $R_4$ and $R_5$ are joined together to form a second ring, the second ring being selected from a substituted or unsubstituted cycloalkane, a substituted or unsubstituted benzene, and a substituted or unsubstituted heterocycle.

In yet another aspect, the disclosure provides a compound of formula (III):

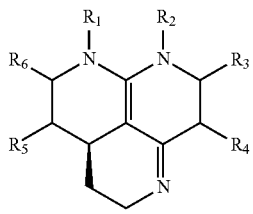

(III)

or a pharmaceutically acceptable salt and individual diasteromers thereof, wherein $R_1$ and $R_2$ are each individually selected from hydrogen and unsubstituted or substituted $C_{1-3}$ alkyl, where the alkyl is substituted with 1-2 constituents selected from hydroxy, halo, phenyl, and heterocyclic moieties;

$R_3$ and $R_4$ are joined together to form a first ring, the first ring being selected from substituted or unsubstituted cycloalkane, substituted or unsubstituted benzene, and substituted or unsubstituted heterocycle; and $R_5$ and $R_6$ are joined together to form a second ring, the second ring being selected from a substituted or unsubstituted cycloalkane, a substituted or unsubstituted benzene, and a substituted or unsubstituted heterocycle.

In yet another aspect, the disclosure provides a compound of formula (IV)

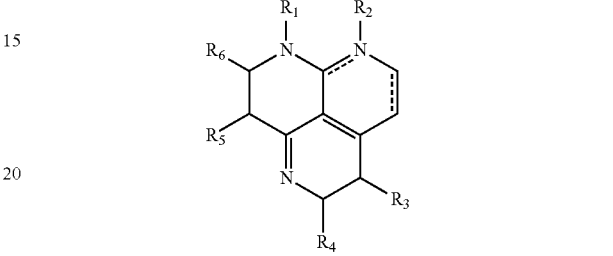

(IV)

or a pharmaceutically acceptable salt and individual diasteromers thereof, wherein $R_1$ being selected from hydrogen and unsubstituted or substituted $C_{1-3}$ alkyl, where the alkyl is substituted with 1-2 constituents selected from hydroxy, halo, phenyl, and heterocyclic moieties;

$R_2$ being selected from hydrogen, unsubstituted or substituted $C_{1-3}$ alkyl, and nothing, where the alkyl is substituted with 1-2 constituents selected from hydroxy, halo, phenyl, and heterocyclic moieties $R_3$ and $R_4$ are joined together to form a first ring, the first ring being selected from substituted or unsubstituted cycloalkane, substituted or unsubstituted benzene, and substituted or unsubstituted heterocycle; and $R_5$ and $R_6$ are joined together to form a second ring, the second ring being selected from a substituted or unsubstituted cycloalkane, a substituted or unsubstituted benzene, and a substituted or unsubstituted heterocycle; and wherein the dotted line represents an optional covalent bond.

In yet another aspect, the disclosure provides a method of activating the AHR receptor in a subject, the method comprising administering an effected amount of the compounds described herein.

In yet another aspect, the disclosure provides method treating a subject having a kynurenine disorder, the method comprising administering an effected amount of the compounds described herein, wherein the kynurenine disorder is treated.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 10A-10B show that known chemical derivatives of kynurenine did not induce AHR transcriptional activity as kynurenine. (a) Known chemical conversions and derivatives of L-kynurenine. (b) Dose-dependent response curves of the transcriptional activity of WT mAHR to kynurenine, kynurenic acid, and 4-hydroxyquinoline, determined as in FIG. 1a.

FIG. 17 shows assignment of NMR signals for all protons and carbons for the synthesized Compound 4 based on NMR spectra below (FIGS. 18-23).

FIG. 34 shows the results of AMES test on TEACOP270. No mutagenicity is detected.

DETAILED DESCRIPTION OF THE INVENTION

Figures 1A, 1B, 1C, 1D, 1E:
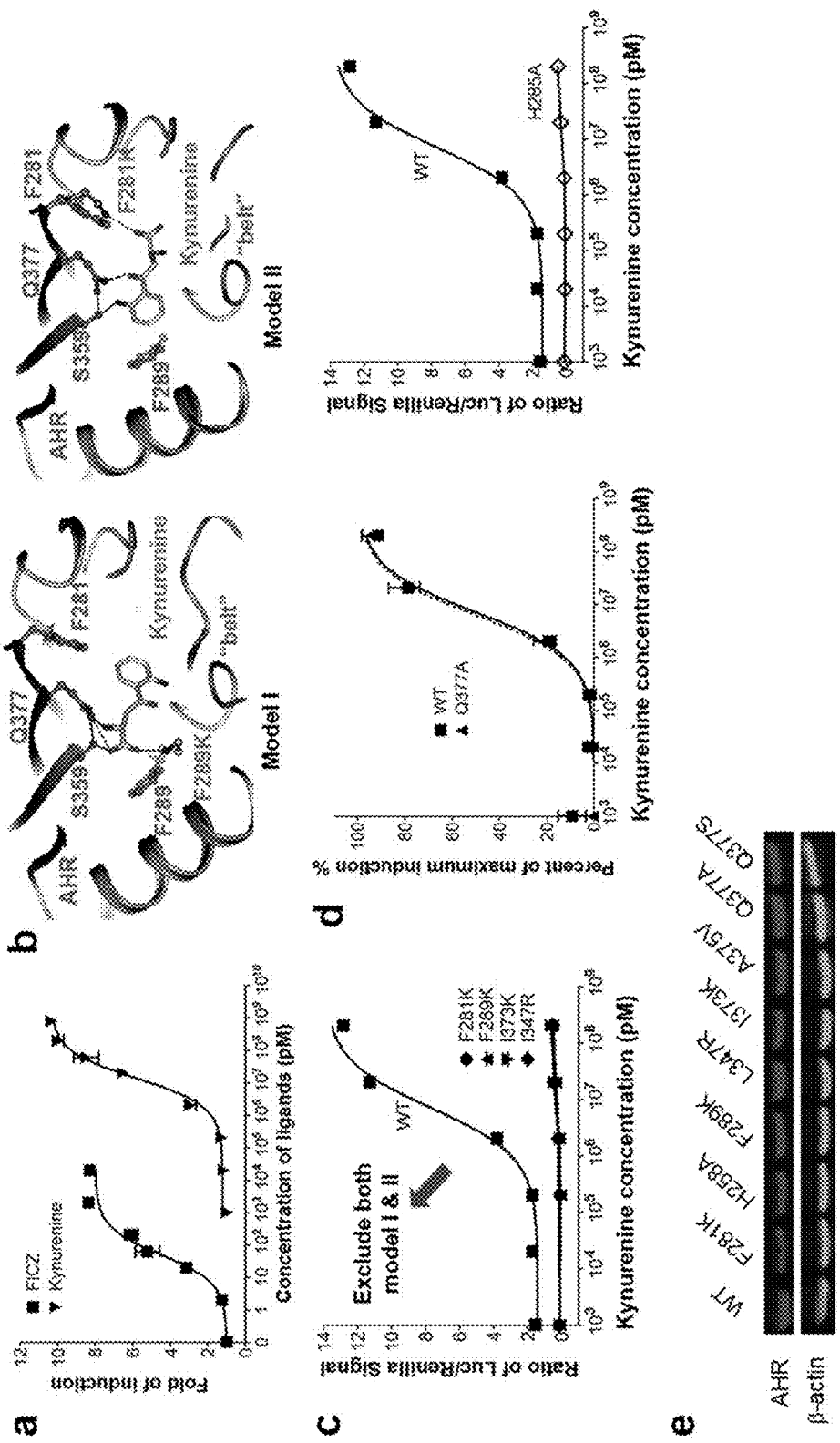
FIGS. 1A-1E demonstrates kynurenine has low in vitro efficacy and models of AHR binding contradict predicted structural signatures. (a) Dose-dependent response curves of AHR ligands, FICZ and kynurenine, in induction of the transcriptional activity of mAHR. The induction level of the AHR activity was measured by reporter luciferase activity and normalized to the signal of renilla luciferase. (b) Two hypothetical structural models of kynurenine bound to AHR ligand-binding pocket. Key residues of AHR is shown in ball-and-stick and colored by atom type. Intermolecular H-bonds are in black dashed line. Kynurenine is in stick and colored green and by atom type. (c) Dose-dependent response curves of WT and mutant AHR, F289K, F281K, I373K, and L347R, to kynurenine, determined as in FIG. 1a. (d) Dose-dependent response curves of kynurenine in activation of WT and mutant AHR bearing mutation to the residue with medial H-bond potential, Q377A (left), or the residue that forms part of H-bond network lining the ligand-binding pocket, H285A. The level of AHR activity was normalized to the maximum induction or to the signal of renilla luciferase. (e) The expression level of WT and mutant mAHR in COS-1 cells was examined by western blot. β-actin was detected as loading control.

The present invention relates to novel aryl hyrdrocarbon receptor ligands and methods of use. The inventors purified trace active derivatives of kynurenine and identified two novel, closely-related condensation products, named as TEACOPs (trace extended aromatic condensation products), which are active at low picomolar levels. The synthesized compound for one of the predicted structures matches the purified compound in both chemical structure and AHR pharmacology. Further, the inventors have provided derivatives of said TEACOPS that are able to activate the AHR receptor, some of which are found in FIGS. 28 and 29 and in the formulas described below. Further, the present invention provides compounds that activate the aryl hydrocarbon receptor as depicted in formulas (I)-(VI). These compounds can be used in the methods and kits as described herein.

In one aspect, the present invention provides a compound of formula (I):

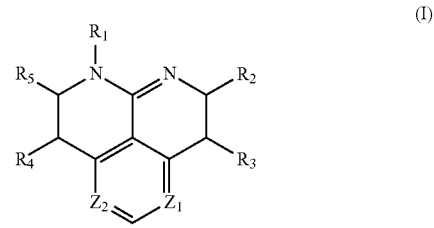

(I)

or a pharmaceutically acceptable salt and individual diasteromers thereof, wherein $Z_1$ and $Z_2$ are each independently selected from nitrogen or —CH;

$R_1$ being selected from hydrogen and unsubstituted or substituted $C_{1-3}$ alkyl, where the alkyl is substituted with 1-2 constituents selected from hydroxy, halo, phenyl, and heterocyclic moieties;

$R_2$ and $R_3$ are joined together to form a first ring, the first ring being selected from substituted or unsubstituted cycloalkane, substituted or unsubstituted benzene, and substituted or unsubstituted heterocycle; and $R_4$ and $R_5$ are joined together to form a second ring, the second ring being selected from a substituted or unsubstituted cycloalkane, a substituted or unsubstituted benzene, and a substituted or unsubstituted heterocycle.

In some embodiments, the compound of formula (I) comprises first ring and the second ring are unsubstituted benzene. In further embodiments, the first ring or the second ring is substituted benzene with one or more constituents selected from hydroxyl, halo, $C_{1-3}$ alkyl, $C_{1-3}$ alkenyl, $C_{1-3}$-alkynyl, —O—$C_{1-3}$ alkyl, wherein the alkyl is unsubstituted or substituted with constituents selected from hydroxy, chloro and trifluoromethyl.

In some embodiments, the compound of formula (I) comprises the first ring, the second ring, or both are unsubstituted or substituted heterocycle with one or more constituents selected from hydroxyl, halo, $C_{1-3}$ alkyl, $C_{1-3}$ alkenyl, $C_{1-3}$-alkynyl, —O—$C_{1-3}$ alkyl, wherein the alkyl is unsubstituted or substituted with constituents selected from hydroxy, chloro and trifluoromethyl.

In some embodiments, the compound of formula (I) is:

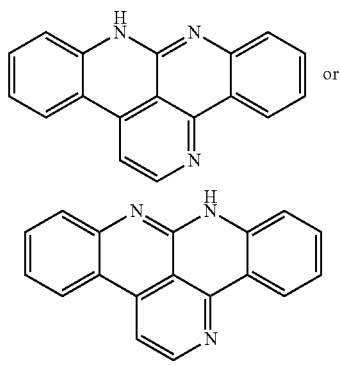

or

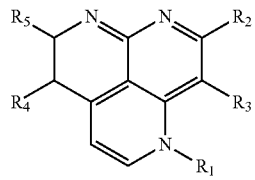

In another embodiment, the compound of the present invention comprises formula (II):

(II)

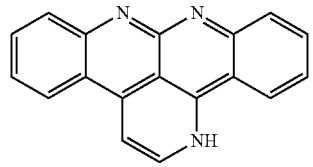 [SMILES: C1=Cc2c3ccccc3nc3nc4ccccc4c(c23)N1]

or a pharmaceutically acceptable salt and individual diasteromers thereof, wherein $R_1$ being selected from hydrogen and unsubstituted or substituted $C_{1-3}$ alkyl, where the alkyl is substituted with 1-2 constituents selected from hydroxy, halo, phenyl, and heterocyclic moieties;

$R_2$ and $R_3$ are joined together to form a first ring, the first ring being selected from substituted or unsubstituted cycloalkane, substituted or unsubstituted benzene, and substituted or unsubstituted heterocycle; and $R_4$ and $R_5$ are joined together to form a second ring, the second ring being selected from a substituted or unsubstituted cycloalkane, a substituted or unsubstituted benzene, and a substituted or unsubstituted heterocycle.

In some embodiments, the compound of formula (II) comprises the first ring and the second ring are unsubstituted benzene. In another embodiment of formula (II), the first ring or the second ring is substituted benzene with one or more constituents selected from hydroxyl, halo, methoxy, $C_{1-3}$ alkyl, $C_{1-3}$ alkenyl, $C_{1-3}$-alkynyl, —O—$C_{1-3}$ alkyl, wherein the alkyl is unsubstituted or substituted with constituents selected from hydroxy, chloro and trifluoromethyl.

In another embodiment, the compound of formula (II) comprises the first ring or the second ring is unsubstituted or substituted heterocycle with one or more constituents selected from hydroxyl, halo, $C_{1-3}$ alkyl, $C_{1-3}$ alkenyl, $C_{1-3}$-alkynyl, —O—$C_{1-3}$ alkyl, wherein the alkyl is unsubstituted or substituted with constituents selected from hydroxy, chloro and trifluoromethyl.

In another embodiment, the compound of formula (II) is

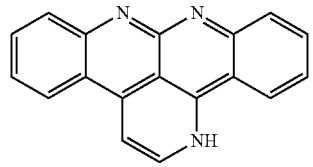 [SMILES: C1=Cc2c3ccccc3nc3nc4ccccc4c(c23)N1]

In some embodiments, the compound of the present invention is selected from the group consisting of

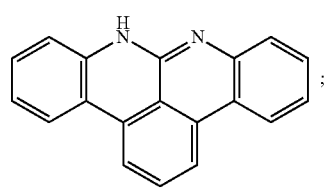

TEACOP269

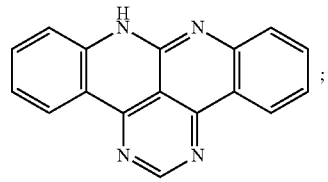

TEACOP271

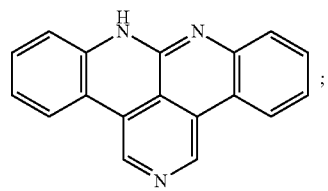

isoTEACOP270

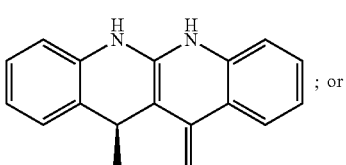

; or

TEACOP273

-continued

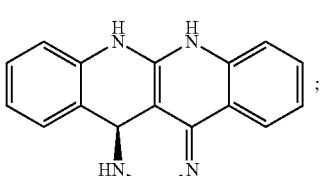
TEACOP275

In another embodiment, the compound of the present invention may be selected from:

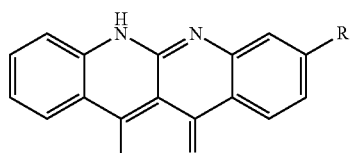

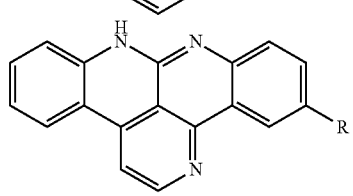

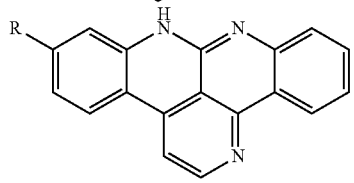

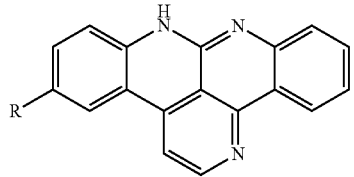

wherein R is selected from the group consisting of:

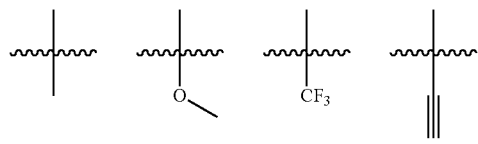

In another embodiment, the compound of the present invention is of formula

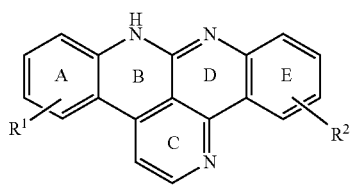

wherein $R^1$ and $R^2$ are independently selected from H or F.

Suitable compounds include, for example, fluoride derivatives, including, but not limited to, for example,

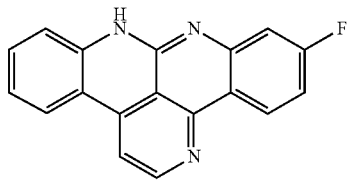

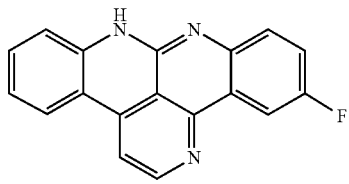

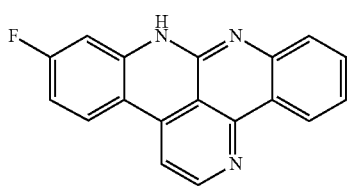

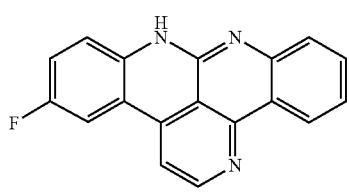

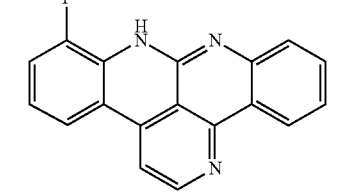

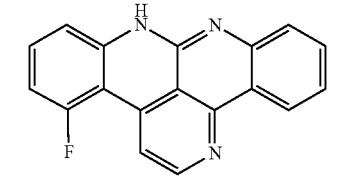

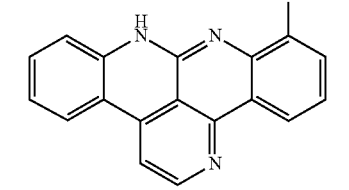

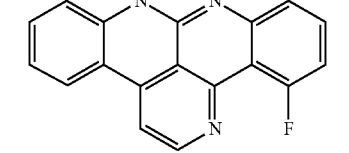

In another embodiment, the compound of the present invention comprises formula (III):

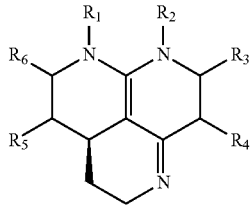

(III)

or a pharmaceutically acceptable salt and individual diasteromers thereof, wherein $R_1$ and $R_2$ are each individually selected from hydrogen and unsubstituted or substituted $C_{1-3}$ alkyl, where the alkyl is substituted with 1-2 constituents selected from hydroxy, halo, phenyl, and heterocyclic moieties;

$R_3$ and $R_4$ are joined together to form a first ring, the first ring being selected from substituted or unsubstituted cycloalkane, substituted or unsubstituted benzene, and substituted or unsubstituted heterocycle; and $R_5$ and $R_6$ are joined together to form a second ring, the second ring being selected from a substituted or unsubstituted cycloalkane, a substituted or unsubstituted benzene, and a substituted or unsubstituted heterocycle.

In some embodiments, the compound of formula (III) comprises the first ring and the second ring are unsubstituted benzene. In another embodiment, the compound of formula (III) comprises the first ring or the second ring is substituted benzene with one or more constituents selected from hydroxyl, halo, methoxy, $C_{1-3}$ alkyl, $C_{1-3}$ alkenyl, $C_{1-3}$-alkynyl, —O—$C_{1-3}$ alkyl, wherein the alkyl is unsubstituted or substituted with constituents selected from hydroxy, methoxy (—OCH$_3$), chloro and trifluoromethyl. In another embodiment, the compound of formula (III) comprises the first ring or the second ring is unsubstituted or substituted heterocycle with one or more constituents selected from hydroxyl, halo, $C_{1-3}$ alkyl, $C_{1-3}$ alkenyl, $C_{1-3}$-alkynyl, —O—$C_{1-3}$ alkyl, methoxy, wherein the alkyl is unsubstituted or substituted with constituents selected from hydroxy, methoxy, chloro and trifluoromethyl.

In yet another embodiment, the compound of formula (III) is

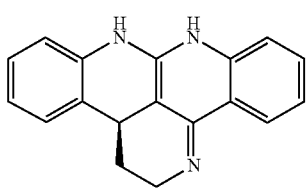 [SMILES: c1ccc2c(c1)NC1=C3C2=NCC[C@H]3c2ccccc2N1]

In further embodiments, the compound of the present invention is one of the following:

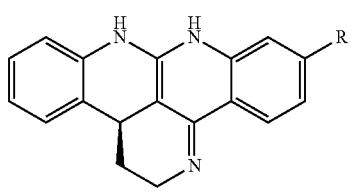

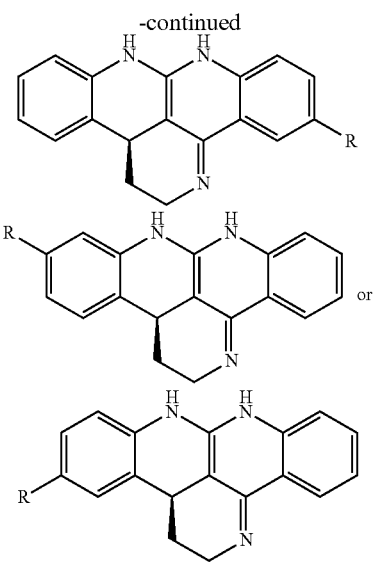

wherein R is selected from the group consisting of:

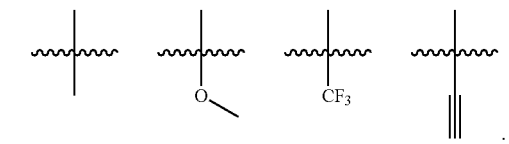

In another embodiment, the present invention provides a compound of formula (IV)

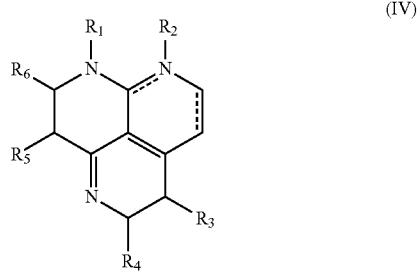

(IV)

or a pharmaceutically acceptable salt and individual diasteromers thereof, wherein $R_1$ being selected from hydrogen and unsubstituted or substituted $C_{1-3}$ alkyl, where the alkyl is substituted with 1-2 constituents selected from hydroxy, halo, phenyl, and heterocyclic moieties;

$R_2$ being selected from hydrogen, unsubstituted or substituted $C_{1-3}$ alkyl, and nothing, where the alkyl is substituted with 1-2 constituents selected from hydroxy, halo, phenyl, and heterocyclic moieties $R_3$ and $R_4$ are joined together to form a first ring, the first ring being selected from substituted or unsubstituted cycloalkane, substituted or unsubstituted benzene, and substituted or unsubstituted heterocycle; and $R_5$ and $R_6$ are joined together to form a second ring, the second ring being selected from a substituted or unsubstituted cycloalkane, a substituted or unsubstituted benzene, and a substituted or unsubstituted heterocycle; and wherein the dotted line represents an optional covalent bond.

In one embodiment, the compound of formula (IV) the first ring and the second ring are unsubstituted benzene. In other embodiments, the first ring or the second ring of formula (IV) is substituted benzene with one or more constituents selected from hydroxyl, halo, $C_{1-3}$ alkyl, $C_{1-3}$-alkenyl, $C_{1-3}$-alkynyl, —O—$C_{1-3}$ alkyl, wherein the alkyl is unsubstituted or substituted with constituents selected from hydroxy, chloro and trifluoromethyl.

In another embodiment, the compound of formula (IV) comprises the first ring or the second ring is unsubstituted or substituted heterocycle with one or more constituents selected from hydroxyl, halo, $C_{1-3}$ alkyl, $C_{1-3}$ alkenyl, $C_{1-3}$-alkynyl, —O—$C_{1-3}$ alkyl, wherein the alkyl is unsubstituted or substituted with constituents selected from hydroxymethyl and trifluoro.

In one embodiment, the compound of formula (IV) comprises the first ring and the second ring as unsubstituted cyclohexa-1,3-diene. In another embodiment, the compound of formula (IV) as the first ring or the second ring as a substituted cyclohexa-1,3-diene with one or more constituents selected from hydroxyl, halo, $C_{1-3}$ alkyl, $C_{1-3}$ alkenyl, $C_{1-3}$-alkynyl, —O—$C_{1-3}$ alkyl, wherein the alkyl is unsubstituted or substituted with constituents selected from hydroxy, chloro and trifluoromethyl. In another embodiment, formula (IV) comprises the first ring or the second ring as unsubstituted or substituted heterocycle with one or more constituents selected from hydroxyl, halo, $C_{1-3}$ alkyl, $C_{1-3}$ alkenyl, $C_{1-3}$-alkynyl, —O—$C_{1-3}$ alkyl, wherein the alkyl is unsubstituted or substituted with constituents selected from hydroxy, chloro and trifluoromethyl. In a further embodiment, the first ring or the second ring is unsubstituted or substituted heterocycle with one or more constituents selected from hydroxyl, halo, C1-3 alkyl, C1-3 alkenyl, C1-3-alkynyl, —O—C1-3 alkyl, wherein the alkyl is unsubstituted or substituted with constituents selected from hydroxy, chloro and trifluoro.

Prodrugs

In some embodiments, the compounds of the present invention include prodrugs that can be converted to an active form by cleavage at a target pH and/or using enzymes such as, but not limited to, phosphatase, esterase, among others. The term "prodrug" refers to an inactive compound which is metabolized within the body to form the pharmacologically active compound. Prodrugs may be administered to improve how the compound is absorbed, distributed, metabolized or excreted within the subject being treated. Prodrugs may improve the bioavailability of the drug or improve how selectively the drug interacts with cells or processes that are not the intended target by reducing adverse or unintended effects of the compound.

The present invention also provides prodrugs of the compounds (I)-(V) described herein.

In one embodiment, the present invention provides representative scenarios of prodrugs with formula (V):

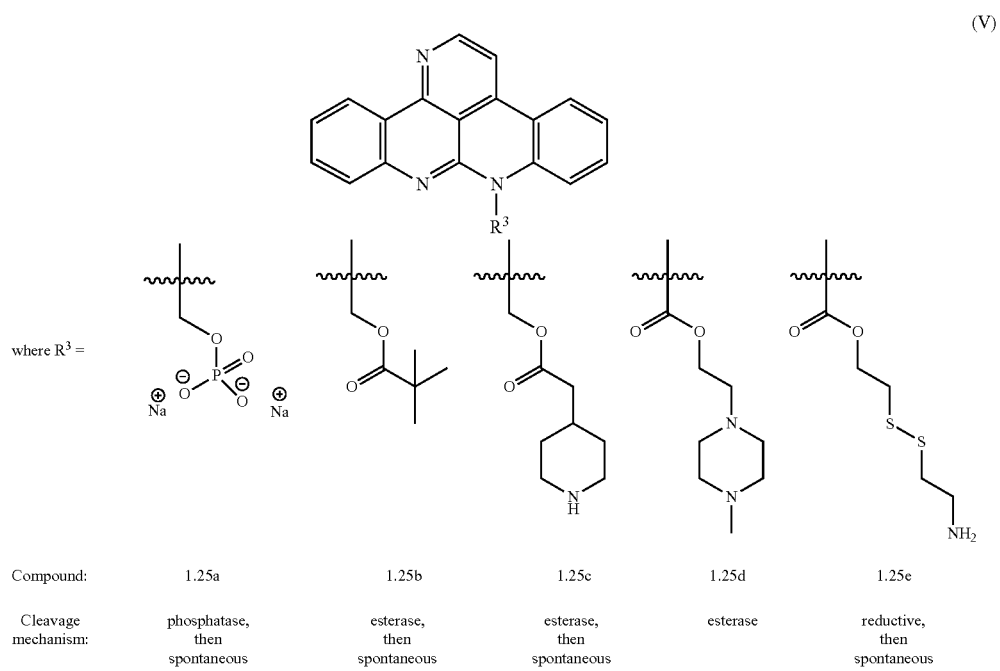

Similar prodrugs can be made with compounds (I)-(IV) described herein instead of (V) by one skilled in the art. Methods of producing prodrugs are known in the art. For example, as detailed in FIG. 32, methods of producing a few exemplary prodrugs of the present invention are provided.

It is contemplated that the prodrugs and compositions comprising the prodrugs described herein can be formulated into and administered by a variety of dosage forms, for example, oral routes of delivery. Once administered, the prodrugs will release the active compound under various bioconversion conditions.

The compounds described above may be used in one or more methods described herein.

The compounds herein can be included in a pharmaceutical composition or preparation that is able to be administered to a subject in need thereof. The pharmaceutical composition may contain one or more pharmaceutically acceptable carriers.

The pharmaceutical compositions may further include a pharmaceutically acceptable carrier. The term "pharmaceutically acceptable carrier" refers any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences*, 18th Ed., (1990) Mack Publishing Co., Easton, Pa. Suitable dosage forms may comprise, for example, tablets, capsules, solutions, parenteral solutions, troches, suppositories, or suspensions.

For oral administration, the active agent may be combined with one or more solid inactive ingredients for the preparation of tablets, e capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. Additional oral administration forms are contemplated, including, but not limited to, elixirs, liquids, solutions, suspensions, emulsions, multi-layer tablets, soft gelatin capsules, hard gelatin capsules, troches, lozenges, beads, granules, particles, microparticles, dispensible granules, cachets, among others. Formulations of the present technology suitable for oral administration can be presented as discrete units, such as capsules, caplets or tablets. These oral formulations also can comprise a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which can then be placed in the feeding tube of a patient who is unable to swallow.

For parenteral administration, the active agent may be mixed with a suitable carrier or diluent such as water, an oil (e.g., a vegetable oil), ethanol, saline solution (e, g., phosphate buffer saline or saline), aqueous dextrose (glucose) and related sugar solutions, glycerol, or a glycol such as propylene glycol or polyethylene glycol. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or nonaqueous solution, dispersion, suspension or emulsion.

The pharmaceutical composition is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, intradermal administration, intrathecal administration and subcutaneous administration. Administration can be continuous or intermittent. In various aspects, a preparation can be administered therapeutically; that is, administered to treat an existing disease or condition. In a preferred embodiment, the administration is intravenous administration or oral administration.

Figure 28:
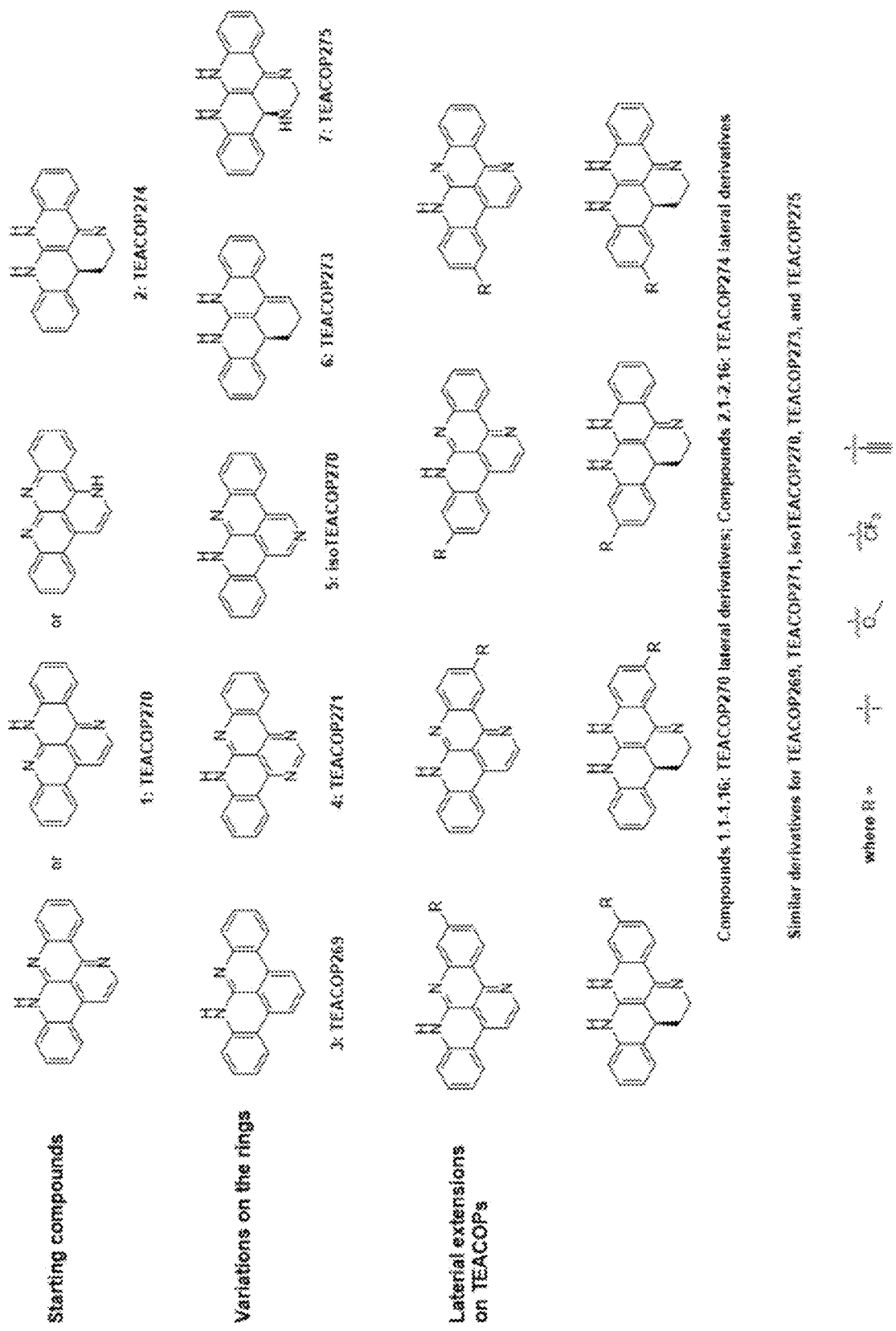
FIG. 28 shows collections of TEACOPs, including ring modifications, lateral extensions, fluoride derivatives and prodrugs.
Figure 29:
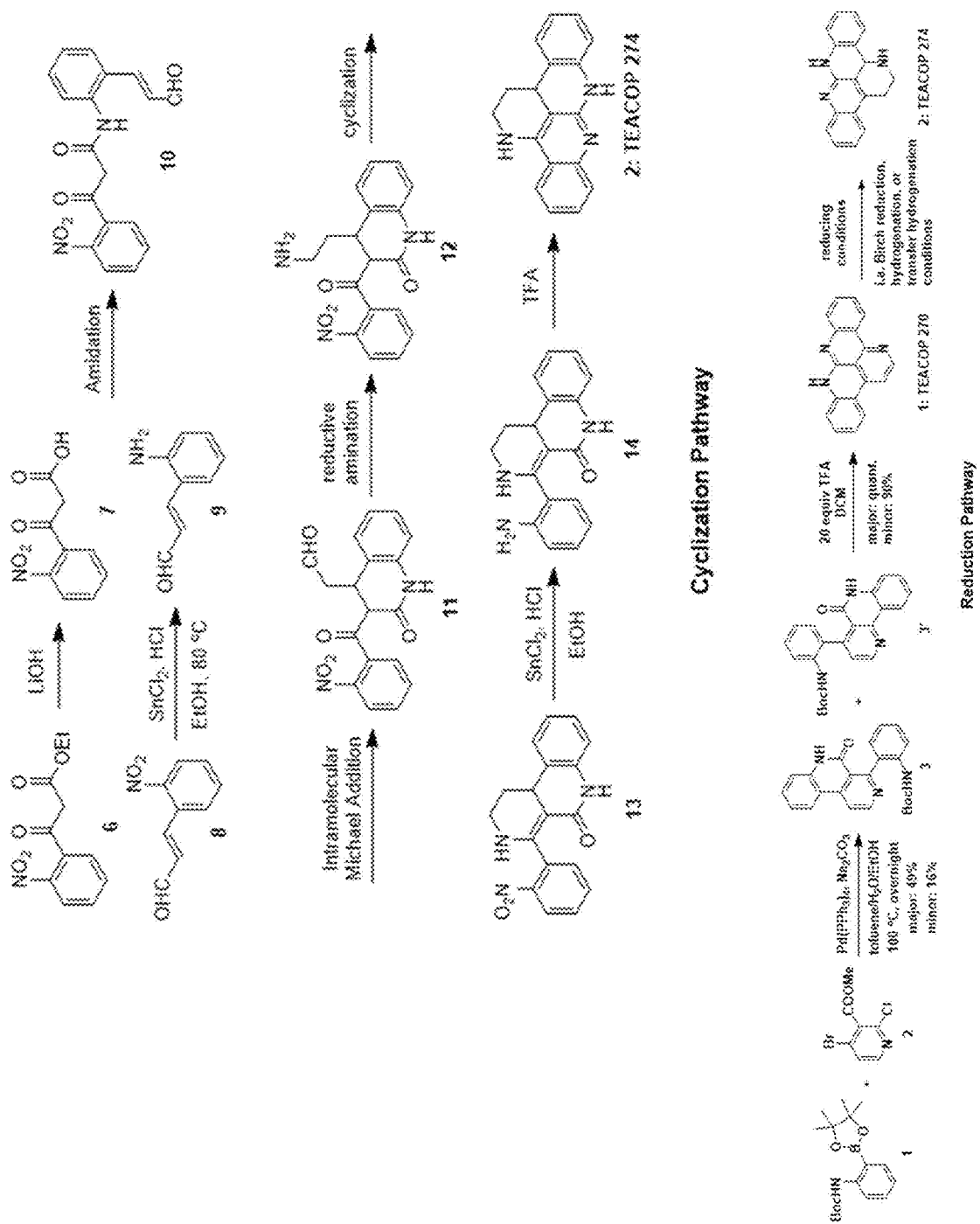
FIG. 29 shows two synthesis schemes of TEACOP274.

In one embodiment, the compounds of the present invention may be used in a method of activating the AHR receptor, the method comprising administering an effected amount compounds of any one of formula (I)-(IV) or any one of the compounds found in FIG. 28 or 29 or prodrugs of formula (V). The compounds described herein are able to activate the AHR receptor in picomolar amounts as compared with kynurenine. In some embodiments, the compounds described herein have at least 1000-fold increase in AHR induction activity as compared with fresh kynurenine.

In some embodiments, the AHR receptor is activated in vivo or in vitro. In some embodiments, the AHR receptor is activated within a subject in need of activation of the AHR receptor. TEACOPs or TEACOPs derivatives are expected to give maximum AHR induction activity that is much higher than aberrant AHR ligands, such as environmental toxicants to gain full physiological functions. Thus, some TEACOPs or TEACOPs derivatives might block the toxicity responses caused by aberrant activation of AHR by environmental ligands.

Aryl hydrocarbon receptor (AHR) is a PAS family transcription factor with broad specificity for environmental and cellular ligands and mediates diverse biological processes varied from toxicity to normal physiology. Depending on ligand shape and chemical properties, diverse AHR ligands lead to distinctly different biological consequences.

In some embodiments, the compounds described herein ca be used for developing novel therapeutics for mitigating the many pathological conditions associated with altered AHR activation. Kynurenine plays a role in the normal physiological function of AHR. The cellular levels of kynurenine play crucial roles in regulating the immune system, vascular biology and neurological function[1-4]. Altered kynurenine function is associated with a variety of human health issues including cancer, hypertension, chronic inflammation, and neurodegenerative disorders[1,5,6]. Kynurenine-mediated AHR activation plays a crucial role in protecting diverse organs from inflammatory diseases[7,13,14,38,39]. Maintaining a normal level of kynurenine by inhibiting its downstream metabolizing enzyme was proved useful for preventing multiple organ failure[39]. Both AHR and the kynurenine-generating enzyme, IDO, are highly expressed in placenta with a well-established role in pregnancy and the health of new born babies[49-47]. Preeclampsia (PE) is a dangerous complication of pregnancy and inflammation plays a significant role in this common clinical conditions. Deficient uteroplacental blood flow and associated inflammation are at the root of preterm birth, and fetal growth restriction in PE. Kynurenine-mediated AHR activation is crucial for preventing pregnancy complications, such as PE, potentially by vascular remodeling and mitigating immune responses in placenta. Alleviation of pregnancy complications presents important impacts on developmental origins of health and disease (DOHaD) that affect broad human diseases[41,48-51]. Our discovery that kynurenine activates AHR by formation of trace extended aromatic condensation products, which we abbreviated as TEACOPs, reconciles a long-term dilemma in the field that the structure of kynurenine itself does not conform to many of the rules that correlate with high affinity binding to AHR[29-32]. Developing novel TEACOPs and their derivatives are extremely helpful for mitigating broad inflammatory human diseases and PE as indicated above.

As used herein "subject" or "patient" refers to mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex. In one specific embodiment, a subject is a mammal, preferably a human.

As used herein, the terms "effective amount" and "therapeutically effective amount" refer to the quantity of active therapeutic agent or agents sufficient to yield a desired therapeutic response without undue adverse side effects such as toxicity, irritation, or allergic response. The specific "effective amount" will, obviously, vary with such factors as the particular condition being treated, the physical condition of the subject, the type of animal being treated, the duration of the treatment, the nature of concurrent therapy (if any), and the specific formulations employed and the structure of the compounds or its derivatives.

In some embodiments, the present disclosure provides a method treating a subject having a kynurenine disorder, the method comprising administering an effected amount of the compound of any one of formula (I)-(V) wherein the kynurenine disorder is treated. Suitable kynurenine disorders include, but are not limited to, preeclampsia, cancer, or autoimmune disorders. Given the ability of the embodiments to suppress inflammatory immune responses, they can also be used to reduce transplant rejection.

For purposes of the present invention, "treating" or "treatment" describes the management and care of a subject for the purpose of combating the disease, condition, or disorder. Treating includes the administration of a compound of pharmaceutical composition of present invention to prevent the onset of the symptoms or complications, alleviating the symptoms or complications, or eliminating the disease, condition, or disorder. Treating also encompasses therapeutic and palliative treatment.

In some embodiments, kits for carrying out the methods described herein are provided. The kits provided may contain the necessary components in which to carry out one or more of the above-noted methods.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit's interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim.

The present invention has been described in terms of one or more preferred embodiments, and it should be appreciated that many equivalents, alternatives, variations, and modifications, aside from those expressly stated, are possible and within the scope of the invention.

The invention will be more fully understood upon consideration of the following non-limiting examples.

EXAMPLES

Example 1: Trace Derivatives of Kynurenine as Potent AHR Ligands

Cellular metabolites act as important signaling cues, but are subject to complex unknown chemistry. Kynurenine is a tryptophan metabolite that plays a crucial role in cancer and the immune system. Despite its atypical, non-ligand-like, highly polar structure, kynurenine activates the aryl hydrocarbon receptor (AHR), a PAS family transcription factor that responds to diverse environmental and cellular ligands. The activity of kynurenine increases 100-1000-fold by incubation or long-term storage. Both fresh and activated kynurenine are dependent upon the hydrophobic AHR ligand-binding pocket, and share identical structural signatures for receptor activation.

In this Example, the inventors purified trace active derivatives of kynurenine and identified two novel, closely-related condensation products, named as TEACOPs (trace extended aromatic condensation products), which are active at low picomolar levels. The synthesized compound for one of the predicted structures matches the purified compound in both chemical structure and AHR pharmacology. This Example provides evidence that kynurenine acts as an AHR pro-ligand, which requires novel chemical conversions to act as a receptor agonist.

Based on our previous models of AHR-LBD bound to TCDD and BaP (Xing, Nukaya et al. 2012), we generated a model of AHR-LBD bound to FICZ that is consistent with AHR structural signatures controlling FICZ-binding, but could not build a model for AHR bound to a single kynurenine molecule. This observation, coupled to our previous speculation that kynurenine "breakdown products" or metabolites were the actual AHR ligands (Mezrich, Fechner et al. 2010), we decided to test the idea that kynurenine is a pro-ligand of AHR, which spontaneously converts in solution to yield trace extended aromatic condensation products (TEACOPs) that act as high affinity AHR ligands. By extensive fractionation and characterization, we identified two closely-related novel kynurenine derivatives with picomolar ECSO values. The predicted structures were confirmed through synthesis of compounds that match the purified compound in both chemical structure and AHR induction.

Low In Vitro Potency and Structural Signatures Governing AHR Binding Oppose Models of Single Kynurenine Bound to AHR-LBD We compared the ability of kynurenine and FICZ (6-formylindolo [3,2-b] carbazole), another tryptophan derivative that acts as a potent AHR ligand (Rannug, Rannug et al. 1987, Helferich and Denison 1991), to activate the mouse AHR (mAHR B1-allele, simplified as AHR or mAHR if not specified) using a luciferase reporter gene assay (Han, Nagy et al. 2004). COS-1 cells expressing mAHR were treated with increasing doses of FICZ and kynurenine for 4 hours. Consistent with previous observations, FICZ exhibits a very high AHR activation activity with a measured EC50 of 36 pM (FIG. 1A). This value is similar to the measured $K_D$ value of 70 pM (Rannug, Rannug et al. 1987), and the EC50 of 34 pM for MH1C1 rat hepatoma cells exposed for three hours (Wei, Helleberg et al. 1998, Wei, Bergander et al. 2000, Bergander, Wincent et al. 2004). As observed previously (Opitz, Litzenburger et al. 2011), kynurenine induces a maximum AHR activation that is ~40% higher than that induced by FICZ (FIG. 1A). The EC50 of kynurenine was measured to be approximately 13 µM (FIG. 1A). The low biological potency of kynurenine that we observed is consistent with its predicted "non-ligand-like" structure, but could not account for its in vivo function via AHR, suggesting that a single kynurenine might not directly act as an AHR ligand.

Figure 6:
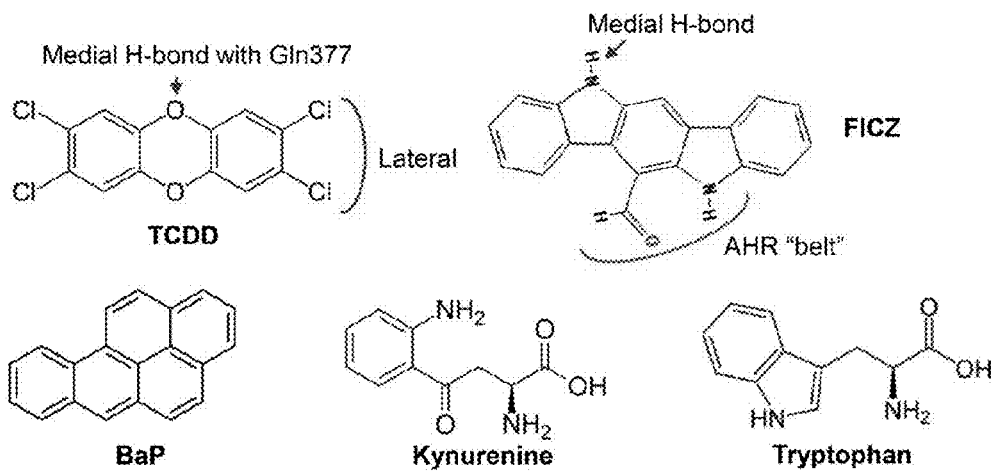
FIG. 6 depicts the chemical structures of AHR ligands. Shown are chemical structures of well-known AHR ligands, TCDD, FICZ, BaP, and kynurenine, compared to tryptophan. The chemical signatures of TCDD and FICZ with medial H-bond potential, facing lateral extension and the "belt" of the AHR ligand-binding pocket are illustrated.

The high potency of FICZ in AHR activation can be readily predicted from its chemical structure and its predicted fit to our structural model of AHR-LBD (Xing, Nukaya et al. 2012). As an aromatic heterocyclic multi-ring compound, FICZ has an overall planar and elongated shape similar to TCDD (FIG. 6), one of the most active AHR ligands ever identified (Bjeldanes, Kim et al. 1991). The relatively even top edge of FICZ gives minimal medial extension similar to TCDD and harbors an —NH group facing the medial residue of the AHR-ligand binding domains (LBD), Gln377, which defines the H-bond potential and explains the preferences of AHR for small extensions at the medial position (Xing, Nukaya et al. 2012). In this orientation, the larger aldehyde extension at the opposite side would be placed near, and be well accommodated by, the flexible "belt" (FIG. 6). To confirm this prediction, we performed molecular docking of FICZ to our model of AHR-LBD. The binding mode of FICZ to AHR-LBD (FIG. 7A) is exactly as predicted above.

Figures 7A, 7B, 7C, 7D:
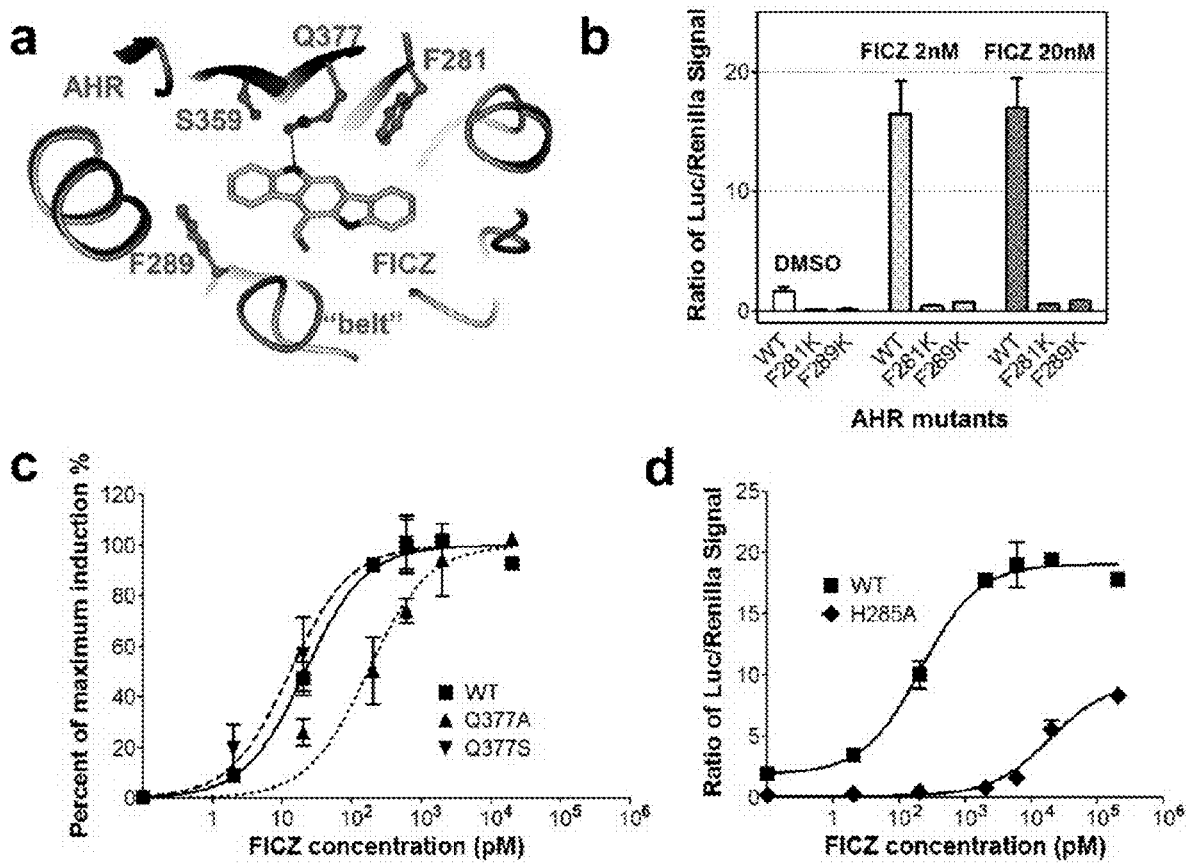
FIGS. 7A-7D show the structural model and structural signatures for AHR-FICZ interactions. (a) Structural model of FICZ bound to AHR ligand-binding pocket. AHR is colored magenta and shown in cartoon. Key residues of AHR is shown in ball-and-stick and colored by atom type. FICZ is in stick and colored cyan and by atom type. Intermolecular H-bonds are in black dashed line. (b) Induction of the transcriptional activity of WT and mutant mAHR, F289K and F281K, by FICZ (2 nM and 20 nM), DMSO as control. (c) Dose-dependent response curves of the transcriptional activity of WT mAHR and its medial position mutants (Q377A and Q377S) to FICZ. COS-1 cells expressing WT or mutant mAHR were treated by increasing concentrations of ligands for 4 hrs followed by determination of the induced luciferase activity. The level of induction was normalized to that of the WT mAHR. The loss of medial H-bond potential by Q377A reduced the activity of FICZ by 5-fold. (d) Dose-dependent response curves of the transcriptional activity of WT mAHR and its lateral H-bond network mutant (H285A) to FICZ. The induction level of the AHR activity was measured and normalized to the signal of renilla luciferase. All experiments shown in c and d were performed in triplicates and repeated twice.

In contrast, kynurenine fits poorly to the AHR ligand-binding pocket in two potential orientations (FIG. 1B) and the calculated docking energies are at least 3 kcal weaker than that for FICZ. In addition, the terminal carboxylate group of kynurenine is placed near Phe289 or Phe281 within highly hydrophobic portions of the pocket. Nonetheless, the predicted extensive H-bond interactions between kynurenine terminal carboxylate and amine groups and the AHR medial residues, Gln377 and Ser359 might alleviate these unfavorable acidic-hydrophobic contacts. These models suggest that mutation of Phe289 or Phe281 in AHR to the positively charged lysine would enhance the interaction of kynurenine with AHR and thus increase its AHR induction activity. Contrary to our reasoning, neither F289K nor F281K could enhance the activity of kynurenine; instead, both completely abolished the responsiveness of AHR to kynurenine (FIG. 1c). Similar effects of these AHR mutations were observed for FICZ (FIG. 7b). Mutation of other hydrophobic residues to the positively charged lysine or arginine also completely abolished the activity of kynurenine (FIG. 1c), suggesting that, despite its high polarity, kynurenine prefers the hydrophobic AHR ligand-binding pocket for AHR activation. Furthermore, mutation of Gln377 to alanine barely affected kynurenine activity (FIG. 1d), while both models predicted that this mutation should abolish medial H-bond interactions with kynurenine (FIG. 1b). Instead, Q377A reduced the efficacy of FICZ by five-fold (FIG. 7c), consistent with the medial H-bond interaction between FICZ and Gln377 (FIG. 7a). The AHR mutation H285A, which abolishes an H-bond network crucial to defining the overall shape of the ligand-binding pocket (Xing, Nukaya et al. 2012), completely disrupts kynurenine activity (FIG. 1d), but remains partially receptive to FICZ binding (FIG. 7d). This is counterintuitive, given the much smaller size of kynurenine compared to FICZ. For all mutational analysis, mutant mAHRs were expressed at a similar level to the wild-type (FIG. 1e). Collectively, these data support our model of FICZ bound to AHR (FIG. 7a), but are not consistent with either model of AHR bound to kynurenine (FIG. 1b). This conclusion is consistent with the non-ligand-like structure of kynurenine (FIG. 6).

Figures 2A, 2B, 2C, 2D:
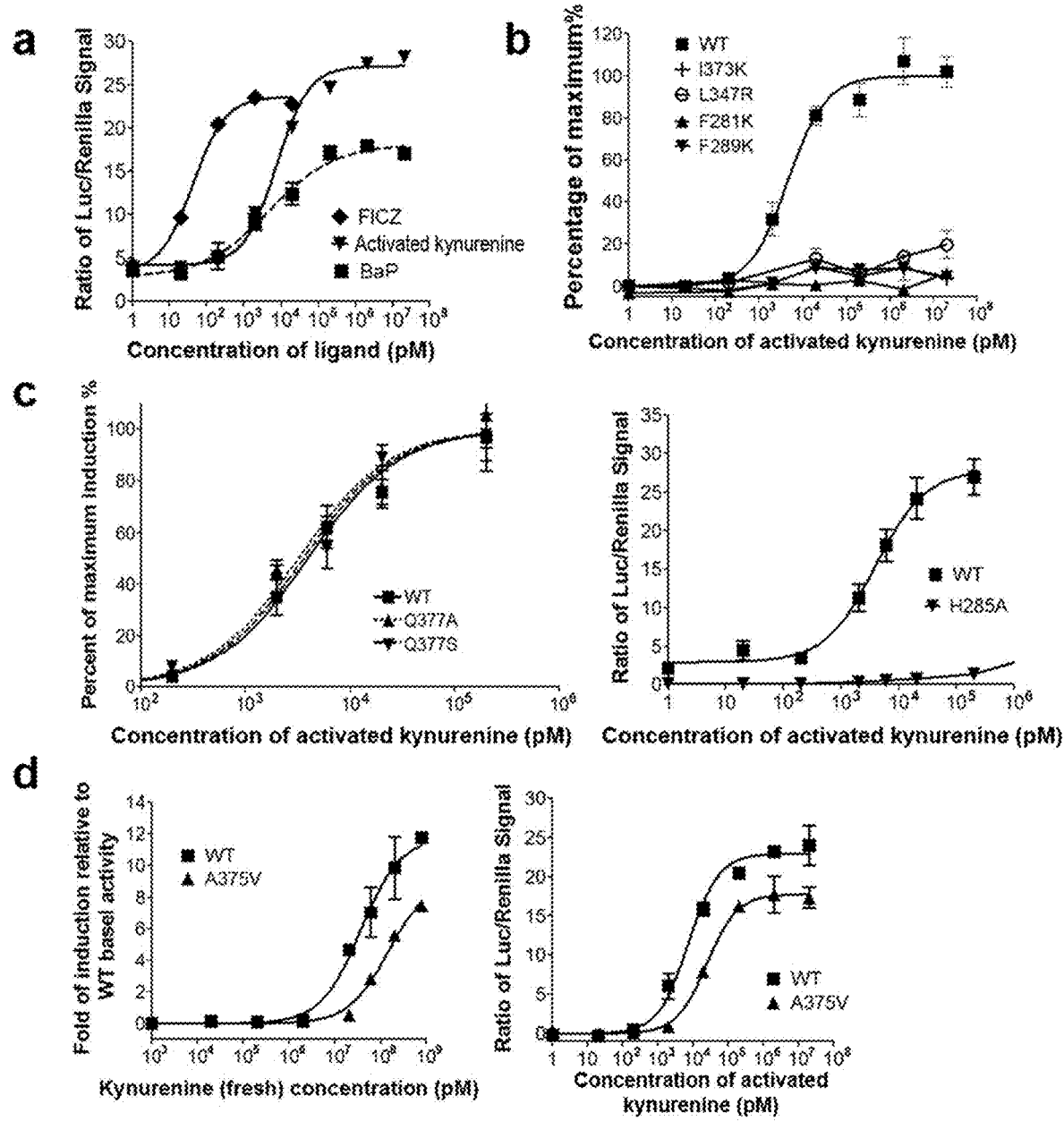
FIGS. 2A-2D are graphs demonstrating activated kynurenine shares identical structural signatures as fresh kynurenine in AHR induction and both activate different AHR genetic variants. (a) Dose-dependent response curves of AHR ligands in induction of the transcriptional activity of mAHR, with activated kynurenine compared to FICZ and BaP, similar to FIG. 1a. (b) Dose-dependent response curves of WT and mutant AHR, F289K, F281K, I373K, and L347R, to the activated kynurenine, determined as in FIG. 1a. The level of AHR activity was normalized to the maximum induction. (c) Dose-dependent response curves of activated kynurenine in activation of WT and mutant AHR bearing mutation to the residue with medial H-bond potential, Q377A (left), or the residue that forms part of H-bond network lining the ligand-binding pocket, H285A. The level of AHR activity was determined as in FIG. 1d. (d) Dose-dependent response curves of WT mAHR (B-allele) and its genetic variant A375V (D-allele) to fresh (left) and activated (right) kynurenine. The level of AHR activity was normalized to the fold of induction relative to WT basal activity or to the signal of renilla luciferase, followed by normalization of basal activity to zero.

Activated Kynurenine Shares Identical Structural Signatures in AHR Binding and the Ability to Activate Different Genetic Variants of AHR The low in vitro potency of kynurenine in AHR activation (FIG. 1a) is difficult to reconcile with its known action through AHR in vivo. In initial examinations of the idea that kynurenine is converted to a more potent structure in vitro or in vivo, we discovered that kynurenine solution stored at −20° C. for two years exhibited more than 1000-fold higher activity than a freshly prepared solution of kynurenine (EC50=5 nM) (FIG. 2a). We refer to this "aged" kynurenine as "activated kynurenine". Like fresh kynurenine (FIG. 1a), activated kynurenine exhibited a higher level of maximum activity in AHR activation compared to other ligands, such as FICZ and BaP (FIG. 2a). Furthermore, the structural signatures, as defined by mutational analysis, governing AHR binding are identical for fresh and activated kynurenine (FIG. 1c-d&2b-c). Similar to fresh kynurenine, activated kynurenine prefers the overall hydrophobic AHR ligand-binding pocket and fails to activate mutant AHR with alterations to its hydrophobic residues, such as F281K, F289K, I373K, and I347R (FIG. 2b). AHR induction by activated kynurenine was barely affected by AHR mutation Q377A, and completely abolished by H285A (FIG. 2c), just like fresh kynurenine (FIG. 1d). The identical structural signatures governing AHR binding let us predict that the same chemical compounds function as AHR ligands in both fresh and activated kynurenine. It seems plausible that these compounds are spontaneous kynurenine derivatives and their abundance increases more than 1000-fold after two-year storage.

Figures 8A, 8B:
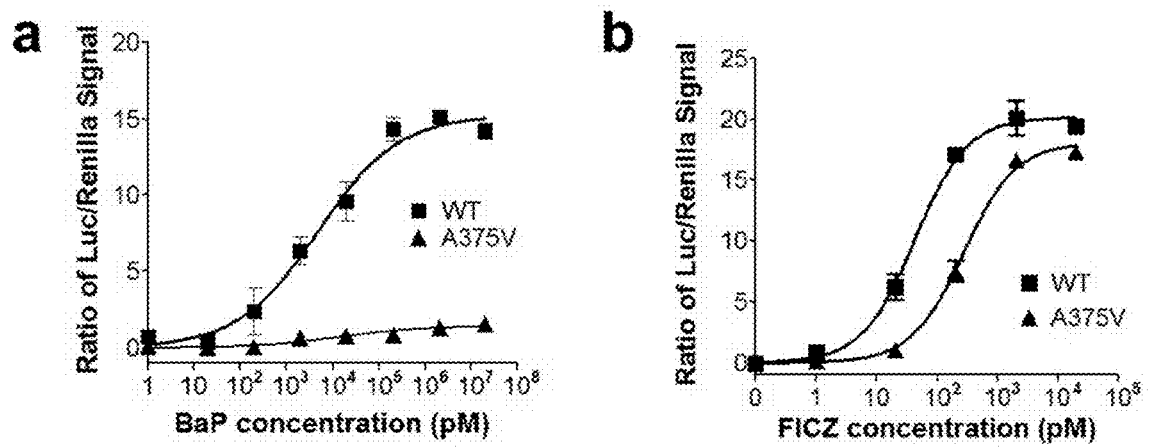
FIGS. 8A-8B depict dose-dependent response curves of WT mAHR (B-allele) and its genetic variant A375V (D-allele) to environmental toxicant, BaP (left, a) and FICZ (right, b). The level of AHR activity was normalized to the fold of induction relative to WT basal activity, followed by normalization of basal activity to zero.

Physiological relevant ligands of the AHR would be expected to activate polymorphic receptors within species and structurally variant receptors across species. As a model of this idea an important endogenous AHR ligands would be expected to activate AHR genetic variants arising from the murine Ahr B1 and D alleles. These two well-known genetic variants, harbor a key sequence variation at residue 375, with alanine in the B1 allele, and valine in the D allele (A375V). Residue 375 is located near the medial position of the AHR-LBD. The A375V variant has weakened binding to TCDD and other xenobiotic AHR ligands (Chang, Smith et al. 1993, Ema, Ohe et al. 1994, Poland, Palen et al. 1994). This replacement increases the steric hindrance to the medial positions of ligands (Xing, Nukaya et al. 2012), particularly environmental ligands that are bulkier in the medial direction, such as BaP, which could barely stimulate the activity of the A375V D-allele (FIG. 8a) (Xing, Nukaya et al. 2012). In sharp contrast, both fresh and activated kynurenine can readily activate the B-allele and the A375V D-allele, and their AHR induction activities were affected similarly by this genetic variant (FIG. 2d). A similar observation was made using FICZ ligand (FIG. 8b). Taken together, kynurenine and FICZ exhibited much less difference in their responses to AHR genetic variants than do environmental compounds. These observations support the notion that AHR genetic variants might function through these endogenous ligands to control normal physiological functions. Collectively, our study showed that fresh and activated kynurenine share the same modes of interaction with AHR, which partially resembles the binding mode of FICZ. We thus predicted that spontaneous chemical conversion of kynurenine to extended aromatic condensation products (EACOPS) might result in heterocyclic multi-ring aromatic compounds, with ligand biding affinities similar to FICZ.

Spontaneous Chemical Conversion of Kynurenine

Figures 3A, 3B, 3C, 3D:
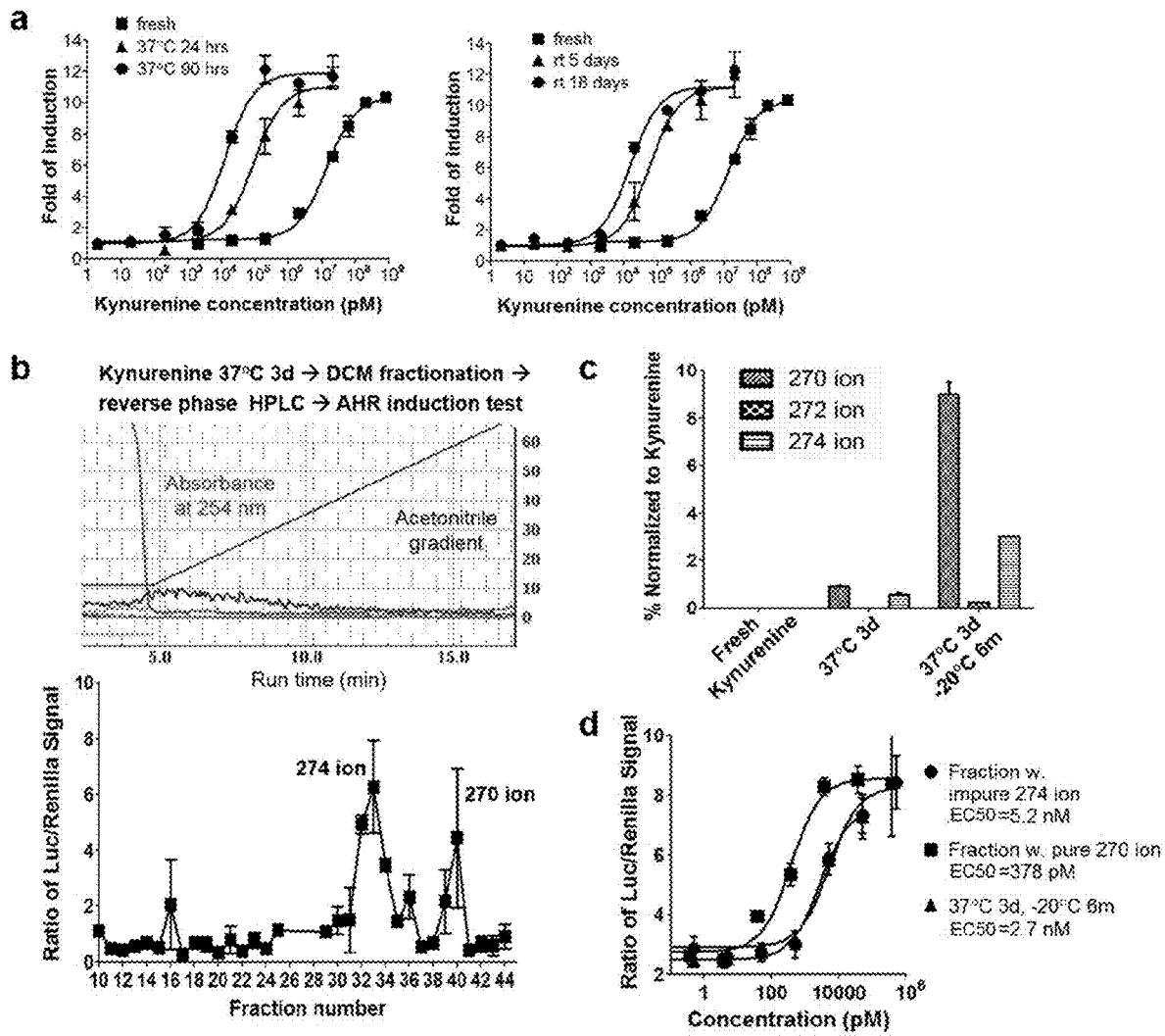
FIGS. 3A-3D demonstrate temperature-dependent spontaneous chemical conversion of kynurenine and fractionation and identification of novel derivatives with potent AHR induction activity. (a) Dose-dependent response curves of mAHR to kynurenine samples that were freshly prepared, or incubated for indicated amounts of time at 37° C. (left) or room temperature (right). (b) Fractionation of kynurenine derivatives and monitoring of their AHR induction activity. Experimental scheme is shown at top, the profile of reverse phase HPLC is in middle, and the transcriptional activity of mAHR induced by HPLC fractions is at bottom. Key ions associated with each active peak are indicated. (c) Quantitative LC/MS analysis of ions of kynurenine derivatives for three indicated samples, fresh kynurenine, kynurenine incubated at 37° C. for 3 days (3 d), and kynurenine incubated for at 37° C. 3 days followed by storage in −20° C. for 6 months (3 d, 6 m). The average peak areas of 270, 272, and 274 ions were normalized to that of kynurenine mother ions. (d) Dose-dependent response curves of mAHR to kynurenine derivative fractions associated with the 274 and 270 ions, respectively, compared to kynurenine (3 d, 6 m) used in (c). The $EC_{50}$ of each sample is shown.
Figures 9A, 9B:
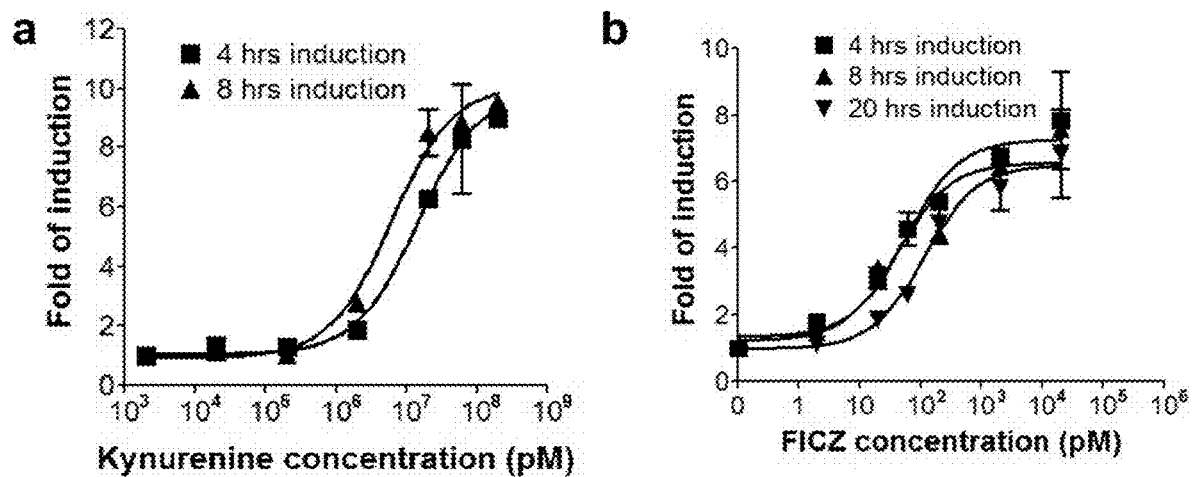
FIGS. 9A-9B show increase of AHR induction time is associated with increased kynurenine activity, but reduced FICZ activity. (a) Dose-dependent response curves of the transcriptional activity of mAHR to fresh kynurenine. COS-1 cells expressing WT mAHR were treated by increasing concentrations of ligands for 4 hrs and 8 hrs followed by determination of the induced luciferase activity. (b) Dose-dependent response curves of the transcriptional activity of mAHR to FICZ. COS-1 cells expressing WT mAHR were treated by increasing concentrations of FICZ for 4 hrs, 8 hrs, and 20 hrs similar to (a).

Based on the above ideas, we examined whether chemical conversion of kynurenine to activated kynurenine can be sped up by increasing incubation temperature. Incubation of kynurenine solution at room temperature or 37° C. continuously increased AHR induction activity by kynurenine. Induction increased ~100-fold by incubation after three days at 37° C. or after 18 days at room temperature (FIG. 3a). Consistent with this observation, AHR activation by kynurenine in COS-1 cells for eight hours gave a higher biological response compared to a four-hour induction (FIG. 9a). In contrast, FICZ activity was slightly reduced in the eight-hour versus four-hour induction, and further reduced in the 20-hour induction (FIG. 9b). These results suggest that while active derivatives of kynurenine accumulated continuously during AHR induction, longer incubation times with FICZ have lower efficacy due to cellular turnover or FICZ metabolism.

Figures 10A, 10B:
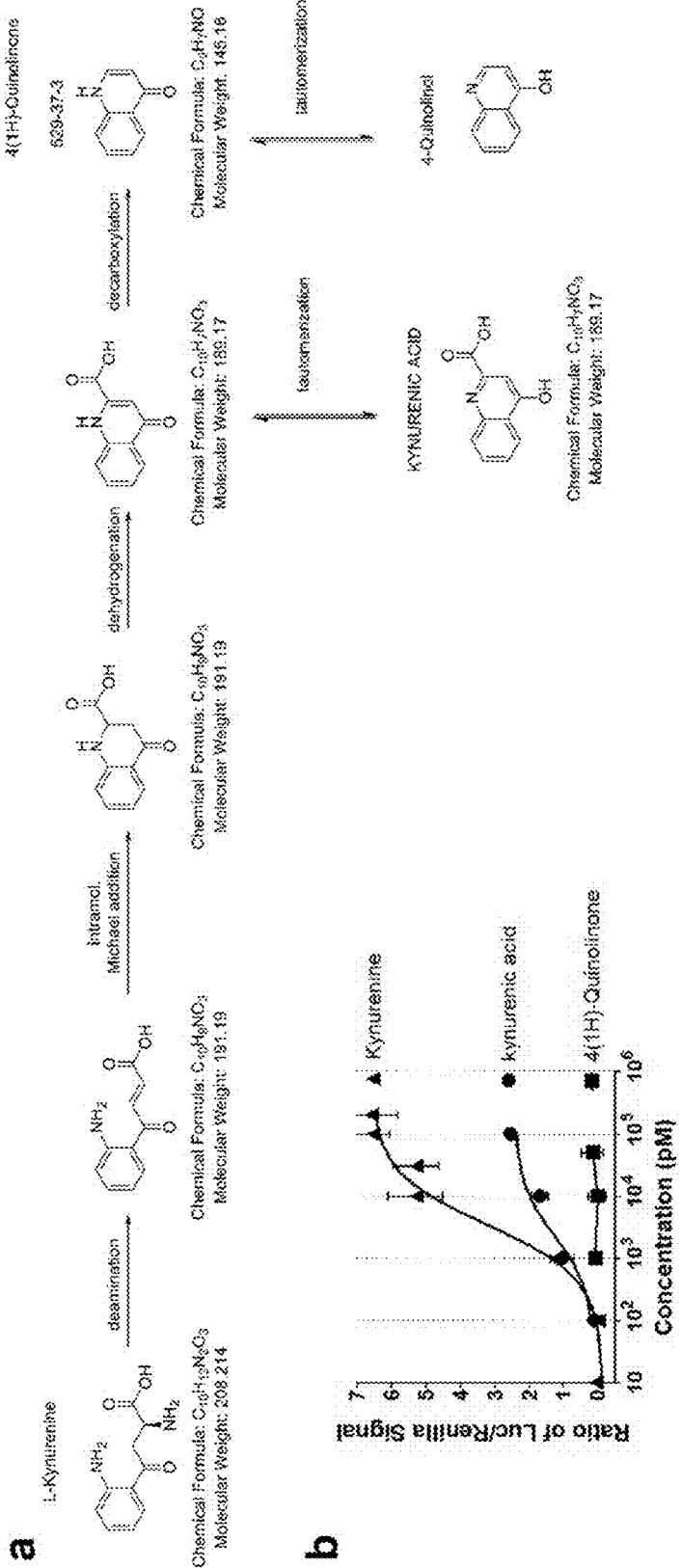

Kynurenine is metabolized to different compounds by diverse enzymes in the kynurenine pathway (Stone and Darlington 2002), and many of these metabolic intermediates (other than kynurenine) are not active in AHR activation assays (Mezrich, Fechner et al. 2010). As kynurenine is also known to be chemically converted to several other well characterized derivatives (Brown and Becher 1967, Tokuyama, Senoh et al. 1967, Zelentsova, Sherin et al. 2013) (FIG. 10a), we next determined whether any known chemical derivatives of kynurenine could activate AHR. In this regard, Kynurenic acid exhibited a low activity in AHR induction and 4(1H)-Quinolinone (4-HQ) did not show any activity. Given that response to these metabolites is much lower than fresh kynurenine (FIG. 10b), they are thus unlikely accounting for the activity of activated kynurenine. Other compounds in the chemical conversion scheme shown in FIG. 10a are similar to either kynurenic acid, 4-HQ, or kynurenine itself. This led us to conclude that the AHR ligands derived from kynurenine are mostly likely unknown trace condensation products that had not yet been identified.

Identification of Two Potent and Closely-Related Trace Derivatives of Kynurenine To identify the putative active kynurenine products, we incubated 200 mg of kynurenine at 37° C. for 3 days, followed by phase separation between dichloromethane (DCM) and water, with the DCM phase retained nearly 50% of the total activity. Based on our prediction of the extended multi-ring aromatic structure of the active derivatives, we expected that the DCM phase would enrich these compounds over the abundant kynurenine and its polar derivatives. Consistently, reverse phase preparative HPLC fractionation of compounds from the DCM phase gave a spectrum with barely any absorbance peaks at 254 nm during acetonitrile gradient, but AHR induction tests detected two prominent peaks that could activate AHR (FIG. 3b). These observations support our earlier supposition that the active derivatives of kynurenine are highly potent and are only present in trace amounts. Mass spectrometry coupled to HPLC detected a 274 ion and 270 ion in the two peaks, respectively. The peak of the 270 ion appeared at a higher acetonitrile gradient, suggesting a higher hydrophobicity.

Figure 11:
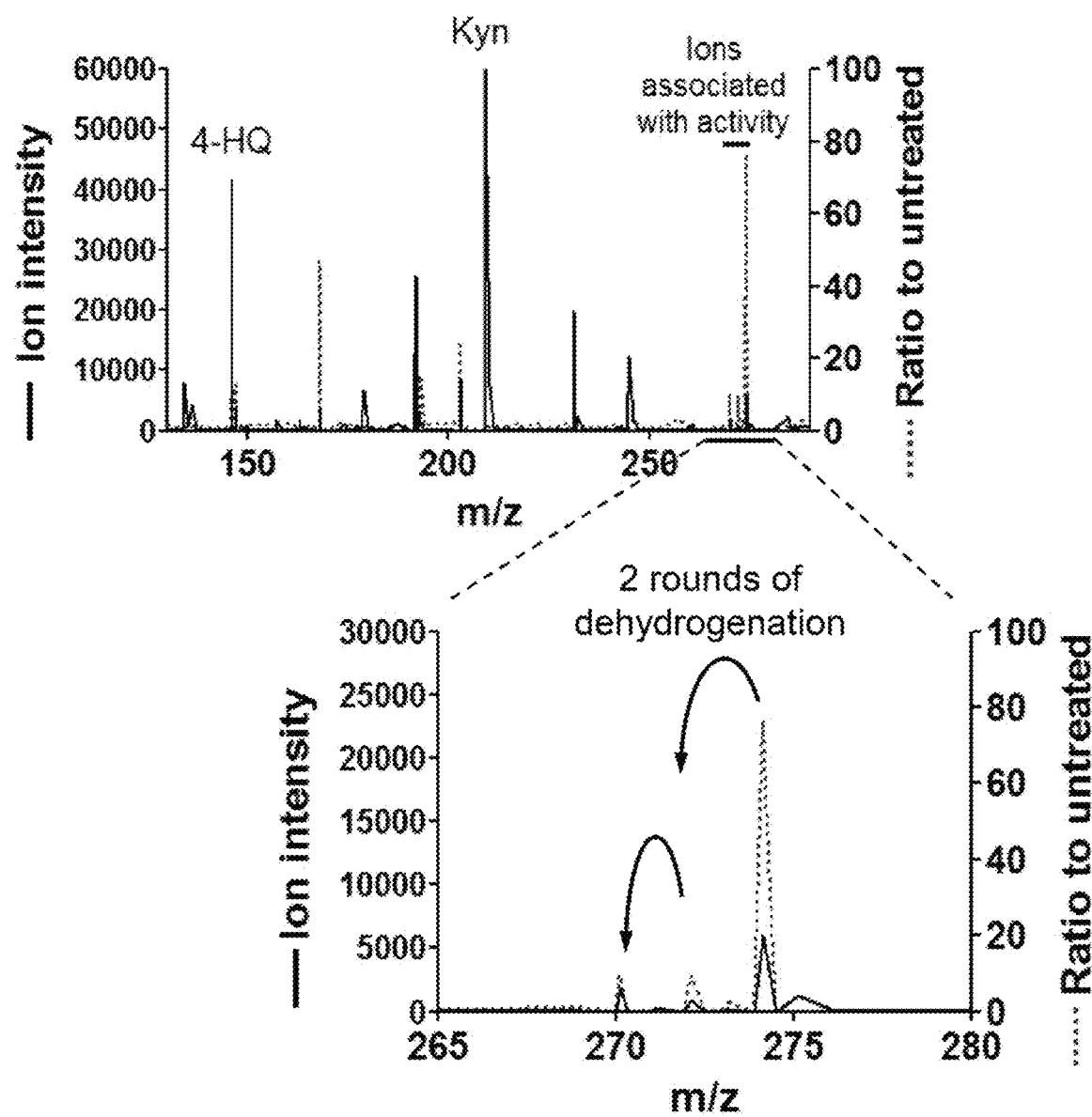
FIG. 11 shows LC-MS analysis of fresh and activated kynurenine chemical mixtures. Ion intensities for activated kynurenine were shown in solid black peaks. Changes of ion intensity for each ion before and after activation were calculated as ratios of activated kynurenine to fresh kynurenine (red dash peaks). The 274 ion although has a low ion intensity, the changes of its abundance after activation was most prominent among all ions. The detection of 272 and 270 ions provided the first clue that the 274 and 270 ions are closely-related, novel derivatives of kynurenine.

Analysis of fresh and three-day incubated kynurenine by high-resolution mass spectrometry detected known kynurenine derivatives at a high intensity after three-day incubation at 37° C., such as 4-HQ and kynurenic acid. Intriguingly, the intensity of the 274 ion was most increased among all ions detected (FIG. 11). Close examination of the mass spectra also identified the closely-related 272 and 270 ions in the three-day incubation sample (FIG. 11), which hinted to us that the 270 ion might be a two-round dehydrogenation product of the 274 ion. To accurately quantify the level of 270, 272, and 274 ions in kynurenine samples, LC-MS was performed and the peak area for each ion was normalized to kynurenine mother ion. While the 270, 272, and 274 ions were barely detected in fresh kynurenine, the 270 and 274 ions were detected in less than 1% comparing to kynurenine mother ion in the three-day incubation sample (FIG. 3c). After three-day incubation at 37° C., the sample that had been stored at −20° C. for six months yielded almost 10% 270 ion, 3% 274 ion, and readily detectable 272 ion (FIG. 3c). Consistently, this sample gave an EC50 of 2.7 nM for AHR activation (FIG. 3d), more active than the activated kynurenine tested earlier (FIG. 2a).

To facilitate chemical and functional characterization of the 274 and 270 ions, we scaled up the purification of active AHR ligands from two grams of kynurenine after three-day 37° C. incubation following procedures shown in FIG. 3a. Additional rounds of HPLC purification were performed to gain purity. The 270 ion fraction was relatively pure, but the 274 ion fraction contained a few other more dominant ions. The 270 ion gave an EC50 of 378 pM for induction of cellular AHR (FIG. 3d), making it a novel, highly potent AHR ligand. The 274 ion fraction gave an AC50 of ~5 nM, which is expected to give a higher activity if pure material were obtained.

Figures 4A, 4B, 4C, 4D, 4E, 4F, 4G:
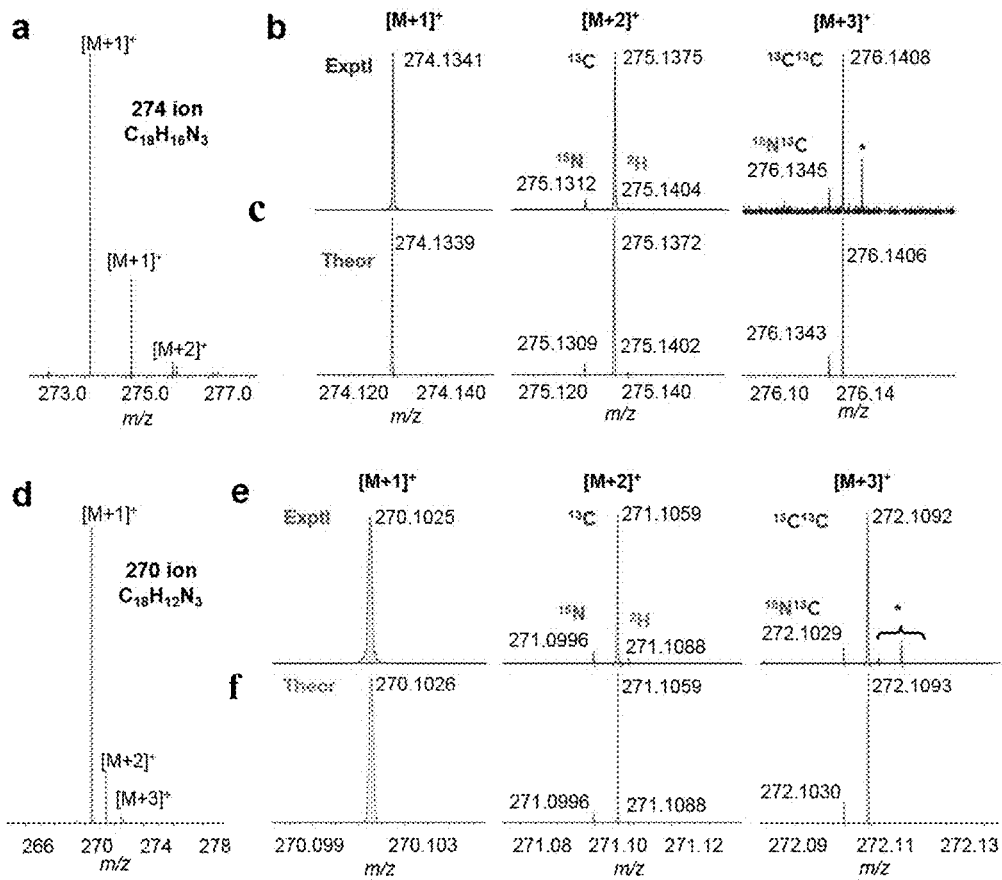
FIGS. 4A-4G shows that ultrahigh resolution Fourier transform mass spectrometry (UH-FTMS) determined the chemical formula of the trace 274 and 270 ions of kynurenine derivatives. $C_{18}H_{16}N_3^+$ isotopic fine structure determined by FTMS for the 274 ion: (a) isotopic clusters with zoom-in of individual cluster from (b) experimental and (c) theoretical results. *Belong to another ion. Likewise, $C_{18}H_{12}N_3^+$ isotopic fine structure determined by FTMS for the 270 ion: (d) isotopic clusters with zoom-in of individual cluster from (e) experimental and (f) theoretical results. *Belong to other ions. (g). Initial prediction of chemical conversions of two kynurenine molecules to the 274 ion and then to the 270 ion based on chemical formula determined in (a-f).

Deciphering the Structures and Mode of Interactions of Potent Kynurenine Derivatives To characterize the chemical structures of active kynurenine derivatives, the peaks with the 270 and 274 ions from the large scale purification described above were analyzed with ultrahigh resolution Fourier transform mass spectrometry (UH-FTMS). The chemical formulas for the 270 and 274 ions were determined: $C_{18}H_{16}N_3$ for the 274 ion and $C_{18}H_{12}N_3$ for the 270 ion (FIG. 4a-f). Consistent with our earlier prediction that the 270 ion is derived from the 274 ion, the two compounds differed by exactly four hydrogen atoms, most likely by two rounds of dehydrogenation (FIG. 4g).

Figures 5A, 5B, 5C, 5D:
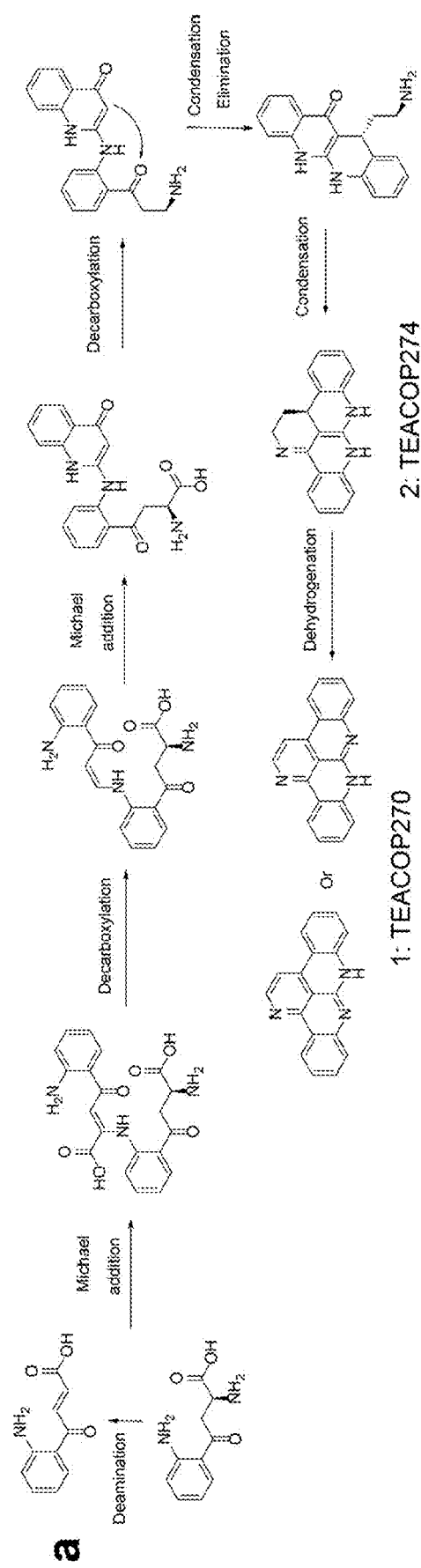
FIGS. 5A-5D show the predicted chemical conversion schemes of kynurenine to potent ligands and synthesis of potent kynurenine derivative and its mode of interactions of to AHR. (a) Chemical reaction schemes that give rise to the active 274 and 270 ions from kynurenine. The predicted structures of the two active ions are consistent with the NMR spectra provided in FIGS. 12-16 and confirmed by the synthesized compound. (b) Synthesis of the predicted compound (Compound 4) for the 270 ion. NMR spectra and assignment of all protons and carbons are provided in FIGS. 17-23. (c) Dose-dependent response curves of the synthesized Compound 4 in the free base form and the purified 270 ion in activation of WT and mutant AHR bearing mutants, Q377A and H285A. The level of AHR activity was determined as in FIG. 1a. (d) Structural model of the 270 ion bound to AHR-LBD. Key residues of AHR is shown in stick and colored by atom type. Intermolecular H-bonds are in cyan dashed line. The 270 ion are in stick and colored green and by atom type.
Figures 5A, 5B, 5C, 5D:
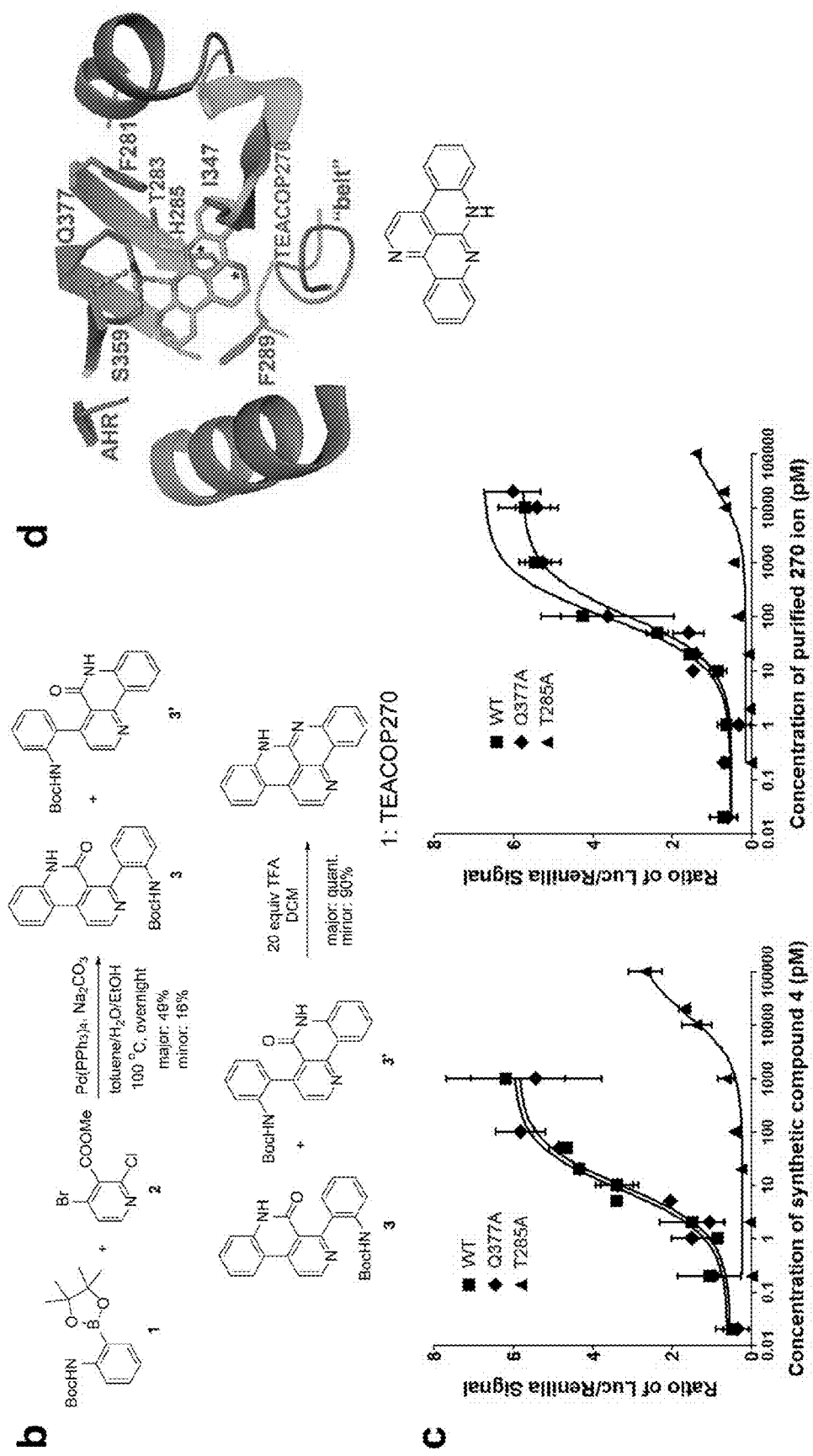

The material showing 270 ion was further analyzed with nuclear magnetic resonance (NMR) experiments. $^1H$ NMR showed ten aromatic protons (FIG. 12), which were grouped in three sets based on COSY (homonuclear Correlation Spectroscopy) data (FIG. 13), although lipid contaminations were also found present in the isolated material. Unfortunately, our efforts to get a decent $^{13}C$ NMR spectrum failed due to the very poor solubility of the isolated material in commonly used solvents ($CDCl_3$, $CD_3OD$, DMSO-$d_6$, etc). Based on the expected planar structures, formulas determined by mass spectrometry, and NMR results, we were able to predict the chemical structure of the 270 ion as well as a possible reaction pathway leading to it from kynurenine (FIG. 5a). The predicted structures for the 270, 272, and 274 ions are extended molecules with poly-aromatic rings. Due to the trace amount of these compounds in kynurenine derivatives, we term them TEACOPs (trace extended aromatic condensation products).

Figure 12:
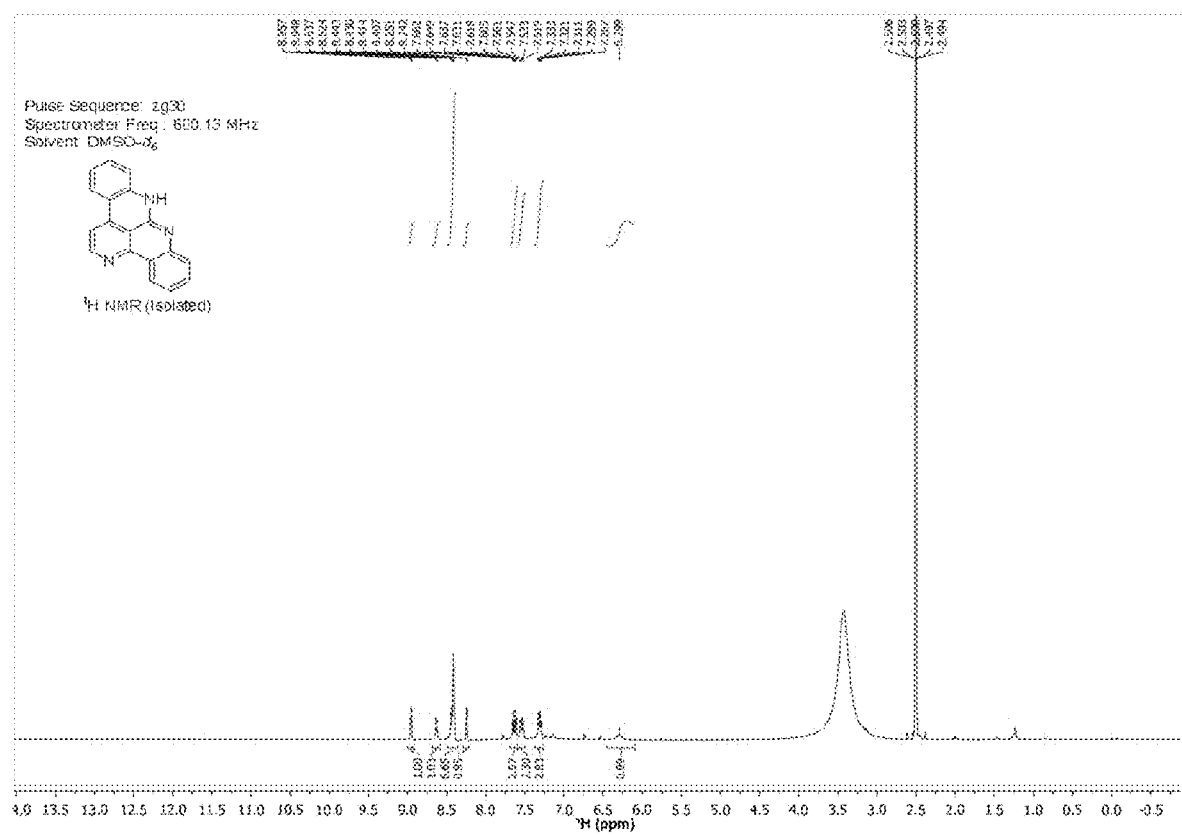
FIG. 12 shows $^1$H NMR spectrum of the isolated 270 ion.
Figure 13:
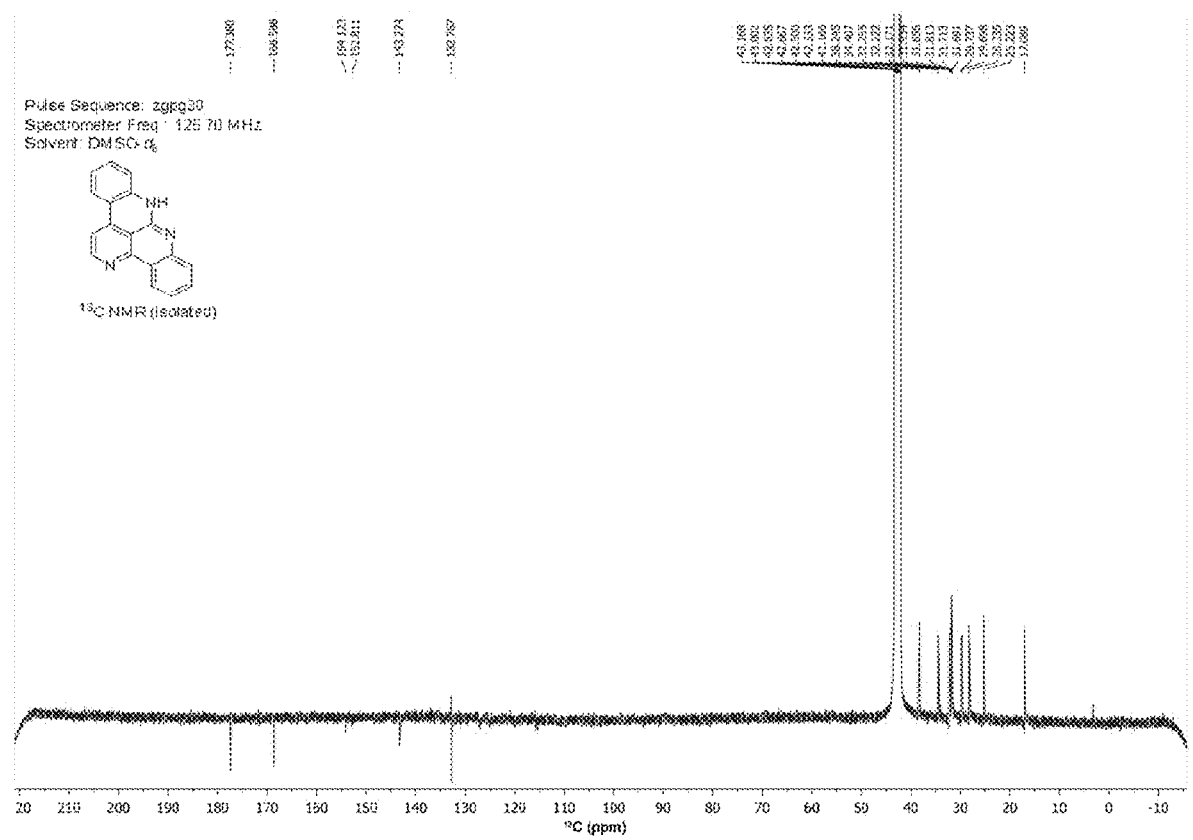
FIG. 13 shows $^{13}$C NMR spectrum of the isolated 270 ion.
Figure 14:
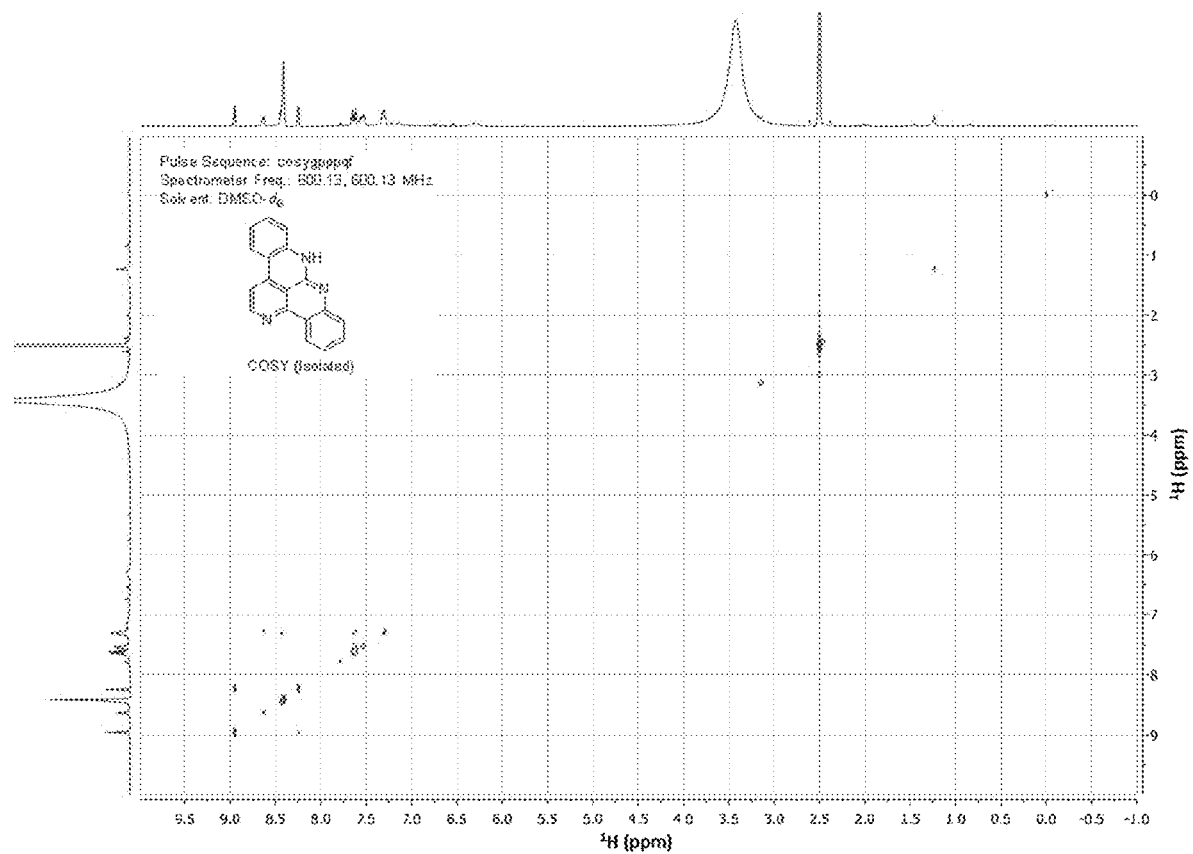
FIG. 14 shows $^1$H COSY NMR spectrum of the isolated 270 ion.
Figure 15:
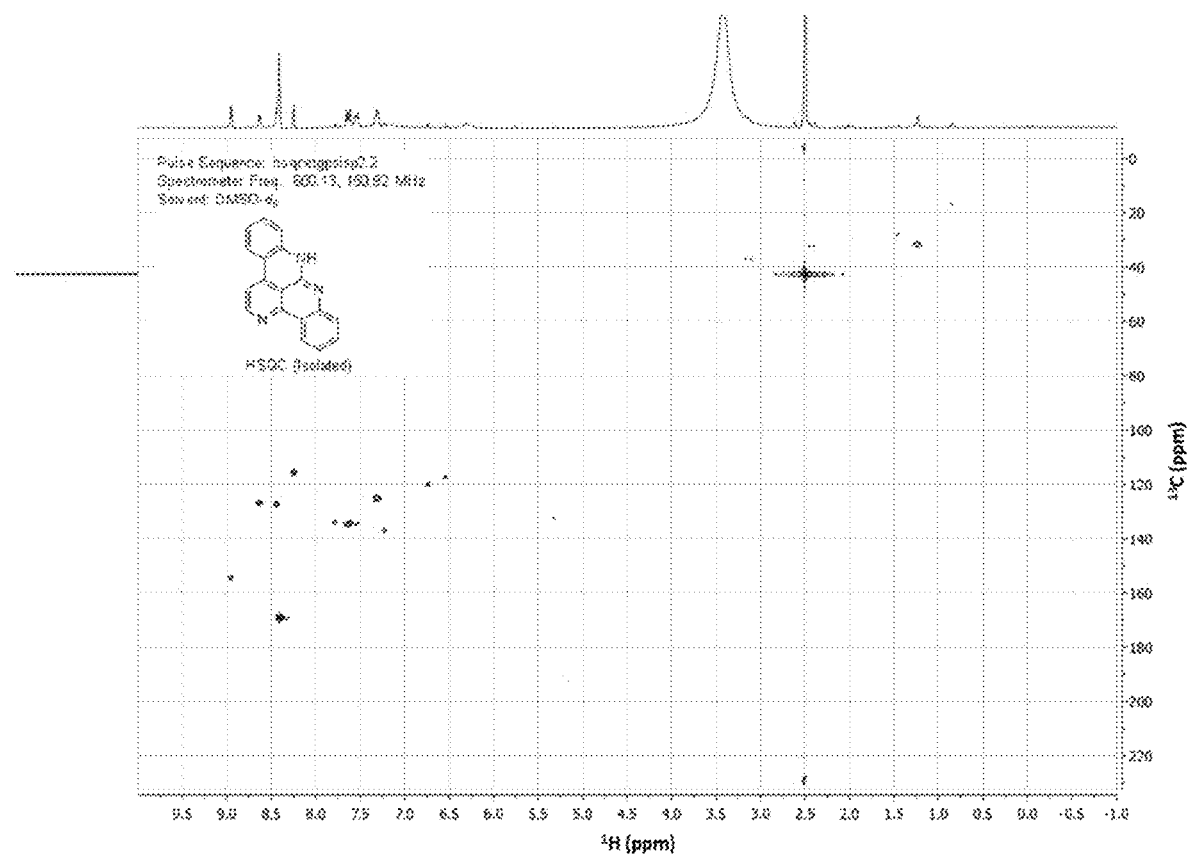
FIG. 15 shows $^1$H, $^{13}$C HSQC NMR spectrum of the isolated 270 ion.
Figure 16:
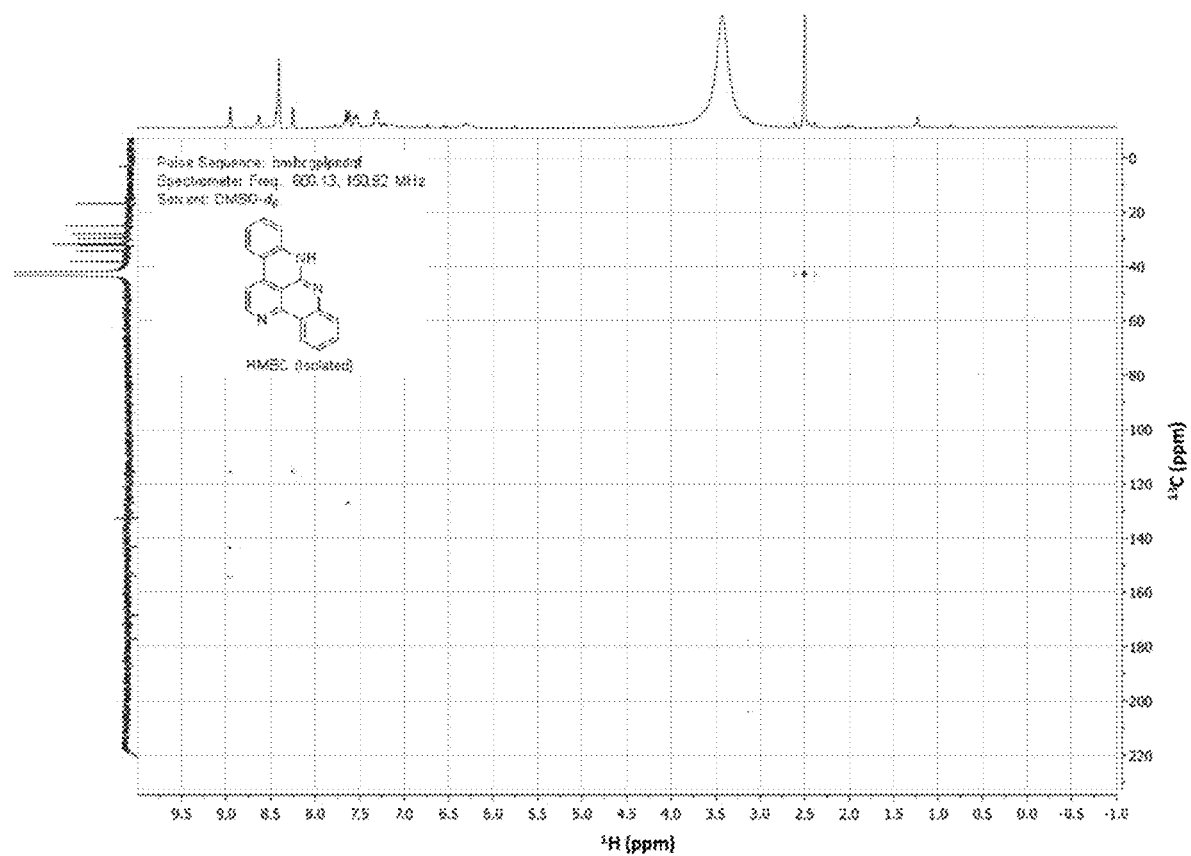
FIG. 16 shows HMBC NMR spectrum of the isolated 270 ion.
Figure 18:
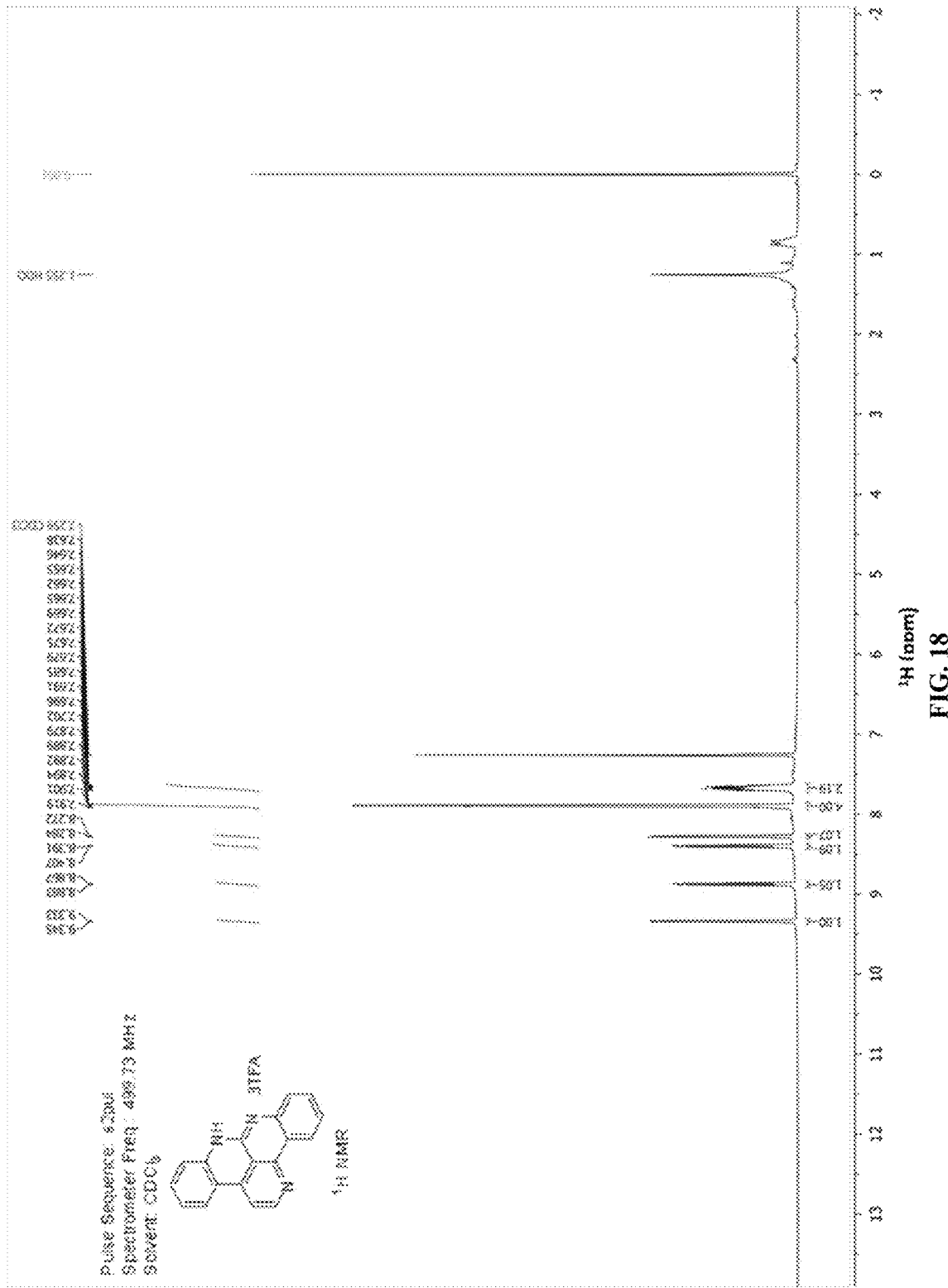
FIG. 18 shows $^1$H NMR spectrum for the TFA salt of synthesized Compound 4.
Figure 19:
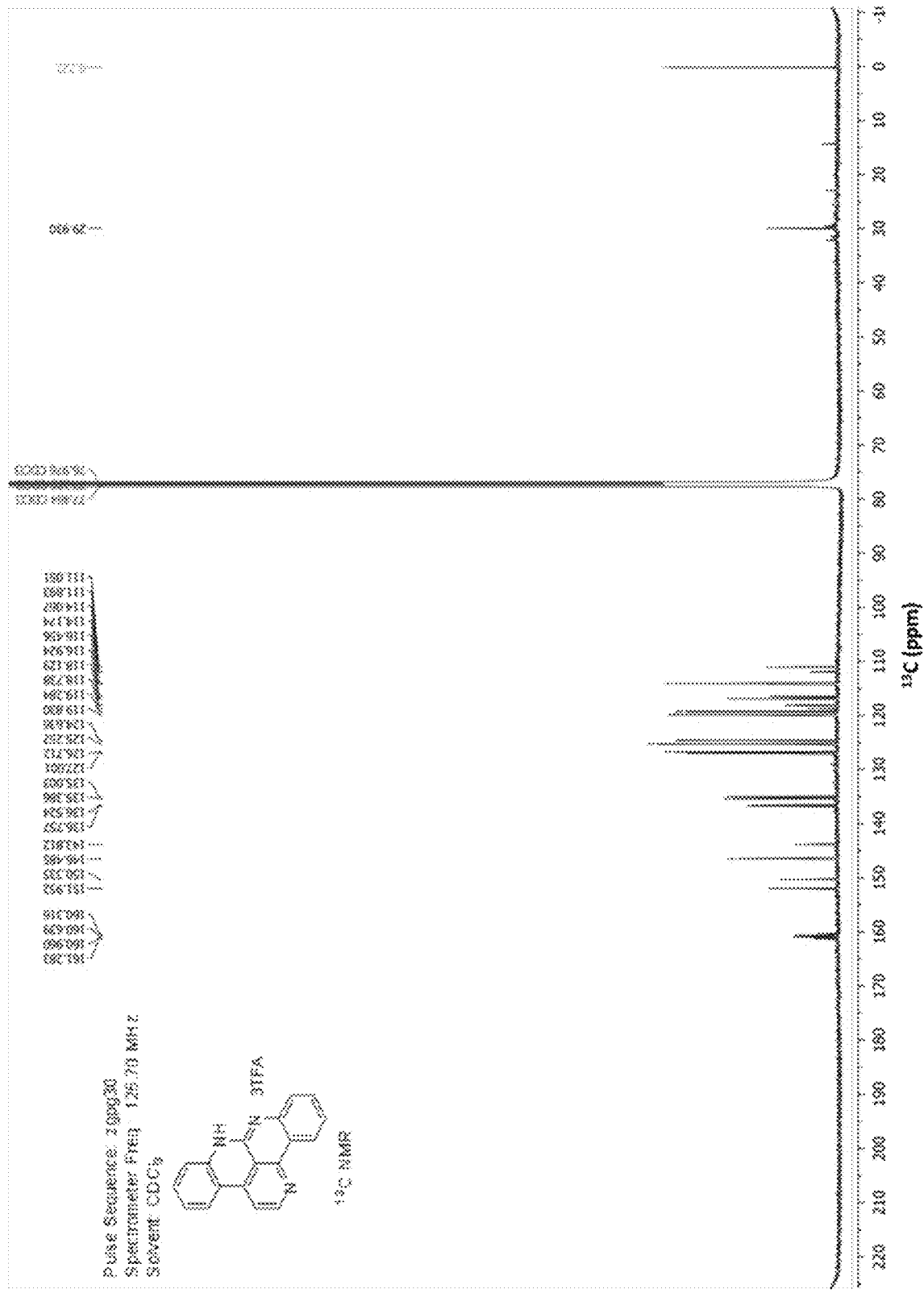
FIG. 19 shows $^{13}$C NMR spectrum for the TFA salt of synthesized Compound 4.
Figure 20:
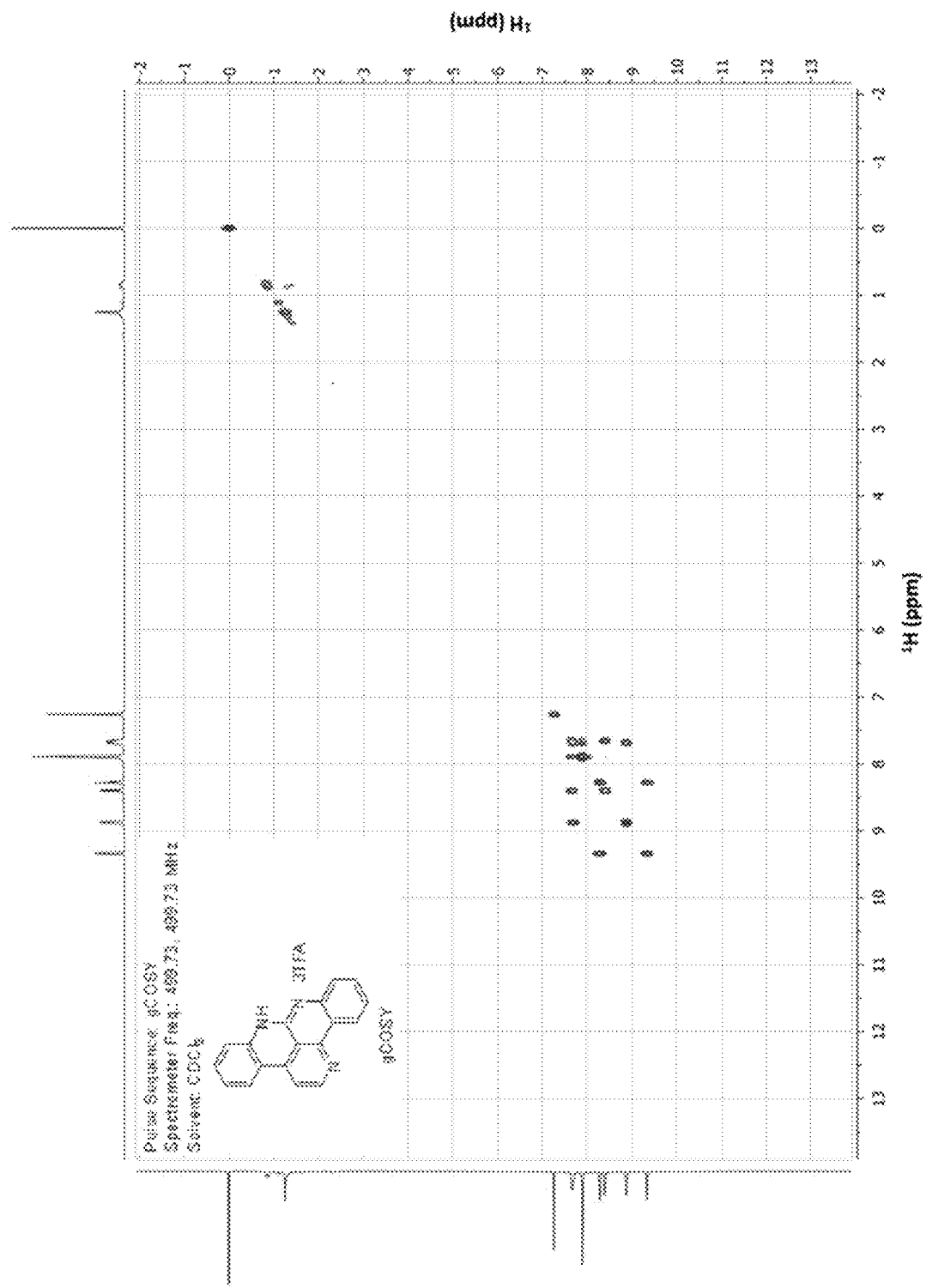
FIG. 20 shows $^1$H COSY NMR spectrum for the TFA salt of synthesized Compound 4.
Figure 21:
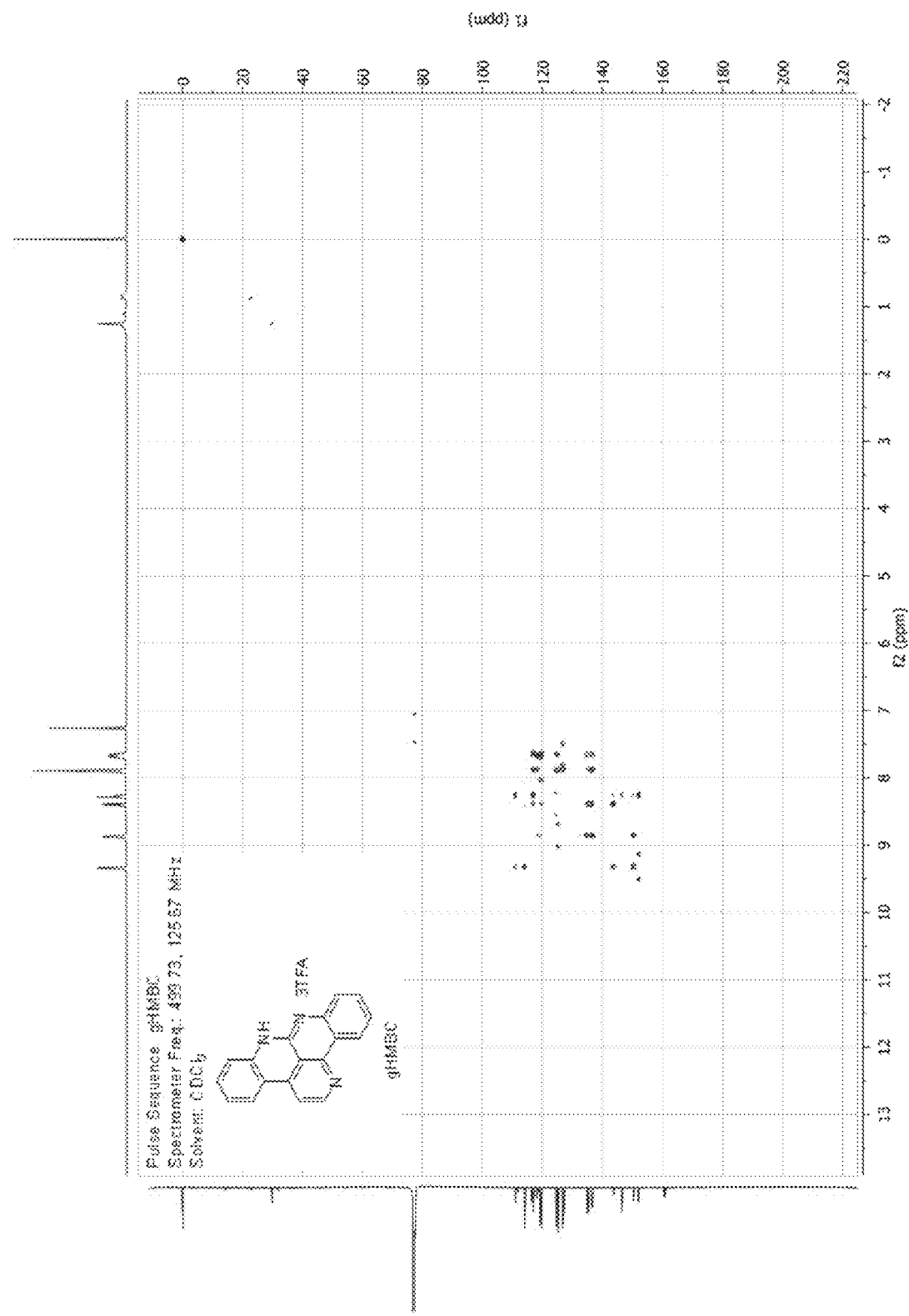
FIG. 21 shows $^1$H, $^{13}$C HSQC NMR spectrum for the TFA salt of synthesized Compound 4.
Figure 22:
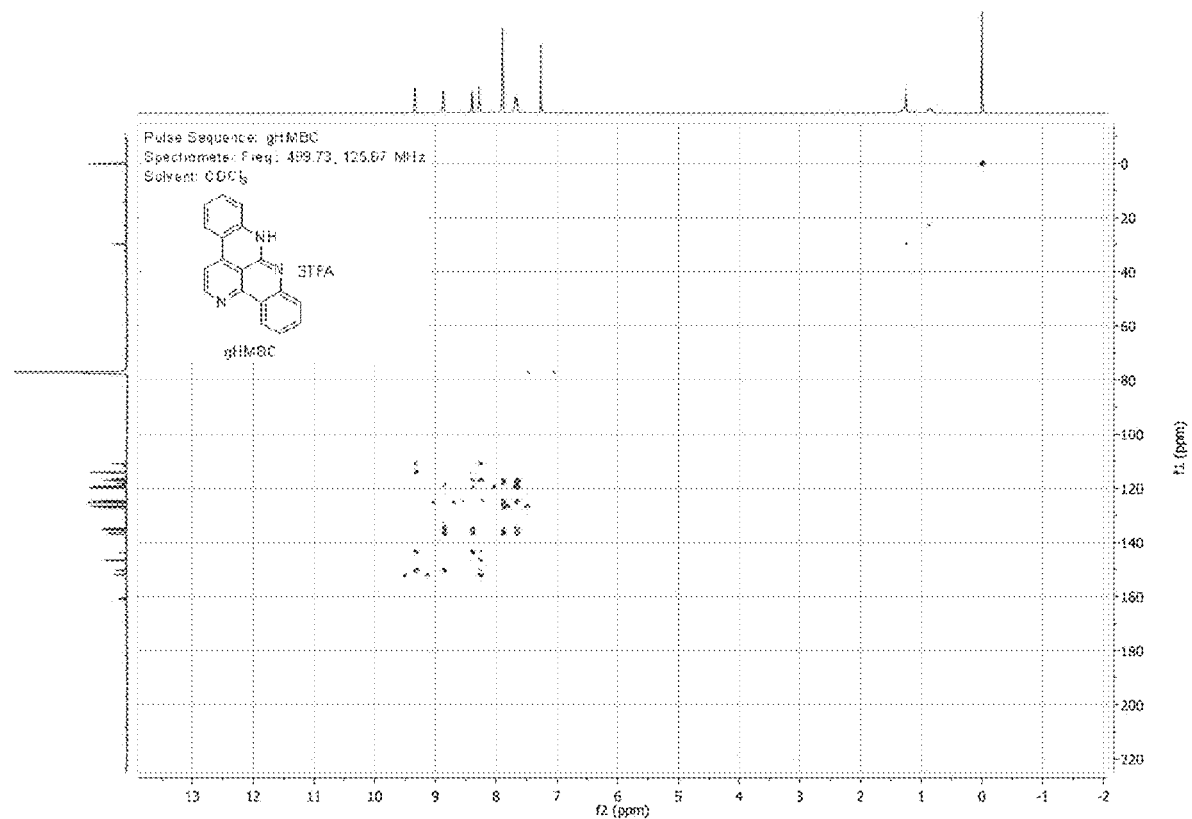
FIG. 22 shows HMBC NMR spectrum for the TFA salt of synthesized Compound 4.
Figure 23:
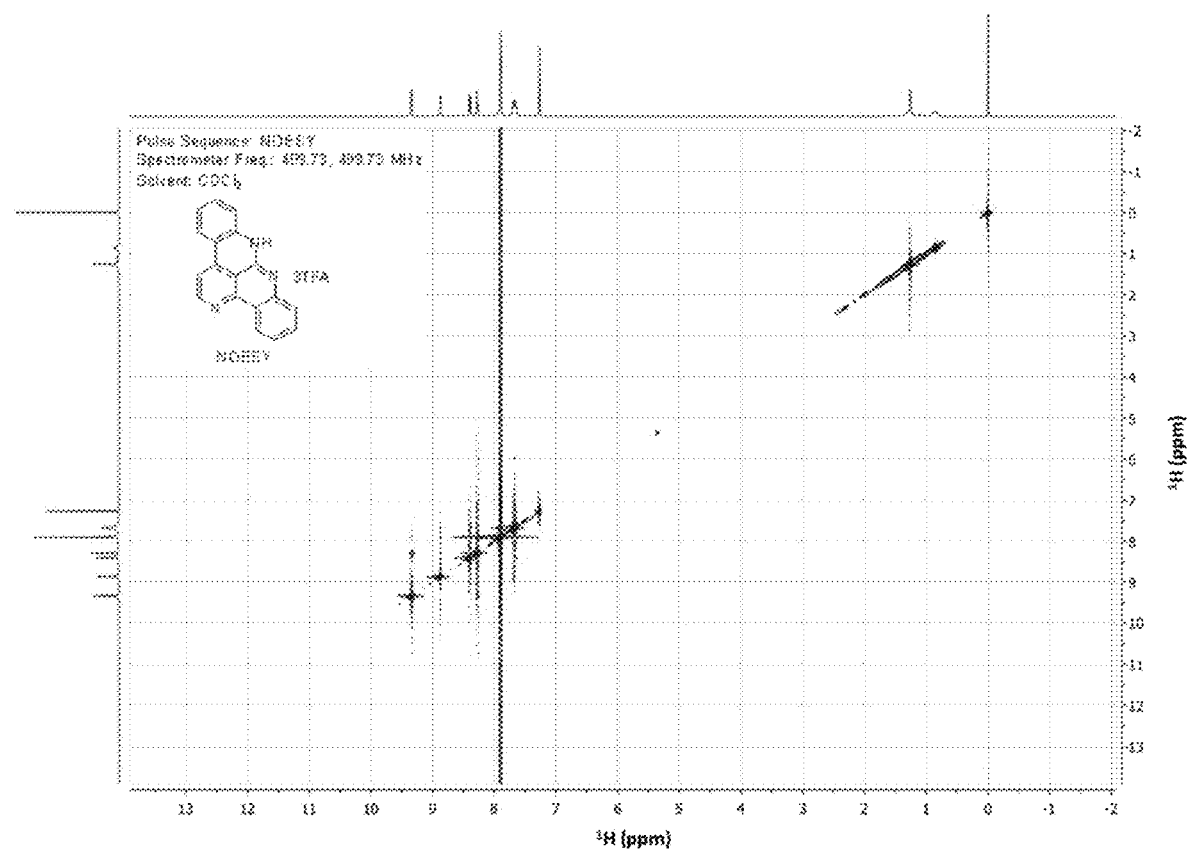
FIG. 23 shows NOESY NMR spectrum for the TFA salt of synthesized Compound 4.
Figure 24:
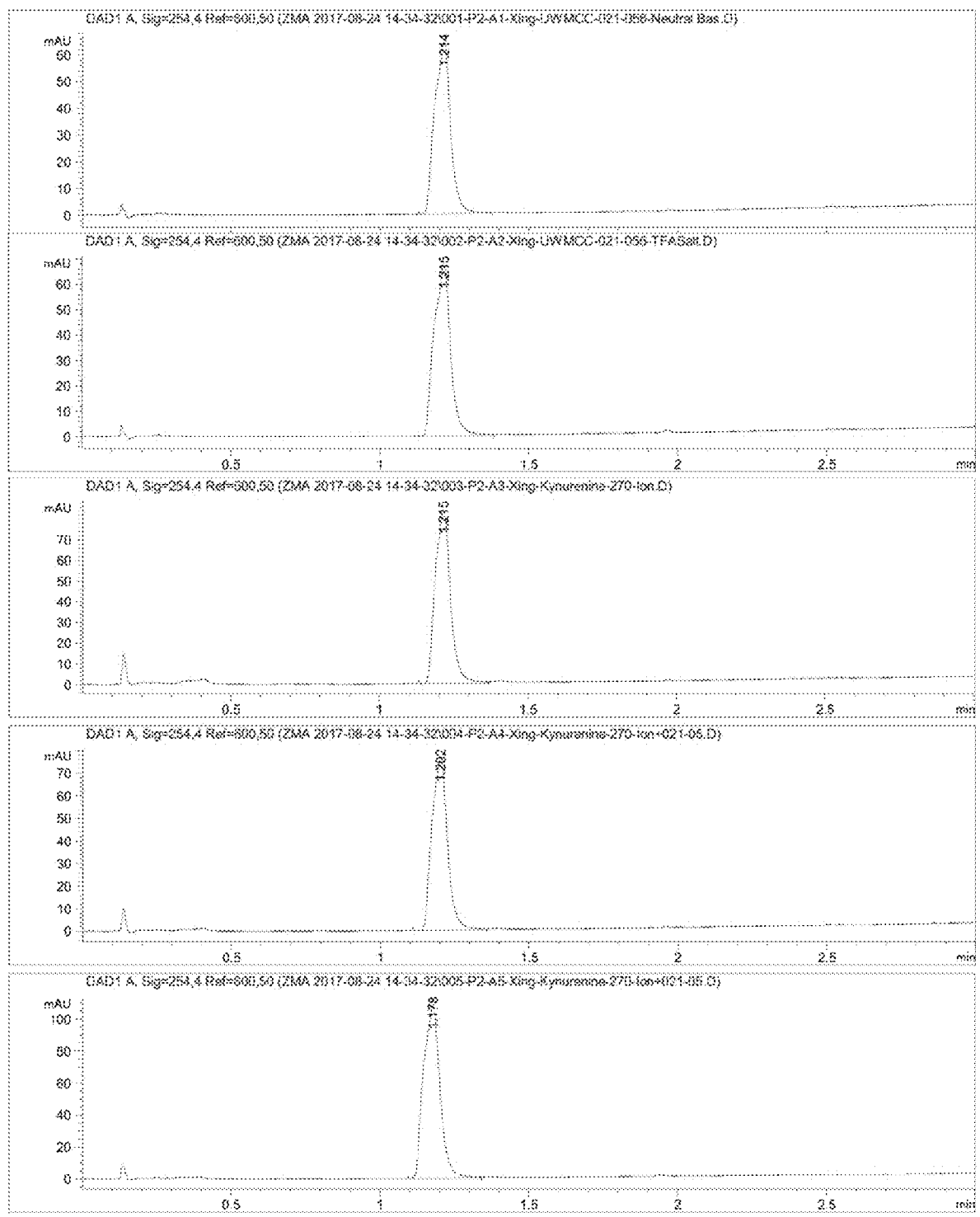
FIG. 24 shows LC-MS analysis of the TFA salt form and the free base of compound 4 with the isolated 270 ion. From top to bottom: the free base, the TFA salt, the isolated 270 ion, mixture of the free base with the isolated 270 ion, mixture of the TFA salt with the isolated 270 ion, mixture of the TFA salt with the free base, mixture of the TFA salt, the free base and the isolated 270 ion.
Figure 24:
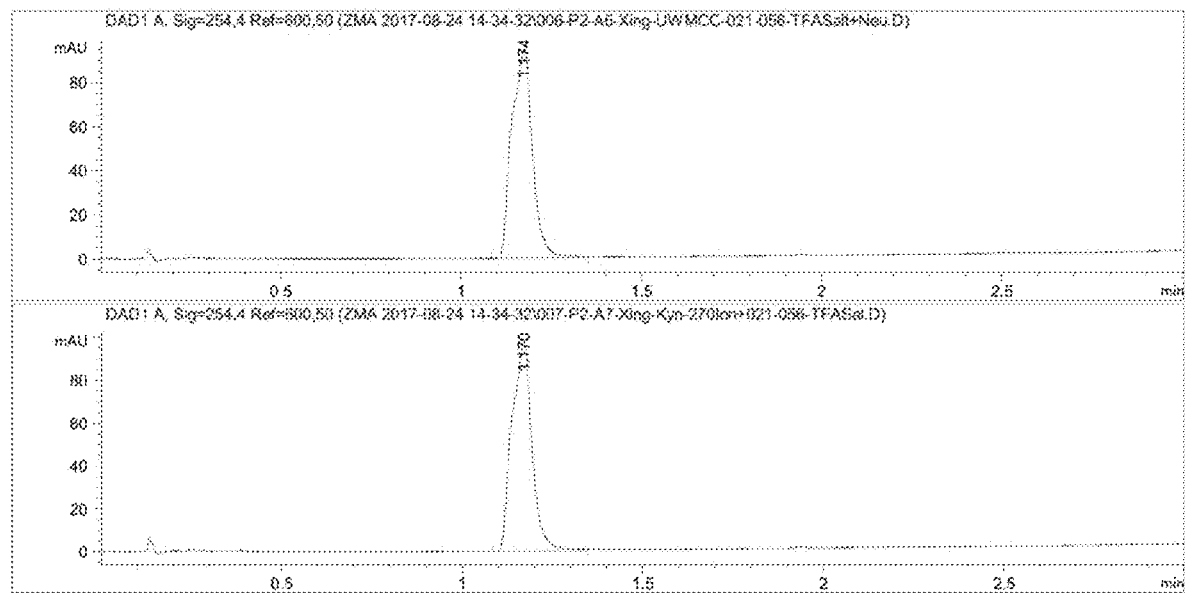
Figure 25:
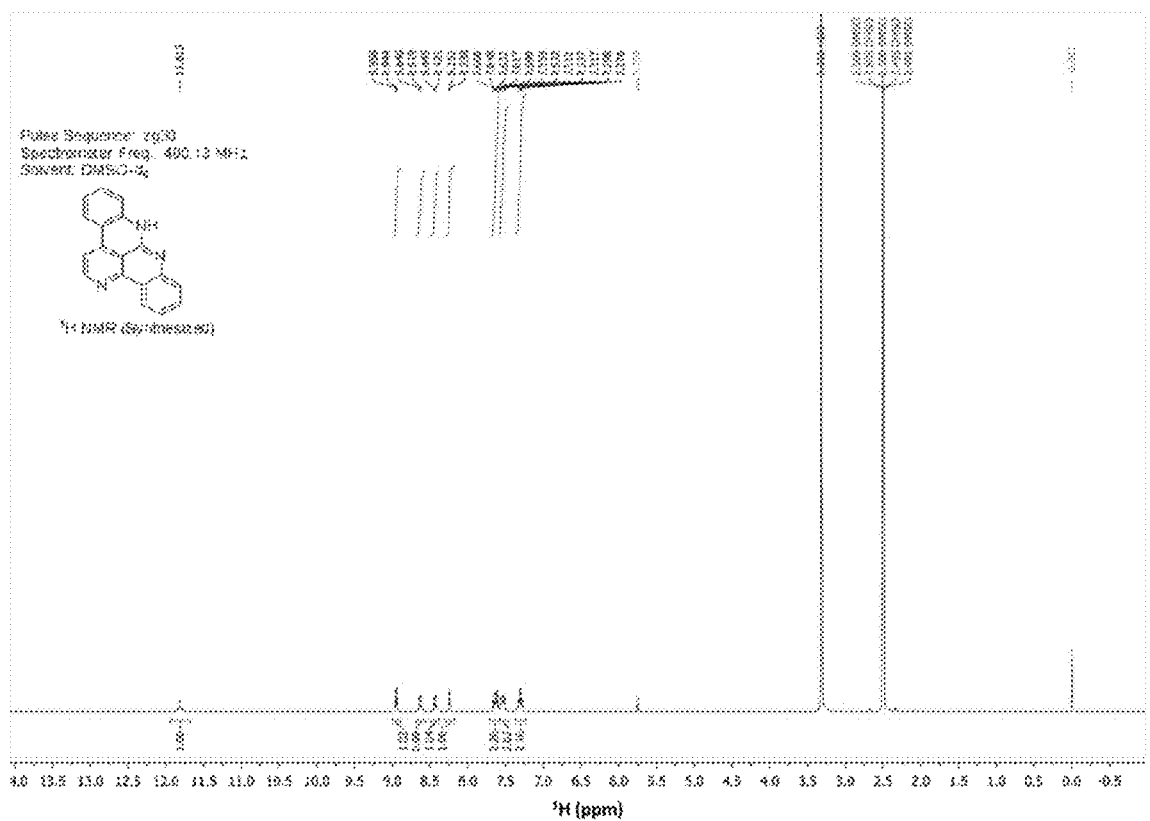
FIG. 25 shows $^1$H NMR spectrum for the synthesized Compound 4 free base.
Figure 26:
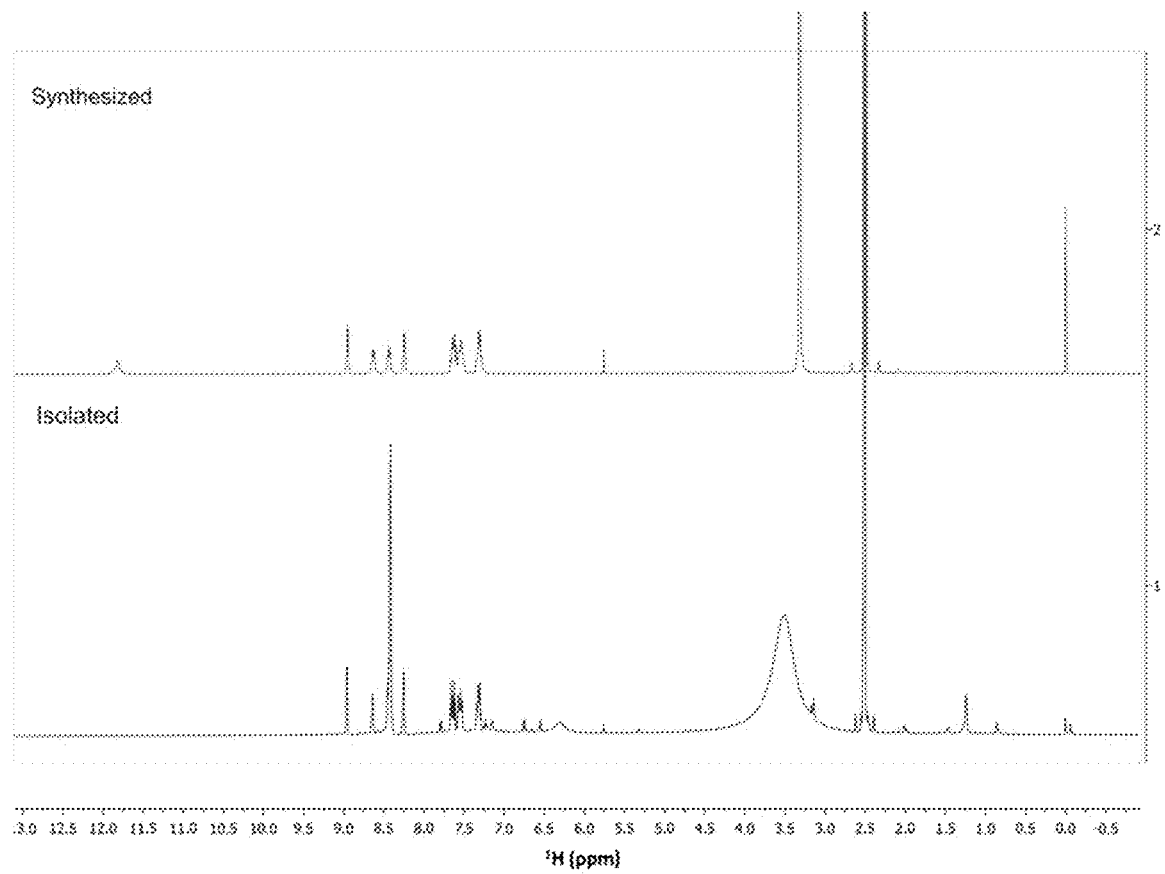
FIG. 26 shows comparison of the $^1$H NMR spectra of the synthesized Compound 4 free base and the isolated 270 ion (in DMSO-d$_6$).

To confirm the predicted structure of TEACOP270 (FIG. 5a), a chemical synthesis was performed (Compound 4, FIG. 5b). The TFA salt of the synthesized compound 4 showed good solubility in CDCl$_3$ and thus was fully characterized (FIG. 17-23). Similar to that of the purified TEACOP270, we were not able to fully characterize the free base form of compound 4 due to the poor solubility, but compound 4 clearly showed an almost identical $^1$H NMR spectrum to that of the purified TEACOP270 except for the N—H proton (FIGS. 25-26 & 12). The difference in N—H proton is likely due to lipid contamination in the purified TEACOP270 sample (FIGS. 12-16) or different levels of water molecules in the two samples. Furthermore, the purified TEACOP270, the synthesized free base compound 4 and its TFA salt were compared by LC-MS analysis, and the observed single peak from mixtures of each two as well as a mixture of the three apparently showed that the synthesized compound 4 was identical to the purified TEACOP270 (FIG. 24).

We further showed that Compound 4 and the purified TEACOP270 exhibited the same structural signatures in AHR induction except that the measured activity of the purified TEACOP270 is more than 10-fold lower than that of Compound 4 (FIG. 5c). The lower activity of the purified TEACOP270 is consistent with the fact that the sample was largely contaminated by lipids (FIGS. 12-16). Similar to the fresh and activated kynurenine (FIGS. 1-2), the activity of both Compound 4 and the purified TEACOP270 in AHR induction was barely affected by the AHR Q377A mutation, but drastically affected by T285A mutation (FIG. 5c).

Discussion

In addition to serving as energy sources and building blocks for metabolic pathways, cellular metabolites are increasingly recognized as key signaling molecules governing many aspects of cellular and physiological functions. Signaling metabolites are thought to serve as neurotransmitters (O'Mahony, Clarke et al. 2015), ligands of G-protein coupled receptors and nuclear receptors to induce signaling cascades (Jonker, Suh et al. 2012, Ahmadian, Suh et al. 2013, Husted, Trauelsen et al. 2017), inflammatory responses (Serhan 2014, Yore, Syed et al. 2014), regulation of enzymes for metabolic control (Li, Gianoulis et al. 2010), or the production of tumorigenic on cometabolites (Santagata, Eberlin et al. 2014). Despite their functional importance, signaling metabolites are often present at low abundance and are transient in nature, making identification and characterization of such metabolites highly challenging. Complex chemistry and biological endpoints further hinder the discovery of true signaling molecules among complex metabolites, such as kynurenine. Although kynurenine was increasingly implicated in many aspects of biological function, based upon its structure, its true role in AHR activation remained highly puzzling.

Understanding the mode of interaction of endogenous ligands to AHR is also challenging due to the large diversity of AHR ligand structural and chemical properties. While both FICZ and kynurenine are potent AHR activators, the structure of FICZ resembles prototype AHR ligands; while kynurenine is much smaller, more polar, and has very few structural signatures of known AHR ligands (FIG. 6). The ligand-binding pocket of AHR is highly hydrophobic and many of its hydrophobic residues, Phe281, Phe289, Pro291, Leu302, Tyr304, Phe318, Ile319, Cys327, Met334, Met337, Phe345, Leu347, Val357 and Ala375, have been identified to be important for ligand binding (Procopio, Lahm et al. 2002, Bisson, Koch et al. 2009, Pandini, Soshilov et al. 2009, Xing, Nukaya et al. 2012). It seems unlikely that a largely polar and charged molecule such as kynurenine could fit into the hydrophobic ligand-binding pocket of AHR.

By harnessing a novel and powerful combination of research approaches, including structural modeling, binding signatures, cell biology, small molecule chemistry, advanced MS technologies, and NMR spectroscopy, we identified two novel TEACOPs of kynurenine with high potency at low picomolar concentrations in AHR activation and elucidated their structural and chemical basis in AHR. Given that these active derivatives are present in only trace amounts in kynurenine mixtures (FIG. 3a-b), it is not too surprising that the two novel AHR ligands had not been previously identified among either cellular kynurenine metabolites (Leklem 1971, Stone and Darlington 2002, Bohar, Toldi et al. 2015, Hubbard, Murray et al. 2015) or in vitro chemical derivatives (Brown and Becher 1967, Tokuyama, Senoh et al. 1967, Zelentsova, Sherin et al. 2013). Furthermore, neither cellular metabolites (Mezrich, Fechner et al. 2010) nor in vitro derivatives (FIG. 10) of kynurenine possess the level of AHR induction activity of even fresh kynurenine, not to mention their comparison with activated kynurenine (FIG. 2a). While the compounds we identified in this study might account for the AHR induction activity of kynurenine in mammalian cells, the chemical reaction schemes of kynurenine that lead to active AHR ligands (FIG. 5a) might occur by modified pathways in complex cellular environments. For example, kynuramine and 5-hydroxykynuramine, other cellular metabolites of tryptophan (Stone and Darlington 2002), might provide the active amine group in place of kynurenine for the first intermolecular Michael addition to deaminated kynurenine (FIG. 5a).

The fact that both fresh and activated kynurenine activate the B- and D-alleles of mAHR in vitro (FIG. 2d) is consistent with a role of these trace derivatives of kynurenine as endogenous AHR ligands. Human AHR is similar to the D-allele of mAHR, which is much less active or inert to many environmental ligands, such as BaP (FIG. 8a). Different endogenous ligands may be involved in different physiological functions. Both FICZ and kynurenine have been suggested in regulation of immune cells, but with distinctively different roles (Mezrich, Fechner et al. 2010, Nguyen, Kimura et al. 2010, Singh, Singh et al. 2016). An additional tryptophan metabolite, 2-(1'H-indole-3'-carbonyl)-thiazole-4-carboxylic acid methyl ester (ITE) was found to play a role in regulating cancer stem cells (Cheng, Li et al. 2015), potentially through AHR as AHR was demonstrated to play a role in regulation of the expansion of hematopoietic stem cells (Boitano, Wang et al. 2010).

Figure 27:
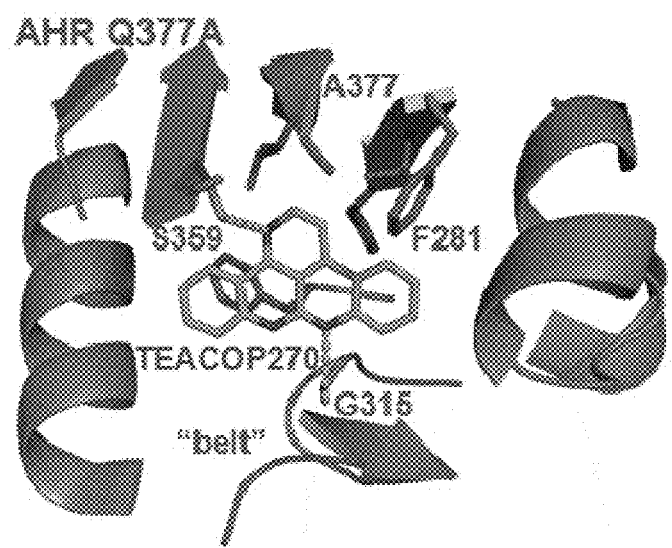
FIG. 27 shows structural model of the 270 ion bound to AHR-LBD Q377A. Key residues of AHR is shown in stick and colored by atom type. Intermolecular H-bonds are in cyan dashed line. The 270 ion are in stick and colored green and by atom type.

Besides the hydrophobic nature of the AHR ligand binding cavity, our previous study identified key structural signatures for several important aspects of AHR-ligand interactions (Xing, Nukaya et al. 2012). For example, Gln377 defines medial H-bond interactions and the preferences of AHR toward small medial extension of AHR ligands; His285 defines an H-bond network in controlling the overall shape of the ligand binding cavity (Xing, Nukaya et al. 2012). Furthermore, the "belt" and other flexible structural elements allow AHR to recognize diverse ligands with distinctly different shapes and chemical properties (Xing, Nukaya et al. 2012). These structural signatures also helped us understand AHR interaction with kynurenine derivatives and FICZ. We docked the chemical structure of TEACOP270 to our previous model of AHR-LBD (FIG. 5d). The predicted binding energy of the structure is much higher than that for single kynurenine (FIG. 1b), and close to that for FICZ (FIG. 7a). Examination of the docked model supports the structural signatures in AHR-ligand interactions revealed by mutagenesis analysis. While TEACOP270, which is highly similar to other TEACOPs identified here, forms more medial H-bond interactions with AHR than FICZ does (FIGS. 5d, 7a), the Q377A mutation reduced FICZ activity by five-fold (FIG. 7c), but barely affected the activity of TEACOPs in AHR induction (FIGS. 2c, 5c). This is likely due to that the smaller size and polarity of Q377A allows residue 377 to accommodate the larger, less polar medial edge of TEACOP270 so its polar edge forms H-bond interactions with the belt backbone carboxylate group of AHR (FIG. 27). This mode of ligand flipping would not happen for FICZ because Q377A would not allow residue 377 to accommodate the larger, polar edge of FICZ that faces the AHR belt for wild type AHR (FIG. 7a). Our study here provides important structural and chemical basis for further understanding of trace tryptophan metabolites in broad human physiology.

The ability of kynurenine to activate AHR D-allele is consistent with its critical role in human physiology. Our recent advance in understanding the structural basis of AHR signaling revealed a versatile allosteric structural pathway from AHR-LBD to the N-terminal nuclear localization signal and DNA-reading head (43). Based on directionality of H-bonds, the extensive H-bond interactions of TEACOPs to AHR-LBD (FIG. 5D) are expected to induce a more defined conformation in AHR-LBD than BaP. The latter interacts with AHR by only hydrophobic contacts (18). This likely explains why the maximum activity of kynurenine is 60% higher than BaP (FIG. 2A). Reduced structural dynamics of TEACOPs-bound AHR-LBD might also account for the distinct role of kynurenine in broad physiological functions. Our study here provides important structural and chemical basis for further understanding of kynurenine in broad human physiology.

Materials and Methods

Modeling AHR-LBD Bound to FICZ, Kynurenine, and Kynurenine Derivatives

Built our previous model of AHR-LBD, single FICZ, kynurenine, and kynurenine derivatives (KD274s, KD270s) were docked to the AHR ligand binding cavity using the Autodock program (Goodsell, Morris et al. 1996). This was followed by energy minimization and optimization of backbone conformation and rotamer usage. Iterative model building, ligand docking, energy minimization, and optimization of backbone conformation and rotamer usage were performed until satisfying results were obtained.

Cloning and Expression of Recombinant mAHR

The wild type and mutant mAHR were cloned into the XhoI/SalI cloning sites of pTARGET (Promega, Madison, Wis.) using routine PCR and molecular cloning procedures using the pSport-mAHR plasmid (PL65) as template (Dolwick, Swanson et al. 1993). For recombinant expression of mAHR, COS-1 cells were cultured in 6 cm dishes and transfected with 2 μg of wild-type or mutant mAHR expression vector. Twenty-four hours after transfection, cells were collected, and the whole cell extracts were prepared by celLytic M reagent (Sigma-Aldrich, St Louis, Mo.). 100 μg of whole cell extract was analyzed by western blot using antibodies that specifically recognize the mAHR (bear-2) and β-actin (Sigma).

Luciferase Reporter Gene Assay

COS-1 cells were cultured in 96-well plates and transiently transfected with pTarget vector containing the expression cassette of wild-type or mutant mAHR, or empty vector (3 ng), together with pGudLu6.1 DREs-driven luciferase reporter vector (14 ng) (Han, Nagy et al. 2004) and TK-renilla luciferase vector (3 ng) (Invitrogen, Carlsbad Calif.). Six hours after transfection, cells were treated with titrated or fixed concentrations of FICZ, kynurenine, BaP, or vehicle alone (0.1% DMSO) for four hours (or 20 hours when specifically indicated), and assayed with the dual luciferase reporter assay system (Promega, Madison, Wis.). The expressed luciferase activity was measured by ENSPIRE plate reader (Perkin Elmer, USA). Data analysis and simulation of dose response curves were performed using GraphPad Prism 5 (GraphPad software Inc., La Jolla, Calif.). The experiments were performed in triplicate and repeated at least three times. Representative results of one repeat are shown as mean±SEM.

Kynurenine Sample Preparation and Phase Separation

Fresh crystalline kynurenine (Sigma-Aldrich, MO, USA) was dissolved in DMSO at a concentration of 10 mg/ml, and incubated at 37° C. for 3 days, followed by temporary or long-term storage at −20° C. To separate derivatives of kynurenine, kynurenine with 3-day incubation was diluted with water to a concentration of 1 mg/ml and mixed thoroughly with equal volume of dichloromethane (DCM) by shaking in a separator funnel. The two phases (aqueous upper layer/organic bottom layer) are clearly separated after one-hour standing still. The bottom layer was collected for further fractionation by HPLC.

High Pressure Liquid Chromatography (HPLC)

The combined DCM phases from phase separation for 200 mg or 2 grams of incubated kynurenine were concentrated under reduced pressure with Buchi Rotavapor R-300 to generate a crude mixture with some DMSO residue. The crude mixture was then purified using the Teledyne Isco CombiFlash EZprep system with a RediSep Prep C18 column (particle size 5 μm, size 20×150 mm) via mass-directed fractionation (phase A: 0.1% Formic acid/5% $CH_3CN$ in $H_2O$, phase B: 0.1% Formic acid in $CH_3CN$, flow rate 18 mL/min, gradient (B %): 0-1 min 10%, 1-21 min 10-100%, 21-23 min 100%). For the 200 mg pilot test, the AHR induction activity of each fraction was tested and an initial prediction of the compounds associated with activity was made based on MS ions in the active fractions. For large-scale fractionation, the 274 and 270 ion fractions were collected, combined, and dried in a Genevac EZ-2 Elite centrifugal evaporator at 30° C. The resulting product (ca. 30 mg) was further purified (five repeated injections) on Agilent 1200 series HPLC with an Eclipse XDB-C18 column (particle size 5 μm, size 9.4×250 mm, phase A: 0.1% Formic acid/5% $CH_3CN$ in $H_2O$, phase B: 0.1% Formic acid in $CH_3CN$, flow rate 2 mL/min, gradient (B %): 0-4 min 5%, 4-42 min 10-50%, 42-44 min 50-100%, 44-50 min 100%). Fractions were collected based on UV absorption at 254 nm.

The fractions with significant absorption were dried in the Genevac EZ-2 Elite at 30° C. Mass analysis of the resulting dry materials was performed on Waters Autopure system with QDa ESI Mass Spectrometer.

High Resolution Mass Spectrometry (HRMS) and LC-MS

For the initial investigation of kynurenine conversion to active products, we used mass spectrometry to analyze fresh kynurenine, and kynurenine after 3-day incubation at 37° C. Samples were diluted 1:1000 and infused into a Bruker MaXis 4G ultra-high resolution time-of-flight mass spectrometer (Bruker Daltonic, Billerica Mass.). Samples were infused at 3 microliters/minute and spectra were collected in positive mode for 2 minutes. For data analysis, we averaged spectra for >1 minute and manually compared peaks in each sample.

For subsequent relative quantitation we compared the area under the curve (AUC) of peaks of interest from samples of fresh kynurenine, kynurenine after 3-day incubation at 37° C. (3 d), and kynurenine with 3-day incubation at 37° C. followed by storage at −20° C. for 6 months (3 d, 6 m) following LC-MS (liquid chromatography coupled to mass spectrometry) analysis. Samples were diluted 1:3000 in solvent containing an internal standard (100 ng/ml $D_3$-naproxen) prior to separation on a Waters Acquity UPLC system (Waters Corp. Milford Mass.) and then analyzed on the MaXis. Samples (5 microliters) were injected on a 2.1×100 mm Kinetex XB-C18 column (Phenomenex, Torrance Calif.) with 2.6 micron particles equipped with a guard column. Analytes were separated using an increasing gradient of acetonitrile in LC separation created by solvent A, water with 0.1% formic acid (v/v), and solvent B, acetonitrile with 0.1% formic acid, at a flow rate of 0.3 ml/minute. The gradient was started with 2% B held for 2 minutes, followed by a gradient to 75% B in 15 minutes and ramp to 95% B in 1 minute. Spectra were collected over a mass range of 50 m/z to 1750 m/z. All data were analyzed using Bruker Data Analysis software. Briefly, extracted ion chromatograms for masses of interest were created with a window of 0.005 m/z and areas for peaks of interest were determined using the software. Peak areas were determined from two replicate reactions and each was injected twice (technical replicates). Areas of kynurenine mother ions and ions of interest were normalized to the AUC for the internal standard. The relative area of each of the two ions of interest was then normalized to the relative kynurenine area in the same run to determine the percent abundance of the new compounds.

Ultrahigh Resolution Fourier Transform Mass Spectrometry (FTMS)

Samples containing the 274 and 270 ions were diluted to 10-20 ng/mL in acetonitrile, and diluted samples were direct-infused to a 12T solariX FTMS (Bruker Daltonics) by a TriVersa NanoMate (Advion) with spray voltage of 1300 V and gas pressure of 0.25 psi. The FT data size was set to 8M (3.5 s transient length, 1.39M resolving power at m/z 274 and 270, respectively). The isotopic clusters were isolated in a 5-8 m/z window. The experimental spectra were averaged by 50-200 scans. The MS results were analyzed by SmartFormula manually integrated in the DataAnalysis software (Bruker Daltonics). The mass tolerance was set to 2 ppm. Only one candidate was found for each sample and the theoretical isotopic distribution was compared to the experimental data.

Nuclear Magnetic Resonance Spectrometry (NMR)

The fraction with the stable 270 ion of kynurenine derivatives from large scale purification was examined by NMR. $^1$H NMR and related 2D-NMR spectra were recorded on a Bruker Avance III 600 instrument. Chemicals shifts are reported in ppm by comparing to DMSO-$d_6$ ($\delta$=2.50 ppm for $^1$H NMR). $^1$H NMR (600 MHz, DMSO-$d_6$) detected all aromatic protons: $\delta$ 8.95 (d, J=5.4 Hz, 1H), 8.63 (d, J=7.8 Hz, 1H), 8.44 (d, J=7.8 Hz, 1H), 8.25 (d, J=5.4 Hz, 1H), 7.65 (dd, J=7.8, 7.8 Hz, 1H), 7.62 (dd, J=7.8, 7.8 Hz, 1H), 7.56 (d, J=8.4 Hz, 1H), 7.53 (d, J=8.4 Hz, 1H), 7.32 (dd, J=6.0, 7.2 Hz, 1H), 7.30 (dd, J=6.0, 6.0 Hz, 1H), 6.30 (brs, 1H, H—N). Based on the COSY spectrum, there are three sets of protons detected: a) Protons 8.95 and 8.25; b) Protons 8.63, 7.30, 7.62 and 7.53; c) Protons 8.44, 7.32, 7.65 and 7.56. These results are consistent with the structure of the 270 ion.

Chemical Synthesis and NMR Characterization

All reactions were performed in purchased 8-mL vials or flame-dried glassware under Ar atmosphere. Solvents were distilled prior to use. Reagents were used as purchased unless otherwise noted. Chromatographic separations were performed on Teledyne Isco CombiFlash Rf 200 or EZprep systems. $^1$H, $^{13}$C and 2D-NMR spectra were obtained on Varian VI-500, Bruker Avance III 400 or 600 MHz spectrometers. Chemical shifts are reported in ppm by comparing to solvent residue signals ($\delta$=7.26 ppm in $^1$H NMR and $\delta$=77.23 ppm in $^{13}$C NMR for CDCl$_3$ and $\delta$=2.50 ppm in $^1$H NMR and $\delta$=39.51 ppm in $^{13}$C NMR for DMSO-$d_6$). Melting points were determined using a SRS OptiMelt system and are uncorrected/calibrated. TLC analysis was performed using Aldrich 254 nm polyester-backed plates (60 Å, 250 μm) and visualized using UV following KMnO$_4$. stains. Low-resolution mass and LC-MS spectra were obtained using a Waters Autopure system with QDa ESI Mass Spectrometer or an Agilent 1290 Infinity II system with 6120 Quadrupole Mass Spectrometer with Multimode (ESI+ APCI) source.

Specifically for the synthesis of Compound 4, to a 100-mL three-necked round bottom flask equipped with a condenser was added tert-butyl (2-(4,4,5,5-tetramethyl-1,3,2-dioxaborolan-2-yl)phenyl)carbamate 1 (418 mg, 1.31 mmol), methyl 4-bromo-2-chloronicotinate 2 (150 mg, 0.60 mmol), Pd(PPh$_3$)$_4$ (69 mg, 0.06 mmol) and Na$_2$CO$_3$ (253 mg, 2.39 mmol). The flask was evacuated under high vacuum for 1-2 mins and refilled with Argon. The vacuum purge procedure was repeated three times. Then H$_2$O (1.2 mL), EtOH (0.6 mL) and toluene (12 mL) were added successively and the reaction was stirred at 100° C. overnight. The reaction mixture was then concentrated under reduced pressure to remove all the volatiles and the residue mixture was loaded directly on a celite cartridge and purified on CombiFlash with RediSep Gold silica column Hexane/EtOAc to give a pair of two inconsequential isomers (major 114 mg, 49% and minor 36 mg, 16%).

Major product: white solid, mp 366-369° C. (decomposition happened); $R_f$=0.50 (CH$_2$Cl$_2$/EtOAc=3/1), $^1$H NMR (400 MHz, CDCl$_3$) $\delta$ 11.64 (s, 1H), 9.05 (d, J=4.4 Hz, 1H), 8.81 (dd, J=1.6, 8.0 Hz, 1H), 7.99 (d, J=7.6 Hz, 1H), 7.55-7.48 (m, 2H), 7.38-7.34 (m, 2H), 7.21 (ddd, J=1.2, 7.6, 7.6 Hz, 1H), 7.08 (dd, J=1.6, 7.6 Hz, 1H), 6.83 (dd, J=1.2, 8.0 Hz, 1H), 6.13 (s, 1H), 1.31 (s, 9H); $^{13}$C NMR (100 MHz, CDCl$_3$) $\delta$ 163.0, 153.7, 153.4, 153.1, 149.5, 137.4, 135.6, 131.7, 128.5 (2 carbons), 126.1, 125.3, 123.9, 123.4, 119.9, 119.3, 116.3, 80.6, 28.4; HRMS (QTOF MS ESI) m/e calcd for C$_{23}$H$_{22}$N$_3$O$_3$ [M+H]$^+$ 388.1656, found 388.1655.

Minor product: white solid, mp 230-234° C.; $R_f$=0.50 (CH$_2$Cl$_2$/EtOAc=1/1), $^1$H NMR (400 MHz, CDCl$_3$) $\delta$ 12.21 (s, 1H), 8.96 (d, J=5.6 Hz, 1H), 8.22 (dd, J=1.2, 8.4 Hz, 1H), 8.15 (d, J=5.6 Hz, 1H), 7.55 (ddd, J=1.2, 7.2, 7.2 Hz, 1H), 7.49 (ddd, J=2.0, 7.6, 7.6 Hz, 1H), 7.33 (ddd, J=1.2, 7.2, 7.2 Hz, 1H), 7.20 (dd, J=1.6, 7.6 Hz, 1H), 7.12 (ddd, J=1.2, 7.6, 7.6 Hz, 1H), 7.07 (brs, 1H), 6.89 (dd, J=1.2, 8.4 Hz, 1H), 1.37 (s, 9H); $^{13}$C NMR (100 MHz, CDCl$_3$) $\delta$ 162.0, 160.8, 153.1, 150.5, 144.0, 138.0, 135.7, 132.4, 130.2, 128.7, 123.6, 123.3, 122.8, 119.5, 117.5, 116.3, 115.5, 80.3, 28.5; HRMS (QTOF MS ESI) m/e calcd for C$_{23}$H$_{22}$N$_3$O$_3$ [M+H]+ 388.1656, found 388.1653.

To a solution of the major isomer from the previous step (60 mg, 0.15 mmol) in CH$_2$Cl$_2$ (5 mL) was added TFA (0.12 mL, 1.54 mmol) and the reaction was stirred at rt for 24 h before another portion of TFA (0.12 μL, 1.54 mmol) was added. The reaction mixture was further stirred for 24 h and then concentrated under reduced pressure to afford the desired product as a TFA salt which was fully characterized. Adding a drop of 2,2,2-trifluoroethanol to a solution of the TFA salt in CDCl$_3$ followed by comparing the integrations of the TFA salt to 2,2,2-trifluoroethanol in $^1$H/$^{19}$F NMR spectra revealed the salt was a complex of compound 4 with three equivalents of TFA.

To a solution of the TFA salt in CH$_2$Cl$_2$ (15 mL) was added 10 mL sat. aq. NaHCO$_3$ solution and the mixture was stirred vigorously for 10 min. The solid precipitated was collected via filtration and washed with H$_2$O, CH$_2$Cl$_2$ and a small amount of acetone, dried under vacuum to afford compound 4 as the free base (42 mg, quant).

The TFA salt of compound 4: yellow solid, mp 113-117° C.; $^1$H NMR (500 MHz, CDCl$_3$) δ 9.34 (d, J=6.0 Hz, 1H), 8.88 (d, J=8.0 Hz, 1H), 8.40 (d, J=8.0 Hz, 1H), 8.28 (d, J=6.0 Hz, 1H), 7.92-7.88 (m, 4H), 7.70-7.64 (m, 2H); $^{13}$C NMR (125 MHz, CDCl$_3$) δ 160.8 (q, J=40.6 Hz), 152.0, 150.3, 146.5, 143.8, 136.8, 136.5, 135.4, 135.0, 127.0, 126.7, 125.3, 124.6, 119.8, 119.3, 118.1, 116.9, 115.3 (q, J=286.8 Hz), 114.1, 111.1; $^{19}$F NMR (470 MHz, CDCl$_3$) δ −74.9; HRMS (QTOF MS ESI) m/e calcd for C$_{18}$H$_{12}$N$_3$ [M+H]+ 270.1026, found 270.1026.

The free base of compound 4: yellow solid, mp 324-328° C.; $^1$H NMR (500 MHz, DMSO-d$_6$) δ 11.81 (brs, 1H), 8.95 (d, J=7.0 Hz, 1H), 8.63 (d, J=10.5 Hz, 1H), 8.44 (d, J=10.0 Hz, 1H), 8.24 (d, J=7.0 Hz, 1H), 7.67-7.60 (m, 2H), 7.56-7.51 (m, 2H), 7.34-7.28 (m, 2H); HRMS (QTOF MS ESI) m/e calcd for C$_{18}$H$_{12}$N$_3$ [M+H]+ 270.1026, found 270.1026.

The free base of compound 4 (12.5 mg, 0.046 mmol, 90%) was also obtained with the same conditions from 20 mg of the minor isomer.

Based on the 1D/2D NMR data collected (FIG. 18-23), all the protons/carbons of the TFA salt were assigned (FIG. 17).

LC-MS analysis of the purified TEACOP270 and the synthesized Compound 4 LC-MS analysis of the purified 270 ion, the free base and TFA salt of the synthesized Compound 4 in isolation or in mixture were performed on an Agilent 1290 Infinity II/6120 Quadrupole LC/MS system with a Poroshell 120 EC-C$_{18}$ column (particle size 1.9 μm, size 2.1×50 mm, phase A: 0.1% Formic acid/5% MeOH in H$_2$O, phase B: 0.1% Formic acid in MeOH, flow rate 1 mL/min, gradient (B %): 0-0.2 min 35%, 0.2-2.5 min 35-100%, 2.50-2.95 min 100%, 2.95-3.0 min 35%).

Example 2: Synthesis Schemes of Compounds of the Present Invention

Figure 30:
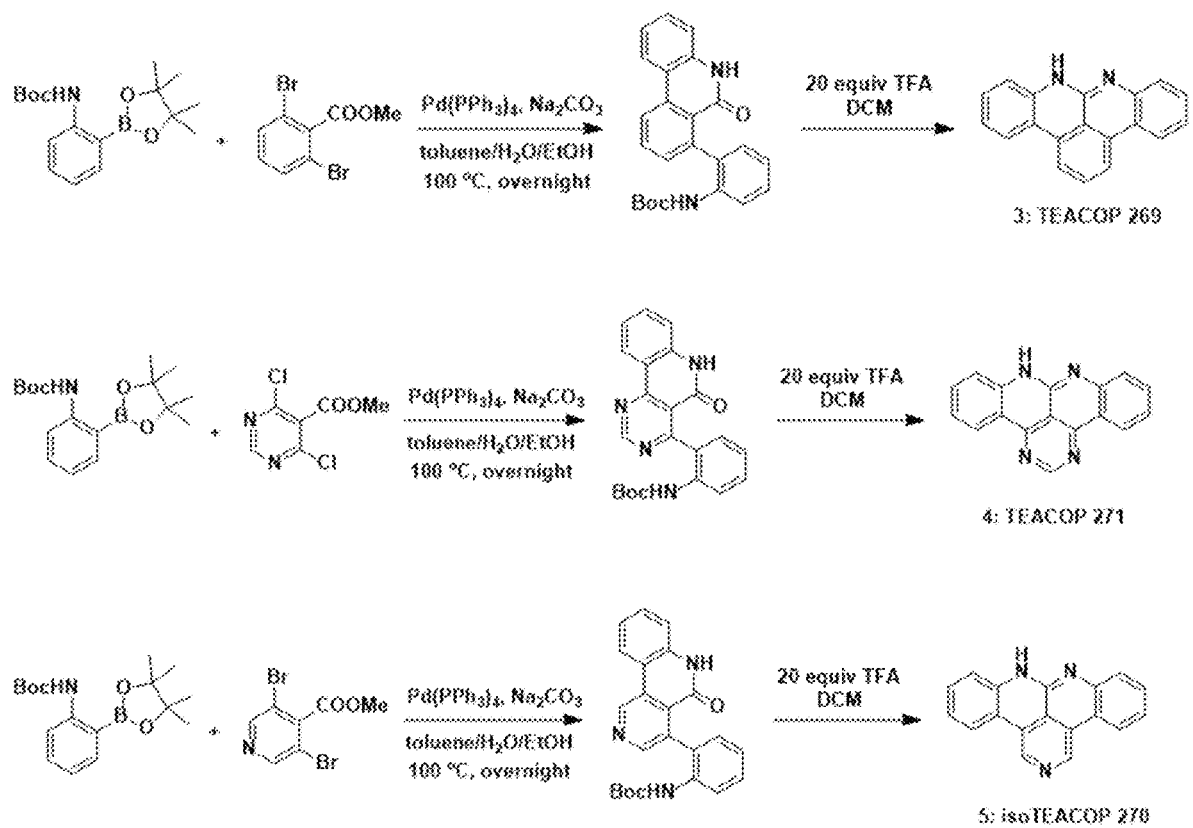
FIG. 30 shows synthesis schemes of TEACOPs with ring modifications.
Figure 31:
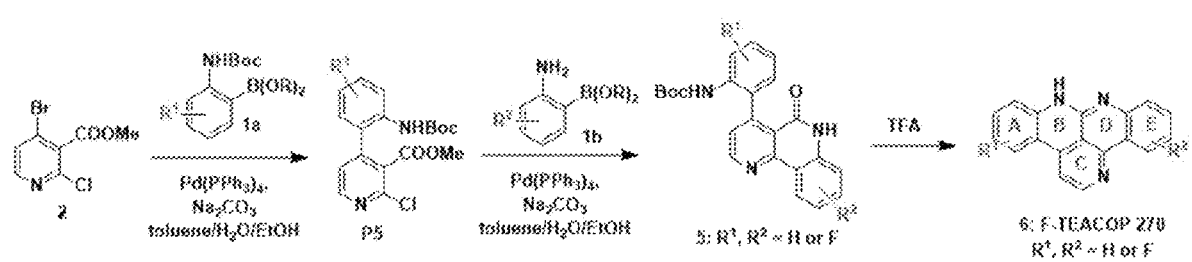
FIG. 31 shows synthesis schemes of fluoride derivatives.
Figure 32:
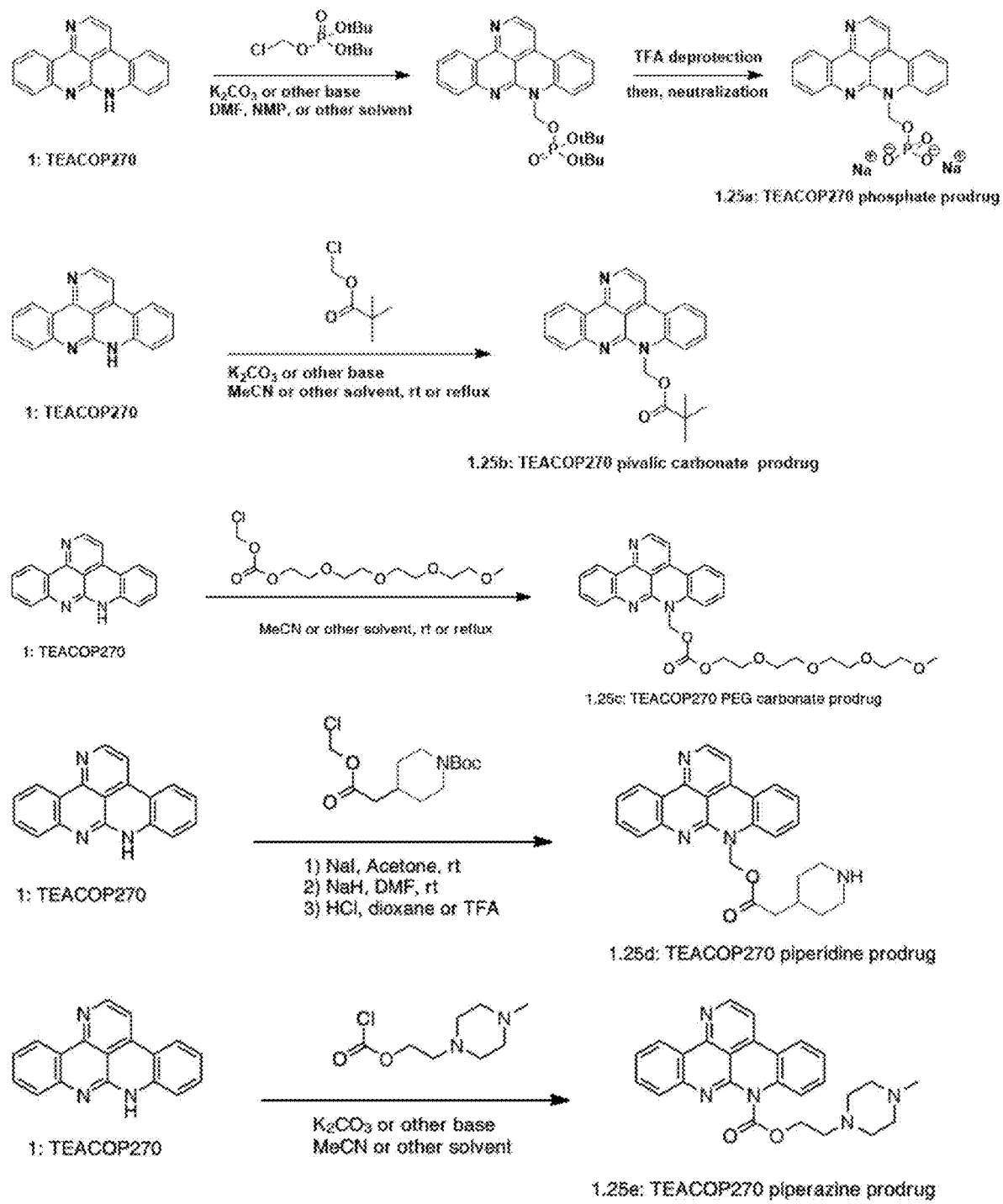
FIG. 32 shows synthesis schemes of exemplary prodrugs.

FIG. 29-32 show schemes for the synthesis of compounds of the present invention, including reduced form TEACOP 274 (FIG. 29), ring modifications (FIG. 30), fluoride derivatives (FIG. 31) and prodrugs (FIG. 32).

We envision TEACOP 274 can be produced by the cyclization pathway outlined in FIG. 29, or alternatively through a reduction of TEACOP 270.

Analogous to the synthesis of TEACOP 270, ring modified derivatives TEACOP 269, TEACOP 271, and isoTEACOP 270 can be produced using different di-halogenated aromatic esters for the Suzuki coupling, as shown in FIG. 30.

Fluoride derivatives of TEACOP 270 were produced using fluorinated building blocks 1a that were installed at the A ring when coupled to methyl 4-bromo-2-chloronicotinate 2 first, or 1b at the E ring when coupled second (FIG. 31). Specifically synthesis of 14-F-TEACOP 270 6a, a derivative of TEACOP 270 with fluorine atom on C14: to a 100-mL three-necked round bottom flask equipped with a condenser was added tert-butyl (2-(4,4,5,5-tetramethyl-1,3,2-dioxaborolan-2-yl)phenyl)carbamate 1 (865 mg, 2.71 mmol), methyl 4-bromo-2-chloronicotinate 2 (620 mg, 2.47 mmol), Pd(PPh$_3$)$_4$ (142 mg, 0.12 mmol) and Na$_2$CO$_3$ (523 mg, 4.94 mmol). The flask was evacuated under high vacuum for 1-2 mins and refilled with Argon. The vacuum purge procedure was repeated three times. Then H$_2$O (2.47 mL), EtOH (1.23 mL) and toluene (24.7 mL) were added successively and the reaction was stirred at 100° C. overnight. The reaction mixture was then concentrated under reduced pressure to remove all the volatiles and the residue mixture was loaded directly on a celite cartridge and purified on CombiFlash with RediSep Gold silica column Hexane/EtOAc to give the mono-Suzuki coupling product P5-a (671 mg, 1.84 mmol, 75%). $^1$H NMR (500 MHz, CDCl$_3$) δ 8.51 (d, J=5.0 Hz, 1H), 7.93 (d, J=8.0 Hz, 1H), 7.41 (ddd, J=7.0, 7.0, 2.0 Hz, 1H), 7.23 (d, J=5.0 Hz, 1H), 7.13 (ddd, J=7.5, 7.5, 1.0 Hz, 1H), 7.41 (dd, J=7.5, 2.0 Hz, 1H), 6.15 (s, 1H), 3.66 (s, 3H), 1.46 (s, 9H).

5a (98 mg, 88%) was obtained from P5-a (100 mg, 0.28 mmol) and 4-fluoro-2-(4,4,5,5-tetramethyl-1,3,2-dioxaborolan-2-yl)aniline (78 mg, 0.33 mmol) following the procedure for the synthesis of P5-a. $^1$H NMR (500 MHz, CDCl$_3$) δ 12.12 (s, 1H), 9.05 (d, J=4.5 Hz, 1H), 8.46 (dd, J=9.5, 3.0 Hz, 1H), 7.98 (brs, 1H), 7.51 (ddd, J=7.5, 7.5, 1.0 Hz, 1H), 7.39 (d, J=5.0 Hz, 1H), 7.25-7.20 (m, 2H), 7.07 (dd, J=7.5, 1.0 Hz, 1H), 6.74 (dd, J=9.0, 5.0 Hz, 1H), 6.14 (s, 1H), 1.31 (s, 9H).

To a solution of 5a (49 mg, 0.12 mmol) in CH$_2$Cl$_2$ (2 mL) was added TFA (0.184 mL, 2.41 mmol) and the reaction was stirred at rt for 24 h. The reaction mixture was then concentrated under reduced pressure to afford the desired product 14-F-TEACOP 270 6a as a TFA salt (45 mg, 60%). $^1$H NMR (500 MHz, DMSO-d$_6$) δ 9.04 (d, J=5.0 Hz, 1H), 8.46 (d, J=8.0 Hz, 1H), 8.33-8.30 (m, 2H), 7.71-7.65 (m, 2H), 7.61-7.55 (m, 2H), 7.37 (dd, J=7.0, 7.0 Hz, 1H). As outlined in FIG. 32, prodrug 1.25a can be produced by reacting TEACOP 270 1 with di-tert-butyl chloromethyl phosphate in the presence of base. The t-butyl protecting groups can be removed using TFA or other acids, followed by neutralization using NaHCO$_3$.

Prodrug 1.25b can be produced by reacting TEACOP 270 1 with Chloromethyl Pivalate in the presence of base.

Prodrug 1.25c can be produced by reacting TEACOP 270 1 with 2, 5, 8, 11, 14-Pentaoxapentadecanoic acid, chloromethyl ester.

Prodrug 1.25d can be produced by first reacting 4-Piperidineacetic acid, 1-[(1,1-dimethylethoxy)carbonyl]-, chloromethyl ester with NaI to produce the more reactive 4-Piperidineacetic acid, 1-[(1,1-dimethylethoxy)carbonyl]-, iodomethyl ester, followed by addition to TEACOP 270 in the presence of base, followed by Boc-deprotection using acidic conditions.

Prodrug 1.25e can be produced by reacting TEACOP 270 with Carbonochloridic acid, 2-(4-methyl-1-piperazinyl) ethyl ester in the presence of base.

Prodrug 1.25f can be produced by reacting TEACOP 270 with Carbonochloridic acid, 2-[[2-[ [(1,1-dimethylethoxy)carbonyl]amino]ethyl]dithio]ethyl ester in the presence of base, followed by N-Boc deprotection using acidic conditions.

Example 3: ADME Testing

Figures 32, 33:
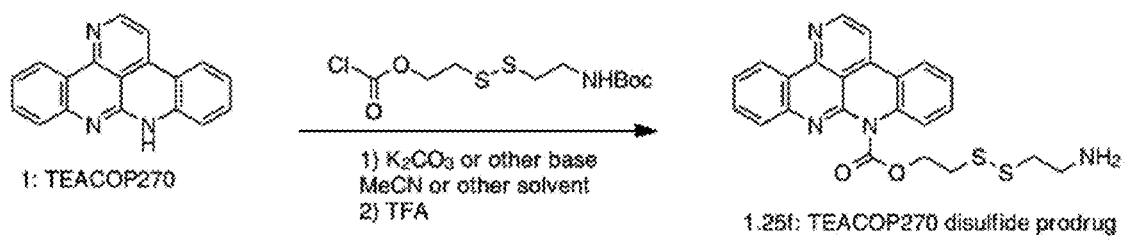
FIG. 33 shows results of TEACOP270 tier 1 ADME test.

TEACOP270 was tested using the ADME (Absorption, Distribution, Metabolism and Elimination) screening and the results are shown in FIG. 33. No mutagenicity is detected with the compound as shown in FIG. 34. Lipophilicity (Log D): A common measure for lipophilicity is the distribution coefficient, log D, which takes into account the compound's ionized and non-ionized forms, and therefore the measurement is done at different pH values. Typically the most interesting is pH 7.4, since the majority of known drugs contain ionizable groups and are likely to be charged at physiological pH.

Assay Design:
Test articles are assayed in triplicate
One concentration of test article (typically 10 µM)
n-Octanol is the partition solvent
Ratio of buffer: Octanol is 1:1 (other ratios available)
Positive control: Testosterone (high log D7.4 value)
Negative control: Tolbutamide (low log D7.4 value)
Analysis: LC/MS/MS measurement of parent compoundReport: Log D7.4 valueQuantity of test article required: 1.0-2.0 mg Summary of Assay: Lipophilicity of compounds is assessed using the golden standard "shake-flask" method. The compound is dissolved in a solution with equal amounts of octanol and water, shaken for 3 hours, and then measured for the amount of compound in each phase. Log D values are calculated by the log ([compound]octanol/[compound]buffer).

Hepatic Microsome Stability Assay Procedure—

Metabolic stability was assessed in the presence of Human and mouse liver microsomes (XenoTech). All liquid dispense and transfer steps were performed with the Freedom Evo automated liquid handler (Tecan US). NADPH, a required cofactor for CYP450 metabolism, was provided by the NADPH Regenerating System, Solutions A (BD Biosciences) and B (BD Biosciences). Compound stock solutions were initially prepared in 100% DMSO and subsequently diluted in acetonitrile for the assay. The pH of the reactions was kept at 7.4 with potassium phosphate buffer (BD Biosciences). The reaction wells were prepared by adding microsomes to a well and allowed to warm to 37° C. Then compound was added to each well. The reactions were started by adding NADPH to the reaction well containing microsomes and compounds. Negative controls received buffer only (instead of NADPH). Immediately after reaction are started, 0 min aliquots were promptly collected and mixed in a separate well with ice cold acetonitrile (spiked with internal standards) to quench the reactions. The remainder of the reaction volume was incubated at 37° C. with shaking. An additional aliquot was collected at 60 min after the start of the reaction and promptly quenched with ice cold acetonitrile (spiked with an internal standard). Samples were vortexed and centrifuged at 3700 rpm for 10 min. The amount of compound in the supernatant was determined by LC/MS/MS (ThermoScientific, Endura) and the percent of parent compound remaining after 60 min was calculated by the following formula:

$$\% \text{ parent compound remaining} = \left[\frac{\text{Concentration at 60 min}}{\text{Concentration at 0 min}} \times 100\right]$$

All reactions were run in triplicate, except negative controls (no NADPH) which were performed as single reactions. Results reported are the mean of each reaction triplicate, normalized to the internal standard, and expressed as a percent of compound remaining after the incubation time.

Assay Details:
Human and Mouse Liver Microsomes: 0.5 mg/mL protein concentration
NADPH Regenerating System: 1.55 mM NADP+, 1.33 mM glucose-6-phosphate, 1.33 mM Magnesium chloride, and 0.4 U/mL glucose-6 phosphate dehydrogenase Incubation Temperature: 37° C.
Incubation Time: 60 min
Standards: Verapamil-HCl and Testosterone, at 20 µM and 50 µM, respectively
Test compound at 1 µM
Assay DMSO final concentration: 0.5%
Assay ACN final concentration: 1.2%

Plasma Stability—

Stability of the compound in human and mouse plasma (BioChemed Services) was determined. All liquid dispense and transfer steps were performed with the Freedom Evo automated liquid handler (Tecan US). Plasma was allowed to thaw at room temperature prior to preparing the assay solution of plasma: 1×PBS (1:1). The assay solution was warmed up at 37° C. prior of adding the compound. Immediately after compounds were added, time 0 min aliquots were promptly collected and mixed with cold acetonitrile (spiked with an internal standard). The remainder of the reaction volume was incubated at 37° C. with shaking. Additional aliquots were collected 180 min after the start of the reaction and promptly quenched with cold acetonitrile (spiked with an internal standard). Samples were centrifuged at 3000 rpm for 10 min. The amount of compound in the supernatant was determined by LC/MS/MS (Applied Biosystems, Sciex API4000 Q-Trap) and the percent of parent compound remaining after 180 min was calculated by the following formula:

$$\% \text{ parent compound remaining} = \left[\frac{\text{Concentration at 180 min}}{\text{Concentration at 0 min}} \times 100\right]$$

Results reported are the mean of each reaction duplicate, normalized to the internal standard, and expressed as a percent of compound remaining after the incubation time.

Assay Details:
Human Plasma in K3 EDTA
Procaine and Procainamide were used as standards. Procaine is highly unstable in human plasma, Procainamide is highly stable in human plasma.
Assay concentrations of standards and test compound: 1 µM
Incubation Time: 3 hrs
Reaction pH: 7.4
Assay DMSO final concentration: 2.5%

The Ames screening detects both frameshift and base-pair substitution mutations using 4 *Salmonella typhimurium* tester strains (TA97a, TA98, TA100, and TA1535) and 1 *Escherichia coli* strain (WP2 uvrA pKM101). Strains TA97a and TA98 detect frameshift mutations, and TA100, TA1535, and WP2 uvrA pKM101 detect base-pair substitution mutations. This scaled-down Ames test uses minimal compound, is conducted with and without metabolic activation (S9 fraction), and uses multiwell plates. The Ames screen for TEACOP 270 was tested in duplicate with strains TA97a, TA98, TA100, TA1535, and WP2 uvrA pKM101 in the presence and absence of a metabolic activation system (Aroclor™ 1254 induced rat liver S9 microsomal fraction) at 7.8, 15.5, 31, 62.5, 125, and 250 ng/well. Positive control compounds were used at 4 different concentrations to ensure the assay system was sensitive to known mutagenic compounds. DMSO was used as the vehicle control.

REFERENCES

Ahmadian, M., J. M. Suh, N. Hah, C. Liddle, A. R. Atkins, M. Downes and R. M. Evans (2013). "PPARgamma signaling and metabolism: the good, the bad and the future." *Nat Med* 19(5): 557-566.

Bergander, L., E. Wincent, A. Rannug, M. Foroozesh, W. Alworth and U. Rannug (2004). "Metabolic fate of the Ah receptor ligand 6-formylindolo[3,2-b]carbazole." *Chem Biol Interact* 149(2-3): 151-164.

Bessede, A., M. Gargaro, M. T. Pallotta, D. Matino, G. Servillo, C. Brunacci, S. Bicciato, E. M. Mazza, A. Macchiarulo, C. Vacca, R. Iannitti, L. Tissi, C. Volpi, M. L. *Belladonna*, C. Orabona, R. Bianchi, T. V. Lanz, M. Platten, M. A. Della Fazia, D. Piobbico, T. Zelante, H. Funakoshi, T. Nakamura, D. Gilot, M. S. Denison, G. J. Guillemin, J. B. DuHadaway, G. C. Prendergast, R. Metz, M. Geffard, L. Boon, M. Pirro, A. Iorio, B. Veyret, L. Romani, U. Grohmann, F. Fallarino and P. Puccetti (2014). "Aryl hydrocarbon receptor control of a disease tolerance defence pathway." *Nature* 511(7508): 184-190.

Bisson, W. H., D. C. Koch, E. F. O'Donnell, S. M. Khalil, N. I. Kerkvliet, R. L. Tanguay, R. Abagyan and S. K. Kolluri (2009). "Modeling of the aryl hydrocarbon receptor (AhR) ligand binding domain and its utility in virtual ligand screening to predict new AhR ligands." *J Med Chem* 52(18): 5635-5641.

Bjeldanes, L. F., J. Y. Kim, K. R. Grose, J. C. Bartholomew and C. A. Bradfield (1991). "Aromatic hydrocarbon responsiveness-receptor agonists generated from indole-3-carbinol in vitro and in vivo: comparisons with 2,3,7,8-tetrachlorodibenzo-p-dioxin." *Proc Natl Acad Sci USA* 88(21): 9543-9547.

Bohar, Z., J. Toldi, F. Fulop and L. Vecsei (2015). "Changing the face of kynurenines and neurotoxicity: therapeutic considerations." *Int J Mol Sci* 16(5): 9772-9793.

Boitano, A. E., J. Wang, R. Romeo, L. C. Bouchez, A. E. Parker, S. E. Sutton, J. R. Walker, C. A. Flaveny, G. H. Perdew, M. S. Denison, P. G. Schultz and M. P. Cooke (2010). "Aryl hydrocarbon receptor antagonists promote the expansion of human hematopoietic stem cells." *Science* 329(5997): 1345-1348.

Brown, K. S. and D. Becher (1967). "The mass spectra of the kynurenines." *Tetrahedron Letters* 18: 1721-1726.

Chang, C., D. R. Smith, V. S. Prasad, C. L. Sidman, D. W. Nebert and A. Puga (1993). "Ten nucleotide differences, five of which cause amino acid changes, are associated with the Ah receptor locus polymorphism of C57BL/6 and DBA/2 mice." *Pharmacogenetics* 3 (6): 312-321.

Changsirivathanathamrong, D., Y. Wang, D. Rajbhandari, G. J. Maghzal, W. M. Mak, C. Woolfe, J. Duflou, V. Gebski, C. G. dos Remedios, D. S. Celermajer and R. Stocker (2011). "Tryptophan metabolism to kynurenine is a potential novel contributor to hypotension in human sepsis." *Crit Care Med* 39(12): 2678-2683.

Cheng, J., W. Li, B. Kang, Y. Zhou, J. Song, S. Dan, Y. Yang, X. Zhang, J. Li, S. Yin, H. Cao, H. Yao, C. Zhu, W. Yi, Q. Zhao, X. Xu, M. Zheng, S. Zheng, L. Li, B. Shen and Y. J. Wang (2015). "Tryptophan derivatives regulate the transcription of Oct4 in stem-like cancer cells." *Nat Commun* 6: 7209.

Dolwick, K. M., H. I. Swanson and C. A. Bradfield (1993). "In vitro analysis of Ah receptor domains involved in ligand-activated DNA recognition." *Proc Natl Acad Sci USA* 90(18): 8566-8570.

Ema, M., N. Ohe, M. Suzuki, J. Mimura, K. Sogawa, S. Ikawa and Y. Fujii-Kuriyama (1994). "Dioxin binding activities of polymorphic forms of mouse and human arylhydrocarbon receptors." *J Biol Chem* 269(44): 27337-27343.

Esser, C., A. Rannug and B. Stockinger (2009). "The aryl hydrocarbon receptor in immunity." *Trends Immunol* 30(9): 447-454.

Goodsell, D. S., G. M. Morris and A. J. Olson (1996). "Automated docking of flexible ligands: applications of AutoDock." *J Mol Recognit* 9(1): 1-5.

Han, D., S. R. Nagy and M. S. Denison (2004). "Comparison of recombinant cell bioassays for the detection of Ah receptor agonists." *Biofactors* 20(1): 11-22.

Helferich, W. G. and M. S. Denison (1991). "Ultraviolet photoproducts of tryptophan can act as dioxin agonists." *Mol Pharmacol* 40(5): 674-678.

Hubbard, T. D., I. A. Murray, W. H. Bisson, T. S. Lahoti, K. Gowda, S. G. Amin, A. D. Patterson and G. H. Perdew (2015). "Adaptation of the human aryl hydrocarbon receptor to sense microbiota-derived indoles." *Sci Rep* 5: 12689.

Hubbard, T. D., I. A. Murray and G. H. Perdew (2015). "Indole and Tryptophan Metabolism: Endogenous and Dietary Routes to Ah Receptor Activation." *Drug Metab Dispos* 43(10): 1522-1535.

Husted, A. S., M. Trauelsen, O. Rudenko, S. A. Hjorth and T. W. Schwartz (2017). "GPCR-Mediated Signaling of Metabolites." *Cell Metab* 25(4): 777-796.

Jasiewicz, M., M. Moniuszko, D. Pawlak, M. Knapp, M. Rusak, R. Kazimierczyk, W. J. Musial, M. Dabrowska and K. A. Kaminski (2016). "Activity of the kynurenine pathway and its interplay with immunity in patients with pulmonary arterial hypertension." *Heart* 102(3): 230-237.

Jonker, J. W., J. M. Suh, A. R. Atkins, M. Ahmadian, P. Li, J. Whyte, M. He, H. Juguilon, Y. Q. Yin, C. T. Phillips, R. T. Yu, J. M. Olefsky, R. R. Henry, M. Downes and R. M. Evans (2012). "A PPARgamma-FGF1 axis is required for adaptive adipose remodelling and metabolic homeostasis." *Nature* 485(7398): 391-394.

Korashy, H. M. and A. O. El-Kadi (2006). "The role of aryl hydrocarbon receptor in the pathogenesis of cardiovascular diseases." *Drug Metab Rev* 38(3): 411-450.

Lamas, B., M. L. Richard, V. Leducq, H. P. Pham, M. L. Michel, G. Da Costa, C. Bridonneau, S. Jegou, T. W. Hoffmann, J. M. Natividad, L. Brot, S. Taleb, A. Couturier-Maillard, I. Nion-Larmurier, F. Merabtene, P. Seksik, A. Bourrier, J. Cosnes, B. Ryffel, L. Beaugerie, J. M. Launay, P. Langella, R. J. Xavier and H. Sokol (2016). "CARD9 impacts colitis by altering gut microbiota metabolism of tryptophan into aryl hydrocarbon receptor ligands." *Nat Med* 22(6): 598-605.

Leklem, J. E. (1971). "Quantitative aspects of tryptophan metabolism in humans and other species: a review." *Am J Clin Nutr* 24(6): 659-672.

Li, X., T. A. Gianoulis, K. Y. Yip, M. Gerstein and M. Snyder (2010). "Extensive in vivo metabolite-protein interactions revealed by large-scale systematic analyses." *Cell* 143(4): 639-650.

McIntosh, B. E., J. B. Hogenesch and C. A. Bradfield (2010). "Mammalian Per-Arnt-Sim proteins in environmental adaptation." *Annu Rev Physiol* 72: 625-645.

Mezrich, J. D., J. H. Fechner, X. Zhang, B. P. Johnson, W. J. Burlingham and C. A. Bradfield (2010). "An interaction between kynurenine and the aryl hydrocarbon receptor can generate regulatory T cells." *J Immunol* 185(6): 3190-3198.

Nguyen, L. P. and C. A. Bradfield (2008). "The search for endogenous activators of the aryl hydrocarbon receptor." *Chem Res Toxicol* 21(1): 102-116.

Nguyen, N. T., A. Kimura, T. Nakahama, I. Chinen, K. Masuda, K. Nohara, Y. Fujii-Kuriyama and T. Kishimoto (2010). "Aryl hydrocarbon receptor negatively regulates dendritic cell immunogenicity via a kynurenine-dependent mechanism." *Proc Natl Acad Sci USA* 107(46): 19961-19966.

O'Mahony, S. M., G. Clarke, Y. E. Borre, T. G. Dinan and J. F. Cryan (2015). "Serotonin, tryptophan metabolism and the brain-gut-microbiome axis." *Behav Brain Res* 277: 32-48.

Opitz, C. A., U. M. Litzenburger, F. Sahm, M. Ott, I. Tritschler, S. Trump, T. Schumacher, L. Jestaedt, D. Schrenk, M. Weller, M. Jugold, G. J. Guillemin, C. L. Miller, C. Lutz, B. Radlwimmer, I. Lehmann, A. von Deimling, W. Wick and M. Platten (2011). "An endogenous tumour-promoting ligand of the human aryl hydrocarbon receptor." *Nature* 478(7368): 197-203.

Oxenkrug, G. F. (2010). "Metabolic syndrome, age-associated neuroendocrine disorders, and dysregulation of tryptophan-kynurenine metabolism." *Ann NY Acad Sci* 1199: 1-14.

Pandini, A., A. A. Soshilov, Y. Song, J. Zhao, L. Bonati and M. S. Denison (2009). "Detection of the TCDD binding-fingerprint within the Ah receptor ligand binding domain by structurally driven mutagenesis and functional analysis." *Biochemistry* 48(25): 5972-5983.

Poland, A., D. Palen and E. Glover (1994). "Analysis of the four alleles of the murine aryl hydrocarbon receptor." *Mol Pharmacol* 46(5): 915-921.

Polyzos, K. A. and D. F. Ketelhuth (2015). "The role of the kynurenine pathway of tryptophan metabolism in cardiovascular disease. An emerging field." *Hamostaseologie* 35(2): 128-136.

Procopio, M., A. Lahm, A. Tramontano, L. Bonati and D. Pitea (2002). "A model for recognition of polychlorinated dibenzo-p-dioxins by the aryl hydrocarbon receptor." *Eur J Biochem* 269(1): 13-18.

Rannug, A., U. Rannug, H. S. Rosenkranz, L. Winqvist, R. Westerholm, E. Agurell and A. K. Grafstrom (1987). "Certain photooxidized derivatives of tryptophan bind with very high affinity to the Ah receptor and are likely to be endogenous signal substances." *J Biol Chem* 262(32): 15422-15427.

Rannug, U., A. Rannug, U. Sjoberg, H. Li, R. Westerholm and J. Bergman (1995). "Structure elucidation of two tryptophan-derived, high affinity Ah receptor ligands." *Chem Biol* 2(12): 841-845.

Rothhammer, V., I. D. Mascanfroni, L. Bunse, M. C. Takenaka, J. E. Kenison, L. Mayo, C. C. Chao, B. Patel, R. Yan, M. Blain, J. I. Alvarez, H. Kebir, N. Anandasabapathy, G. Izquierdo, S. Jung, N. Obholzer, N. Pochet, C. B. Clish, M. Prinz, A. Prat, J. Antel and F. J. Quintana (2016). "Type I interferons and microbial metabolites of tryptophan modulate astrocyte activity and central nervous system inflammation via the aryl hydrocarbon receptor." *Nat Med* 22(6): 586-597.

Rudzite, V., G. Sileniece, D. Liepina, A. Dalmane and R. Zirne (1991). "Impairment of kynurenine metabolism in cardiovascular disease." *Adv Exp Med Biol* 294: 663-667.

Santagata, S., L. S. Eberlin, I. Norton, D. Calligaris, D. R. Feldman, J. L. Ide, X. Liu, J. S. Wiley, M. L. Vestal, S. H. Ramkissoon, D. A. Orringer, K. K. Gill, I. F. Dunn, D. Dias-Santagata, K. L. Ligon, F. A. Jolesz, A. J. Golby, R. G. Cooks and N. Y. Agar (2014). "Intraoperative mass spectrometry mapping of an onco-metabolite to guide brain tumor surgery." *Proc Natl Acad Sci USA* 111(30): 11121-11126.

Savouret, J. F., A. Berdeaux and R. F. Casper (2003). "The aryl hydrocarbon receptor and its xenobiotic ligands: a fundamental trigger for cardiovascular diseases." *Nutr Metab Cardiovasc Dis* 13(2): 104-113.

Schmidt, J. V. and C. A. Bradfield (1996). "Ah receptor signaling pathways." *Annu Rev Cell Dev Biol* 12: 55-89.

Serhan, C. N. (2014). "Pro-resolving lipid mediators are leads for resolution physiology." *Nature* 510(7503): 92-101.

Singh, N. P., U. P. Singh, M. Rouse, J. Zhang, S. Chatterjee, P. S. Nagarkatti and M. Nagarkatti (2016). "Dietary Indoles Suppress Delayed-Type Hypersensitivity by Inducing a Switch from Proinflammatory Th17 Cells to Anti-Inflammatory Regulatory T Cells through Regulation of MicroRNA." *J Immunol* 196(3): 1108-1122.

Stevens, E. A., J. D. Mezrich and C. A. Bradfield (2009). "The aryl hydrocarbon receptor: a perspective on potential roles in the immune system." *Immunology* 127(3): 299-311.

Stone, T. W. and L. G. Darlington (2002). "Endogenous kynurenines as targets for drug discovery and development." *Nat Rev Drug Discov* 1(8): 609-620.

Tokuyama, T., S. Senoh, T. Sakan, K. S. Brown, Jr. and B. Witkop (1967). "The photoreduction of kynurenic acid to kynurenine yellow and the occurrence of 3-hydroxy-L-kynurenine in butterflies." *J Am Chem Soc* 89(4): 1017-1021.

Wei, Y. D., L. Bergander, U. Rannug and A. Rannug (2000). "Regulation of CYP1A1 transcription via the metabolism of the tryptophan-derived 6-formylindolo[3,2-b]carbazole." *Arch Biochem Biophys* 383(1): 99-107.

Wei, Y. D., H. Helleberg, U. Rannug and A. Rannug (1998). "Rapid and transient induction of CYP1A1 gene expression in human cells by the tryptophan photoproduct 6-formylindolo [3,2-b]carbazole." *Chem Biol Interact* 110(1-2): 39-55.

Xing, Y., M. Nukaya, K. Satyshur, L. Jiang, V. Stanevich, E. N. Korkmaz, L. Burdette, G. Kennedy, Q. Cui and C. A. Bradfield (2012). "Identification of the Ah-receptor structural determinants for ligand preferences." *Toxicol Sci*.

Yore, M. M., I. Syed, P. M. Moraes-Vieira, T. Zhang, M. A. Herman, E. A. Homan, R. T. Patel, J. Lee, S. Chen, O. D. Peroni, A. S. Dhaneshwar, A. Hammarstedt, U. Smith, T. E. McGraw, A. Saghatelian and B. B. Kahn (2014). "Discovery of a class of endogenous mammalian lipids with anti-diabetic and anti-inflammatory effects." *Cell* 159(2): 318-332.

Zelante, T., R. G. Iannitti, C. Cunha, A. De Luca, G. Giovannini, G. Pieraccini, R. Zecchi, C. D'Angelo, C. Massi-Benedetti, F. Fallarino, A. Carvalho, P. Puccetti and L. Romani (2013). "Tryptophan catabolites from microbiota engage aryl hydrocarbon receptor and balance mucosal reactivity via interleukin-22." *Immunity* 39(2): 372-385.

Zelentsova, E. A., P. S. Sherin, O. A. Snytnikova, R. Kaptein, E. Vauthey and Y. P. Tsentalovich (2013). "Photochemistry of aqueous solutions of kynurenic acid and kynurenine yellow." *Photochem Photobiol Sci* 12(3): 546-558.

Each publication, patent, and patent publication cited in this disclosure is incorporated in reference herein in its entirety. The present invention is not intended to be limited to the foregoing examples, but encompasses all such modifications and variations as come within the scope of the appended claims.

We claim:

1. A compound of formula (I):

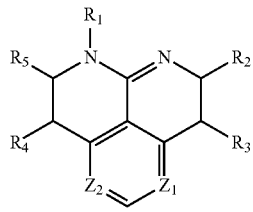

or a pharmaceutically acceptable salt and individual diasteromers thereof, wherein $Z_1$ and $Z_2$ are each independently selected from nitrogen or —CH;

$R_1$ being selected from hydrogen and unsubstituted or substituted $C_{1-3}$ alkyl, where the alkyl is substituted with 1-2 constituents selected from hydroxy, halo, phenyl, and heterocyclic moieties;

$R_2$ and $R_3$ are joined together to form a first ring, the first ring being selected from substituted or unsubstituted cycloalkane, substituted or unsubstituted benzene, and substituted or unsubstituted heterocycle; and $R_4$ and $R_5$ are joined together to form a second ring, the second ring being selected from a substituted or unsubstituted cycloalkane, a substituted or unsubstituted benzene, and a substituted or unsubstituted heterocycle.

2. The compound of claim 1, wherein the first ring and second ring are unsubstituted benzene.

3. The compound of claim 1, wherein the first ring or the second ring is substituted benzene with one or more constituents selected from hydroxyl, halo, methoxy, $C_{1-3}$ alkyl, $C_{1-3}$ alkenyl, $C_{1-3}$-alkynyl, —O-$C_{1-3}$ alkyl, wherein the alkyl is unsubstituted or substituted with constituents selected from hydroxy, chloro and trifluoromethyl.

4. The compound of claim 1, wherein the first ring or the second ring is unsubstituted or substituted heterocycle with one or more constituents selected from hydroxyl, halo, methoxy, $C_{1-3}$ alkyl, $C_{1-3}$ alkenyl, $C_{1-3}$-alkynyl, —O-$C_{1-3}$ alkyl, wherein the alkyl is unsubstituted or substituted with constituents selected from hydroxy, chloro and trifluoromethyl.

5. The compound of claim 1, wherein the compound is:

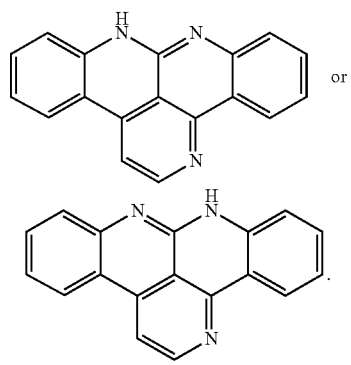

6. A compound of formula (II):

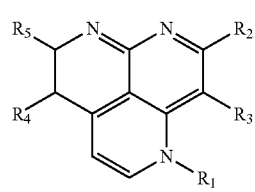

or a pharmaceutically acceptable salt and individual diasteromers thereof, wherein $R_1$ being selected from hydrogen and unsubstituted or substituted $C_{1-3}$ alkyl, where the alkyl is substituted with 1-2 constituents selected from hydroxy, halo, phenyl, and heterocyclic moieties;

$R_2$ and $R_3$ are joined together to form a first ring, the first ring being selected from substituted or unsubstituted cycloalkane, substituted or unsubstituted benzene, and substituted or unsubstituted heterocycle; and $R_4$ and $R_5$ are joined together to form a second ring, the second ring being selected from a substituted or unsubstituted cycloalkane, a substituted or unsubstituted benzene, and a substituted or unsubstituted heterocycle.

7. The compound of claim 6, wherein the first ring and the second ring are unsubstituted benzene.

8. The compound of claim 6, wherein the first ring or the second ring is substituted benzene with one or more constituents selected from hydroxyl, halo, $C_{1-3}$ alkyl, $C_{1-3}$ alkenyl, $C_{1-3}$-alkynyl, —O-$C_{1-3}$ alkyl, wherein the alkyl is unsubstituted or substituted with constituents selected from hydroxy, chloro and trifluoromethyl.

9. The compound of claim 6, wherein the first ring or the second ring is unsubstituted or substituted heterocycle with one or more constituents selected from hydroxyl, halo, $C_{1-3}$ alkyl, $C_{1-3}$ alkenyl, $C_{1-3}$-alkynyl, —O-$C_{1-3}$ alkyl, wherein the alkyl is unsubstituted or substituted with constituents selected from hydroxy, chloro and trifluoromethyl.

10. The compound of claim 6, wherein the compound is

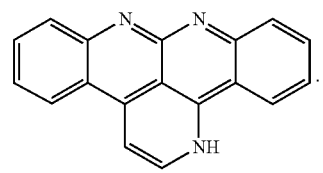 [SMILES: C1=Cc2c3ccccc3nc3nc4ccccc4c(c23)N1]

11. The compound of formula (III):

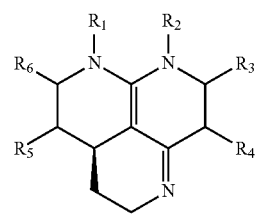

or a pharmaceutically acceptable salt and individual diasteromers thereof, wherein $R_1$ and $R_2$ are each individually selected from hydrogen and unsubstituted or substituted $C_{1-3}$ alkyl, where the alkyl is substituted with 1-2 constituents selected from hydroxy, halo, phenyl, and heterocyclic moieties;

R₃ and R₄ are joined together to form a first ring, the first ring being selected from substituted or unsubstituted cycloalkane, substituted or unsubstituted benzene, and substituted or unsubstituted heterocycle; and R₅ and R₆ are joined together to form a second ring, the second ring being selected from a substituted or unsubstituted cycloalkane, a substituted or unsubstituted benzene, and a substituted or unsubstituted heterocycle.

12. The compound of claim 11, wherein the first ring and the second ring are unsubstituted benzene.

13. The compound of claim 11, wherein the first ring or the second ring is substituted benzene with one or more constituents selected from hydroxyl, halo, $C_{1-3}$ alkyl, $C_{1-3}$ alkenyl, $C_{1-3}$-alkynyl, —O—$C_{1-3}$ alkyl, wherein the alkyl is unsubstituted or substituted with constituents selected from hydroxy, chloro and trifluoromethyl.

14. The compound of claim 11, wherein the first ring or the second ring is unsubstituted or substituted heterocycle with one or more constituents selected from hydroxyl, halo, $C_{1-3}$ alkyl, $C_{1-3}$ alkenyl, $C_{1-3}$-alkynyl, —O-$C_{1-3}$ alkyl, wherein the alkyl is unsubstituted or substituted with constituents selected from hydroxy, chloro and trifluoromethyl.

15. The compound of claim 11, wherein the compound is:

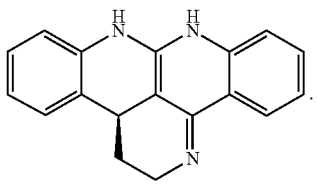 [SMILES: c1ccc2c(c1)NC1=C3C2=NCC[C@H]3c2ccccc2N1]

16. The compound of formula (IV)

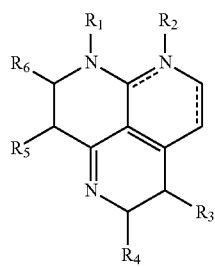

(IV)

or a pharmaceutically acceptable salt and individual diasteromers thereof, wherein R₁ being selected from hydrogen and unsubstituted or substituted $C_{1-3}$ alkyl, where the alkyl is substituted with 1-2 constituents selected from hydroxy, halo, phenyl, and heterocyclic moieties;

R₂ being selected from hydrogen, unsubstituted or substituted $C_{1-3}$ alkyl, and nothing, where the alkyl is substituted with 1-2 constituents selected from hydroxy, halo, phenyl, and heterocyclic moieties R₃ and R₄ are joined together to form a first ring, the first ring being selected from substituted or unsubstituted cycloalkane, substituted or unsubstituted benzene, and substituted or unsubstituted heterocycle; and R₅ and R₆ are joined together to form a second ring, the second ring being selected from a substituted or unsubstituted cycloalkane, a substituted or unsubstituted benzene, and a substituted or unsubstituted heterocycle; and wherein the dotted line represents an optional covalent bond.

17. The compound of claim 16, wherein the first ring and the second ring are unsubstituted benzene.

18. The compound of claim 16, wherein the first ring or the second ring is substituted benzene with one or more constituents selected from hydroxyl, halo, methoxy, $C_{1-3}$ alkyl, $C_{1-3}$-alkenyl, $C_{1-3}$-alkynyl, —O-$C_{1-3}$ alkyl, wherein the alkyl is unsubstituted or substituted with constituents selected from hydroxy, chloro and trifluoromethyl.

19. The compound of claim 16, wherein the first ring or the second ring is unsubstituted or substituted heterocycle with one or more constituents selected from hydroxyl, halo, $C_{1-3}$ alkyl, $C_{1-3}$ alkenyl, $C_{1-3}$-alkynyl, —O—$C_{1-3}$ alkyl, wherein the alkyl is unsubstituted or substituted with constituents selected from hydroxy, chloro and trifluoro.

20. A prodrug of the compound of claim 1.

21. A method of activating the aryl hydrocarbon receptor (AHR) in a subject, the method comprising administering an effective amount of the compound of claim 1.

* * * * *

UNITED STATES PATENT AND TRADEMARK OFFICE
CERTIFICATE OF CORRECTION

PATENT NO. : 10,611,764 B2
APPLICATION NO. : 16/185870
DATED : April 7, 2020
INVENTOR(S) : Yongna Xing et al.

It is certified that error appears in the above-identified patent and that said Letters Patent is hereby corrected as shown below:

In the Specification

Column 20, Line 54, "ECSO" should be --EC50--.

Column 21, Line 4, "ECSO" should be --EC50--.

Column 22, Line 21, "ECSO" should be --EC50--.

Column 29, Line 2, "(AU C)" should be --(AUC)--.

Column 29, Line 36, "ng/mL" should be --µg/mL--.

Column 30, Line 60, "$CH_2C12$" should be --$CH_2Cl_2$--.

Column 34, Line 59, "ng/well" should be --µg/well--.

Signed and Sealed this
Twenty-sixth Day of May, 2020

Andrei Iancu
*Director of the United States Patent and Trademark Office*